US012279876B2

(12) United States Patent
Shachar et al.

(10) Patent No.: US 12,279,876 B2
(45) Date of Patent: Apr. 22, 2025

(54) CATHETER FOR CARDIAC AND RENAL NERVE SENSING AND MEDIATION

(71) Applicant: Neuro-Kinesis Corporation, Inglewood, CA (US)

(72) Inventors: Josh Shachar, Santa Monica, CA (US); Marc Rocklinger, Marina del Rey, CA (US); Eli Gang, Los Angeles, CA (US); Doyoung Kim, Montrose, CA (US)

(73) Assignee: Neuro-Kinesis Corporation, Inglewood, CA (US)

( * ) Notice: Subject to any disclaimer, the term of this patent is extended or adjusted under 35 U.S.C. 154(b) by 794 days.

(21) Appl. No.: 17/468,460

(22) Filed: Sep. 7, 2021

(65) Prior Publication Data

US 2022/0047202 A1 Feb. 17, 2022

(51) Int. Cl.
*A61B 5/367* (2021.01)
*A61B 5/00* (2006.01)
*A61B 5/20* (2006.01)
*A61B 5/287* (2021.01)
*A61B 5/294* (2021.01)
*A61B 5/35* (2021.01)
*A61B 5/388* (2021.01)

(52) U.S. Cl.
CPC ............ *A61B 5/367* (2021.01); *A61B 5/0006* (2013.01); *A61B 5/0017* (2013.01); *A61B 5/201* (2013.01); *A61B 5/287* (2021.01); *A61B 5/294* (2021.01); *A61B 5/35* (2021.01); *A61B 5/388* (2021.01); *A61B 5/4836* (2013.01); *A61B 5/686* (2013.01); *A61B 5/7203* (2013.01); *A61B 2562/0209* (2013.01)

(58) Field of Classification Search
None
See application file for complete search history.

(56) References Cited

U.S. PATENT DOCUMENTS 5,769,791 A * 6/1998 Benaron ............ A61B 17/3417
600/476
6,546,270 B1 * 4/2003 Goldin ................... A61B 18/12
600/374

(Continued)

FOREIGN PATENT DOCUMENTS

WO 2021084476 5/2021
WO 2021165882 8/2021

OTHER PUBLICATIONS

Shachar, Josh Yehoshua, "The Use of Local Amplifier and MOSFET Sensor Array in Measuring Bioelectric Signals and Its Clinical Application," research paper, Jan. 1, 2018, <https://joshshachar.com/wp-content/uploads/2021/07/jshachar-introduction-to-mosfet-technology-research-paper.pdf>.

(Continued)

*Primary Examiner* — Carl H Layno
*Assistant Examiner* — Manolis Pahakis
(74) *Attorney, Agent, or Firm* — Kirton McConkie; Brian Tucker

(57) ABSTRACT

A catheter is provided which exhibits higher resolution at its distal end. The higher resolution can be accomplished by combining and amplifying signals received at electrodes locally. These combined and amplified signals can then be digitized locally and transmitted for further processing. Optical communication channels may be used.

26 Claims, 46 Drawing Sheets
(1 of 46 Drawing Sheet(s) Filed in Color)

(56) References Cited

U.S. PATENT DOCUMENTS

| | | | | |
|---|---|---|---|---|
| 6,569,160 B1* | 5/2003 | Goldin | ............... | A61B 18/1492 |
| | | | | 606/49 |
| 6,898,464 B2* | 5/2005 | Edell | ................... | A61B 5/0017 |
| | | | | 128/903 |
| 11,844,912 B2* | 12/2023 | Alsheikh | ................ | A61B 34/20 |
| 2007/0156128 A1* | 7/2007 | Jimenez | ............. | A61B 18/1492 |
| | | | | 606/41 |
| 2007/0276286 A1* | 11/2007 | Miller | ................... | A61B 5/053 |
| | | | | 600/564 |
| 2014/0018792 A1* | 1/2014 | Gang | ................ | A61B 18/1492 |
| | | | | 606/41 |
| 2014/0081114 A1* | 3/2014 | Shachar | ................... | A61B 5/24 |
| | | | | 600/378 |
| 2015/0313501 A1* | 11/2015 | Shachar | ................ | A61B 5/302 |
| | | | | 600/374 |
| 2015/0351652 A1* | 12/2015 | Marecki | ............ | A61B 18/1492 |
| | | | | 29/829 |
| 2018/0078300 A1 | 3/2018 | Paul et al. | | |
| 2018/0303414 A1* | 10/2018 | Toth | ................... | A61N 1/36135 |
| 2020/0383599 A1* | 12/2020 | Hayes | ................... | A61B 5/301 |

OTHER PUBLICATIONS

European Patent Office, Extended European Search Report, Oct. 10, 2024.

* cited by examiner

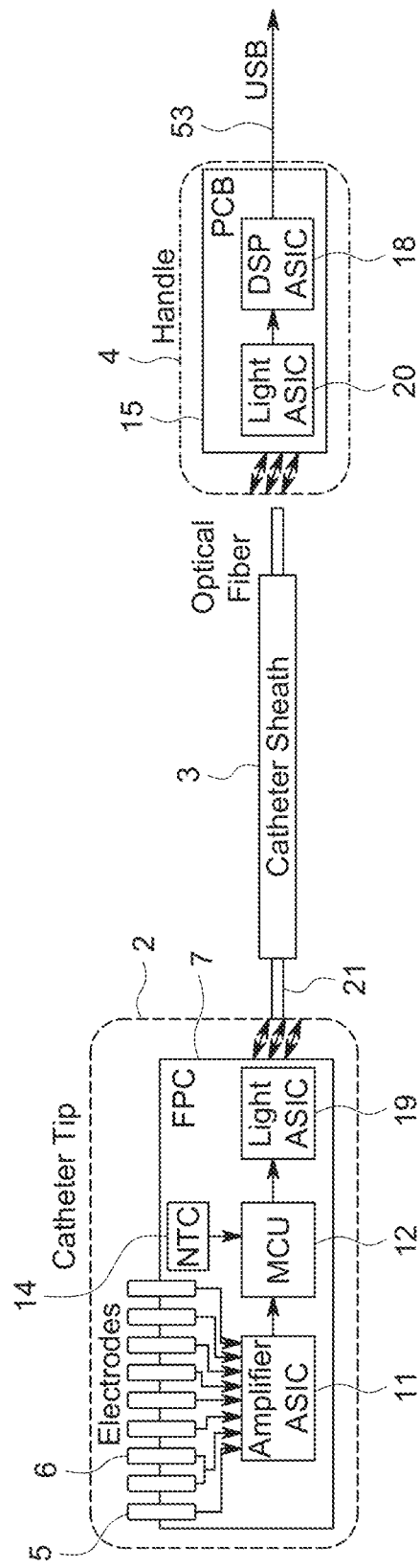
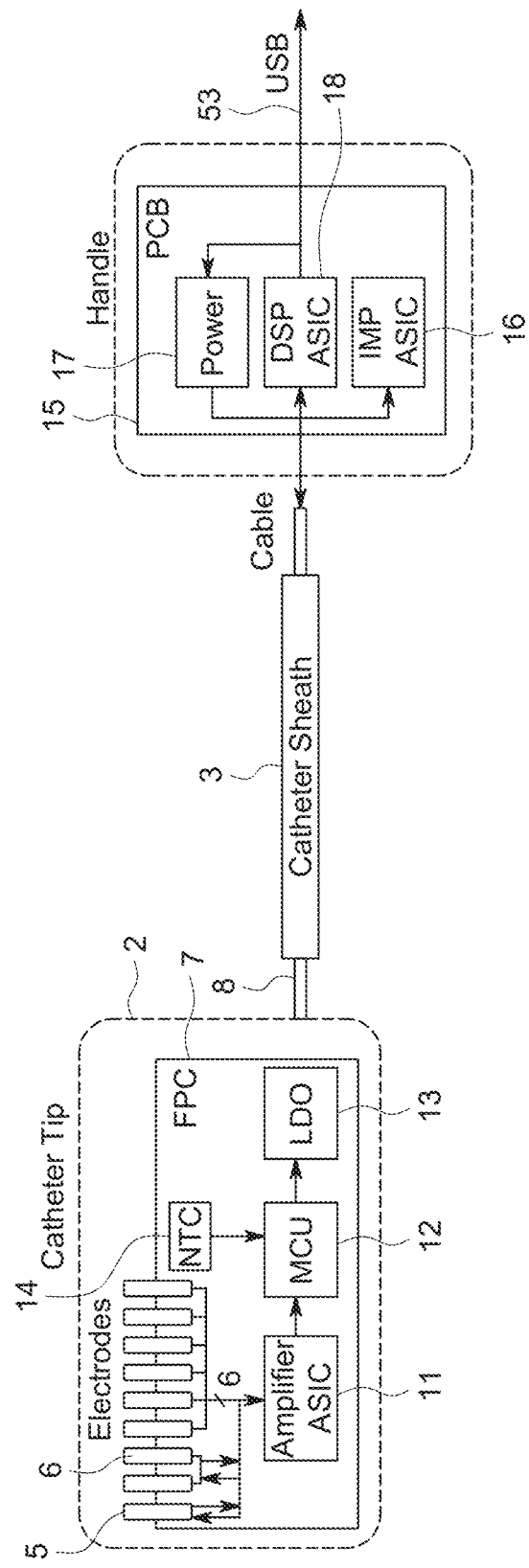
FIG. 3A
FIG. 3B

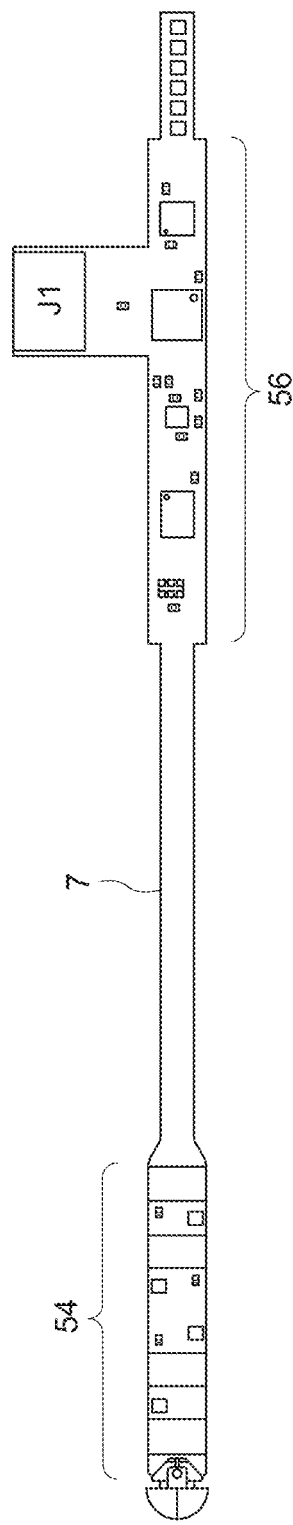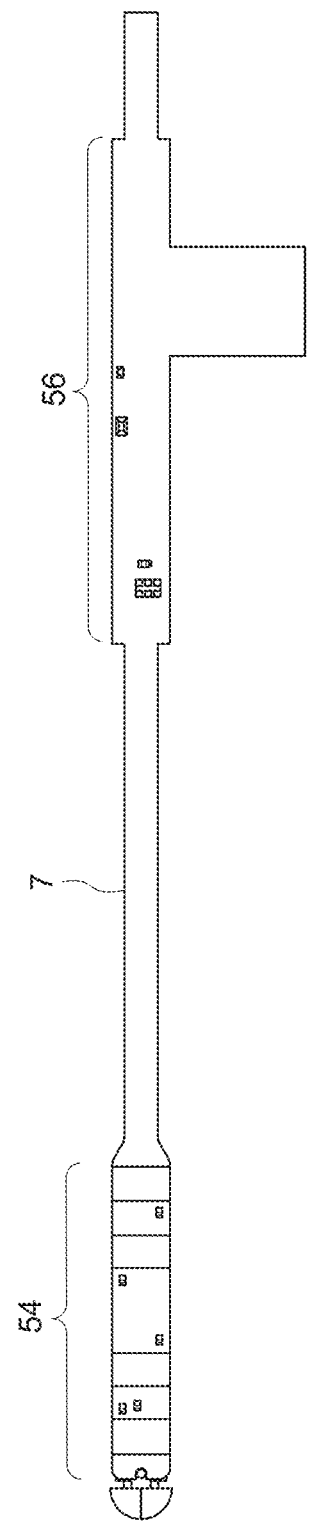
FIG. 15A
FIG. 15B 0.25 Pitch, Plano-Plano

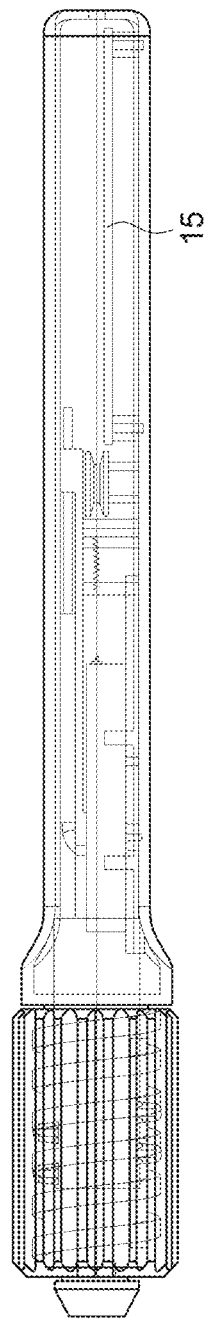
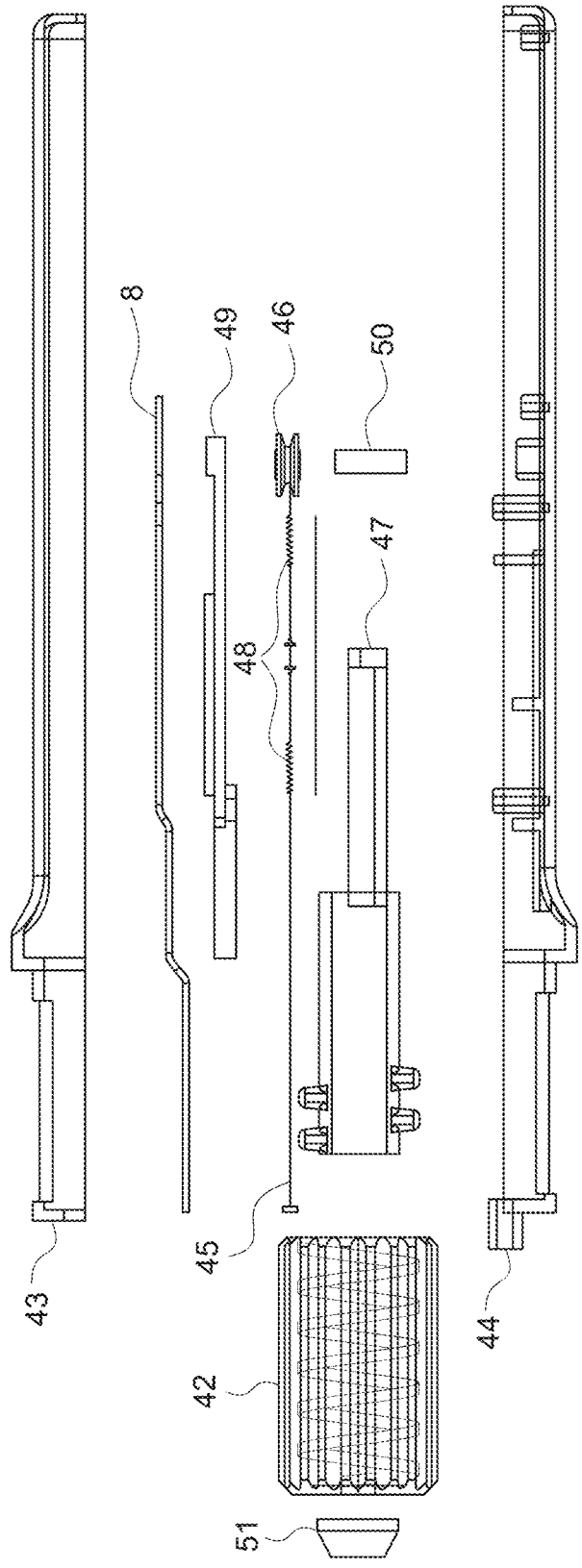
FIG. 36A
FIG. 36B

CATHETER FOR CARDIAC AND RENAL NERVE SENSING AND MEDIATION

This application claims priority to, and the benefit of the earlier filing date as a continuation in part of US patent application entitled, "Optically Coupled Catheter and Method of Using the Same, filed on May 28, 2019, Ser. No. 16/424,202, now U.S. Pat. No. 11,540,775, pursuant to 35 USC 120, the contents of which are incorporated herein by reference.

BACKGROUND

Field of the Technology

The invention relates to the field of catheters as a diagnostic device with applications in electrophysiological studies, e.g.: mapping nerve pathways during ablative procedures such as renal denervation, in various cardiological procedures, and neurological mapping.

Description of the Prior Art

Clinical electrophysiologic mapping and ablation procedures are commonly performed in the Electrophysiology Laboratory (EP Lab). The successful ablation of cardiac arrhythmias is critically dependent on the acquisition and interpretation of multiple low amplitude signals (typically ranging in the 25 µV to several mV size). As practiced today, both signal acquisition and interpretation suffer from shortcomings of existing recording equipment, as well as limitations of the physician's ability to interpret the acquired intracardiac electrograms (EGM's) owing to lack of signal clarity and knowledge about the nature of the propagated signal in complex three-dimensional cardiac tissue.

With respect to signal acquisition, the EGM's are recorded in the presence of multiple sources of electric noise and interference. Displaying these signals with maximal signal-to-noise (S/N) ratio, in a clinically useful fashion, has been a major challenge over the years. From a noise standpoint, the EP Lab is a source of significant electromagnetic interference (EMI). The patient is connected to multiple pieces of electronic equipment, each of which generates a leakage current which needs to meet safety standards. The patient also acts as a grounded antenna, being both capacitively and inductively coupled to the main voltage wiring in the EP Lab as well as picking up noise from headsets, mobile phones from staff and other wireless monitors. As a result, significant voltages can be measured on the patient's body (1-3 V RMS) in a wide range of frequency spectrum.

In addition, catheters used for signal acquisition from the patient's heart, by their very nature, i.e., multiple electrodes connected by long cables to a distant differential amplifier, are subject to line "noise", ambient EMI, cable motion artifacts, faulty connections, etc. Over the years, progress has been made in shielding and grounding of the EP Lab, as well as improvements in isolation of patient-connected instruments, and improvements of common-mode rejection ratios (CMRR) of differential amplifiers used to enhance the EGM's of interest. Nonetheless, recording of small and complex signals in the EP Lab continues to be a critical problem and solutions need to be found so that cases are done more efficiently, and outcomes are improved.

Some of the technical and interpretive problems that continue to plague the clinical electrophysiologist in the clinical EP Lab include the following. High frequency signals such as pulmonary vein potentials and near-field continuous fractionated signals (CAFÉ) may be inadvertently filtered out with a typical 50-60 Hz notch filter commonly used in standard EP systems. Common filters (analog or digital) limit our ability to distinguish between "near-field" signals (which have more high frequency content) from "far-filed" signals (which typically have lower frequency energy).

Current analog-to-digital (A/D) sampling rates available in commercially available recording and mapping systems are inadequate to completely analyze the high frequency content of complex signals as well as in differentiating the small high frequency signals such as pulmonary vein potentials, accessory pathway potentials, and the complex details of scar-related conduction in diseased myocardium. High gain amplification is frequently used during mapping in an attempt to identify small signals (e.g., less than 100 µV). Amplifiers introduce saturation artifacts (with relatively long offsets) which can conceal or envelop signals of interest that follow large signals such as those introduced during pacing in an EP study, e.g. entrainment mapping.

Conventional systems that use high gain settings also introduce "clipping" of the signals of interest; while software "clipping" of large signals can eliminate the saturation artifact mentioned above, one can be misled when looking at fused waveforms (i.e. pathway potentials during an accessory pathway ablation) if the selected clipping level by the software prevents visualization of two discrete, fused signals and instead represents them as a single, wide signal. Phantom signals or signals that appear real but are an artifact can also be seen because of the less-than-perfect CMRR of the input amplifiers, especially at higher frequencies.

Conventionally obtained unipolar and bipolar recordings have unique advantages and disadvantages. The disadvantage of conventionally band-passed filtered unipolar EGM recording is the inability to distinguish near-field from far-field signals when the near-filed is obtained from diseased myocardium verses far-field from healthy tissue. Using a higher high-pass cutoff frequency can minimize the far-field contribution, but then it may obscure the directional information which the unipolar EGM is meant to convey.

Another disadvantage of unipolar signals is the increased susceptibility to noise because of the differential coupling of interfering signals to the two widely spaced electrodes. Conventional bipolar EGM's, which are the most commonly used electrode-electrode configuration in the EP Lab, also have certain drawbacks. For example, voltage maps of diseased myocardium are frequently obtained in the EP Lab as a means of estimating scar size and searching for conduction "channels". However, given the difference in size between the tip electrode and the more proximal electrode of a bipolar pair, and the fact that, in most cases, the tip is in contact with the tissue with a perpendicular orientation, leaving the proximal electrode offset from the tissue by several millimeters, it is not clear if the voltage on the bipolar electrogram is truly representative of the "quality of tissue" beneath the catheter tip. Thus, differentiating a scar from viable tissue using bipolar voltage measurements can be grossly misleading.

Coupled noise interference during delivery of RF ablation energy is also a common problem during the performance of ablation of cardiac arrhythmias. During the delivery of 40-50 W into a 100-ohm load (i.e. cardiac tissue) requires about a 200 V peak-to-peak sine wave. The cardiac signal of interest is up to 200,000 smaller and is obscured unless sophisticated filtering is used. However, the internal wiring of the mapping/ablation catheters is such that if pacing is performed during ablation, which is not infrequent, coupled interference in the form of high-frequency noise and large baseline drifts will be superimposed on the required electrograms, making observation of reduction and/or disappearance in electrogram amplitude during RF application difficult or even impossible.

With respect to interpretation of complex arrhythmias, especially when multiple colliding wavefronts are recorded, current signal acquisition technologies do not allow for differentiating signals coming from epicardial on mid-myocardial tissues, as opposed to the more readily recorded endocardial signal.

Another limitation of current mapping systems is the inability to measure the thickness of tissue being ablated. This is of paramount safety importance when delivering RF heat energy to potentially thin atrial tissue, and when trying to avoid collateral damage to nearby anatomic structures, such as the esophagus, which is uniquely adjacent to the posterior wall of the left atrium.

What is needed is a method and apparatus for an EP mapping catheter which overcomes each of these limitations and further realizes the advantages listed below.

BRIEF SUMMARY

Potential advantages of the disclosed "smart" Huygens catheter, not including the mechanical handle steering component improvement, include:
i. Elimination of the noise and electromagnetic (EM) interference inherent in the intracardiac electrogram (EGM) acquisition technology currently in use in electrophysiology (EP) Labs;
ii. Significant enhancement of the signal-to-noise (SN) ratio, thus enabling the detection of small (<25 µV) signals without the distortion inherent to current technologies when high-order filtering is employed;
iii. Detection of signals hitherto not available to conventional recording techniques, possibly signals <1-10 µV in size, thereby further defining scar geometry and signal propagation in diseased tissue;
iv. Establishing new paradigms for in vivo description of circuits that involve mid-myocardial and epicardial conduction wavefronts.
v. Rendering the thickness of cardiac tissue, thereby enhancing the safety of ablation procedures.
vi. Further elucidation of the nature of fractionated and complex EGM's, by subtracting far-field signals and enhancing true local tissue potentials.
vii. Recording and localizing sympathetic nerve activity in renal arteries in patients with difficult to treat hypertension, thus making renal artery denervation a more precise procedure and improving the hitherto disappointing results obtained in large clinical trials done to date.
viii. Recording of nerve activity originating in nerve ganglia on the outer surface of the heart, the so-called epicardial ganglionated plexi. This might be crucial in the ablation of atrial fibrillation, the most common arrhythmia treated today in the EP Laboratory.

The catheter has higher resolution, 5-10 micro volts, at its distal end, because the electrodes are amplified locally- or adjacent to the electrode. The electrode signal is then selected by a multiplexer (MUX), converted to a digital word via a local analog-to-digital converter (ADC). The power for the catheter electronics is generated and transmitted by an optical aperture that maintains a stable base direct current level (DC), at a wavelength of 850 nm, and a measured signal of the potential impedance measured at the electrode interface with the endocardial or renal tissue is transmitted back to the reader for display via an optical data signal with a wavelength of 450 nm. Such transmission of power to the electronics and its data signal return is transferred via an optical fiber from and to the proximal end of the catheter respectively, where an electronic driver circuit provides a stable photonic power to run the electronics at the distal end of the catheter. The control circuit at the tip is capable of receiving the information generated by the electrodes, namely the electro anatomical data points containing the impedance of the measurement site, its position and its time step, as well as the correlation between contact impedance and contact force in grams. The sensors and circuits in the catheter tip is contained within a 7 Fr. (2.45 mm) catheter, while meeting the safety requirements defined by the standards of the FDA.

The illustrated embodiments of the invention include a method for using an electrophysiology catheter to map neuronal activity of tissue by employing sensing and amplification circuitry disposed in the distal portion of the catheter at the site of biopotential activity to detect and record a local native cardiac signal in cardiac tissue, which detection and recordation spatially and temporally localized with the generation of the native cardiac signal at the situs of its local generation without corruption from far field signals or external electromagnetic noise.

The step of employing sensing and amplification circuitry includes employing a local amplifier active sensor array with capabilities enabling an accurate "one-to-one" correlation while forming an electrophysiological map by measuring spatial position of the situs of local generation and vectorial direction of current movement of the local native signal in the cardiac tissue.

The step of employing the sensing and amplification circuitry includes using the circuitry to make a measurement of biopotential voltage and phase of the local native cardiac signal as a function of time correlated with impedance of the tissue and/or temperature at the local situs of measurement.

The step of employing the sensing and amplification circuitry includes employing the circuitry to detect and record impedance spectroscopy at the local situs of a measured biopotential signal.

The step of employing the sensing and amplification circuitry includes employing the circuitry to detect and record a native local bioelectrical signal in the form of ionic electrochemical avalanche dynamics at a measurement site in tissue by locating an active sensor element adjacent to the measurement site and measuring the native bioelectrical signal by relating its characteristics of time, magnitude and direction in the cardiac tissue without post-processing of the native bioelectrical signal.

The step of employing circuitry for using a native bioelectrical signal is characterized by using circuitry with an improved signal-to-noise ratio, improved spurious-free dynamic range (SFDR), improved signal fidelity, improved sampling rate, improved bandwidth, and improved differentiation of far-field from near-field components in the native signal.

The step of employing an electrophysiological mapping catheter establishes accurate diagnostic maps of axonal nerve endings as detected in renal denervation, measurement of ganglionic plexus activities and neuronal cellular matrices.

The step if employing the sensing and amplification circuitry includes employing an active sensor array in an implantable cardioverter defibrillator (ICD), in an implantable electrophysiological device, in a device for neuromodulation, and in pacemaker leads.

The step of employing the sensing and amplification circuitry comprises employing an active sensor array and where the optical fiber replaces all electrical wiring between the distal portion of the catheter and the handle, so that a signal detected by the active sensor array in the distal portion of the catheter is converted into an uncorruptible digital word and sent to the handle as digital optical data stream.

The step of employing sensing and amplification circuitry in an electrophysiology catheter includes arranging and configuring the catheter as a diagnostic device for use in electrophysiological studies, including mapping nerve pathways during ablative procedures, renal denervation, various cardiological procedures, and neurological mapping.

The method further comprising using an imaging system, including an impedance mapping apparatus in combination with the electrophysiology catheter, which imaging system locates a target within an anatomical context and provides geometric coordinates of specific anatomical destination including identifying different types of arrythmia.

The step of employing the sensing and amplification circuitry includes accurately characterizing fractionation potentials recorded in scarred myocardial tissue, which serve as ablation targets, pulmonary vein potentials and accessory pathway potentials.

The method where further includes deploying one or more electrodes to comprise an array form with geometry configurations such as bipolar, quadripolar, decapolar, or any array with 64 or more electrodes thereby enabling a multiplicity of electrodes to simultaneously capture a complex electro-potential energetic event with an improved signal-to-noise ratio and improved sampling rate commensurable with an improved bandwidth and improved accuracy on a spatiotemporal domain.

The step of employing sensing and amplification circuitry in an electrophysiology catheter comprises providing a standard model for any assessment of the boundary conditions yielding consistent and repeatable data under similar conditions.

The step of providing the standard model includes unifying diagnostic observations under a measurement technique for defining an intracardiac electrogram (EGM) as energetic events, which provides a translation between the electrical map and its substrate so that the substrate is directly correlated to the pathophysiology.

The step of defining the intracardiac electrogram (EGM) includes generating a graphical representation of an energetic bioevent, based on the dielectric ($\kappa$) and conductivity ($\sigma$) measurements of underlying tissues.

The step of employing the sensing and amplification circuitry includes providing a local amplifier to sense and amplify a native local signal where the near-field as well as its far-field component can be distinguished without post-processing.

The illustrated embodiments also extend to a method for using a renal denervation catheter to map neuronal activity of renal tissue by employing pulsing, sensing and amplification circuitry disposed in the distal portion of the catheter at the site of biopotential activity to electrically stimulate, detect and record a local native renal signal in active renal tissue spatially and temporally localized with the generation of the active native renal signal at the situs of its local generation without corruption from far field signals or external electromagnetic noise.

The illustrated embodiments also include an electrophysiology catheter for combination with an external mapping station, which catheter includes: a catheter with a movable catheter tip; one or more electrodes provided on or in an electrode region in a most distal portion of the catheter tip; sensing and amplification circuitry communicated with the one or more electrodes, the sensing and amplification circuitry communicated with digitizing circuitry disposed in a circuitry region in a least distal portion of the catheter tip for locally sensing tissue-based electrophysiological signals and for bidirectionally communicating digital data signals to and from the sensing and amplification and digital circuitry; a flexible bending region of the catheter tip between the most and least distal portions of the catheter tip; a flexible sheath communicated to the sensing and amplification circuitry and digitizing circuitry for transmission of signals thereon; and a handle communicated with the sheath for bidirectionally communicating signals through the sheath between the catheter tip and external mapping station, and for controlling movement of the catheter tip.

In one embodiment the electrophysiology catheter provides transmission of data signals in the sheath is by optical digital signals.

In another embodiment the electrophysiology catheter transmission of data signals in the sheath is by electrical digital signals.

The electrophysiology catheter further includes: an electro-optical system coupled to the catheter tip for transducing digital electrical electrophysiological signals from the sensing and amplification circuitry and digitizing circuitry into digital optical electrophysiological signals; an optical fiber in the sheath for transmitting the digital optical electrophysiological signals to the proximal handle of the catheter; and an optical-electro system disposed in the proximal handle of the catheter for transducing digital optical electrophysiological signals into digital electrical electrophysiological signals.

The handle comprises a steering mechanism where movement of a distal tip of the catheter with respect to tissue contacted by the catheter tip is controlled.

The sensing and amplification circuitry comprises means for making a biopotential measurement to provide a representation of energy contents on a spatial domain and a time domain of a complex electrophysiological waveform, leading to a recursive relationship between a graphical representation of the complex electrophysiological waveform and an underlying biopotential substrate which causes the complex electrophysiological waveform.

The sensing and amplification circuitry includes means for employing a local amplifier active sensor array utilizing impedance spectroscopy at a bioevent site of a measured biopotential signal.

The sensing and amplification circuitry comprises means for using a native bioelectrical signal in the form of ionic electrochemical avalanche dynamics at a measurement site in tissue by locating an active sensor element adjacent to the measurement site and measuring the native bioelectrical signal by relating its characteristics of time, magnitude and direction, without post-processing of the native bioelectrical signal.

The means for using a native bioelectrical signal is characterized by an improved signal-to-noise ratio, improved spurious-free dynamic range (SFDR), improved signal fidelity, improved sampling rate, improved bandwidth, and improved differentiation of far-field from near-field components in the native signal.

The catheter includes an electrophysiological mapping catheter adapted to establish accurate diagnostic maps of axonal nerve endings as detected in renal denervation, measurement of ganglionic plexus activities and neuronal cellular matrices.

The sensing and amplification circuitry comprises an active sensor array in an implantable cardioverter defibrillator (ICD), in an implantable electrophysiological device, in a device for neuromodulation, and in pacemaker leads.

The sensing and amplification circuitry comprises an active sensor array and where an optical fiber is employed instead of any electrical wiring between the catheter tip and the handle, so that a signal detected by the active sensor array in the catheter tip is converted into an uncorruptible digital word and sent to the handle in a digital optical data stream.

The catheter is arranged and configured as a diagnostic device for use in electrophysiological studies, including mapping nerve pathways during ablative procedures, renal denervation, various cardiological procedures, and neurological mapping.

The electrophysiology catheter further includes an imaging system in the external mapping station, including an impedance mapping apparatus, which imaging system enables location of a target within an anatomical context and provides geometric coordinates of specific anatomical destination including identifying different types of arrythmia.

The sensing and amplification circuitry accurately characterizes fractionation potentials recorded in scarred myocardial tissue, which serve as ablation targets, pulmonary vein potentials and accessory pathway potentials.

The one or more electrodes comprise an array forming geometry configurations such as bipolar, quadripolar, decapolar, or any array with 64 or more electrodes to enable a multiplicity of electrodes to simultaneously capture a complex electro-potential energetic event with an improved signal-to-noise ratio and improved sampling rate commensurate with an improved bandwidth and improved accuracy on a spatiotemporal domain.

The electrophysiology catheter further includes means for providing a standard model for any assessment of boundary conditions yielding consistent and repeatable data under similar conditions.

The standard model unifies diagnostic observations under a measurement technique to define an intracardiac electrogram (EGM) as energetic events, which provides a translation between the electrical map and its tissue substrate so that the substrate is directly correlated to the pathophysiology.

The defined intracardiac electrogram (EGM) comprises a graphical representation of an energetic bioevent, based on the dielectric (κ) and conductivity (σ) measurements of underlying tissues.

The sensing and amplification circuitry comprises a local amplifier to sense and amplify a native local signal where the near-field as well as its far-field component can be distinguished without post-processing, The electrophysiology catheter is in combination with an external computer where the optical-electro system disposed in the handle of the catheter for transducing digital optical electrophysiological signals into digital electrical electrophysiological signals comprises a digital signal processor, a laser controlled by the digital signal processor and coupled to the optical fiber, a dichroic mirror for feeding back a portion of light from the laser to a photodiode coupled to the digital signal processor to regulate the laser, where light carrying digital optical signals from the optical fiber are coupled to the photodiode and thence to the digital signal processor, the digital signal processor coupled to the external computer for data storage and processing.

The one or more electrodes comprise a plurality of electrodes and where the sensing and amplification circuitry includes: a light emitting diode/photodiode (LED/PD); a serial peripheral interface (SPI) bus; a plurality of amplifier application specific integrated circuits (amp ASIC) coupled to corresponding ones of the plurality of electrodes and to the serial peripheral interface (SPI) bus; and a light application specific integrated circuit (ASIC) coupled to the LED/PD, which light ASIC signal conditions and communicates a plurality of signals on the serial peripheral interface (SPI) bus to the plurality of amplifier ASIC's, each of which are coupled to one of the plurality of electrodes, used as sensing points of the catheter tip so that sensed biopotentials from electrodes are locally amplified by amplifier ASICs and communicated via the SPI bus into the light ASIC to be multiplexed out to LED/PD and communicated as multiplexed photonic signals on the optical fiber.

The sensing and amplification circuitry disposed in the distal portion of the catheter tip includes: an optical connector coupled to the optical fiber, the optical connector including a photodiode to convert an optical signal from the optical fiber into an electrical signal, and the optical connector including an LED to convert an electrical signal into an optical signal communicated to the optical fiber; a voltage regulator coupled to the photodiode and powered by a power optical signal received by the photodiode; a charge pump coupled to the voltage regulator; a microcontroller unit (MCU); an analog to digital converter (ADC) coupled to the MCU; an instrument amplifier (IA) coupled to the ADC; an AC-coupling circuit coupled to the IA; a multiplexer (MUX) coupled to the AC-coupling circuit and to the one or more electrodes; where the charge pump is coupled to the MUX and IA for the purpose of supplying power, where the voltage regulator powers and is coupled to the MCU, ADC, IA, AC-coupling circuit and MUX; where the MCU is coupled to the MUX and provides a selection command signals to the MUX to control selection of the one or more electrodes; and where sensed native signals from the one or more electrodes is communicated to the AC-coupling circuit, amplified by the IA, converted to a digital form by the ADC and communicated to the MCU for communication to the LED and transduction into a digital optical form into the optical fiber.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A is a transparent side elevational view; FIG. 2B is a side elevational view of the exterior surface of the catheter tip of FIG. 2A not including exposed electrodes; and FIG. 2C is a exploded side view of certain components in the catheter tip shown in FIGS. 2A and 2B.

FIGS. 3A and 3B are the electrical block diagrams of the Huygens catheter in the optical embodiment and electrical cable embodiments respectively.

FIGS. 15A and 15B are top and bottom elevational views respectively of the assembly drawing of the tip flex printed circuit (FPC) of FIG. 14.

FIG. 20 is an end plan view showing where sections lines A-A are defined. FIG. 20*b* is a top plan view showing where sections lines A-A are defined. FIG. 20*c* is a cross sectional view as seen through section lines A-A.

FIG. 21 also shows the materials covering the safety wire.

FIG. 36A is a transparent side view of the assembled handle. FIG. 36B is an exploded side transparent view of the catheter handle of FIG. 36A and its mechanical components.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

System Overview

Figure 40:
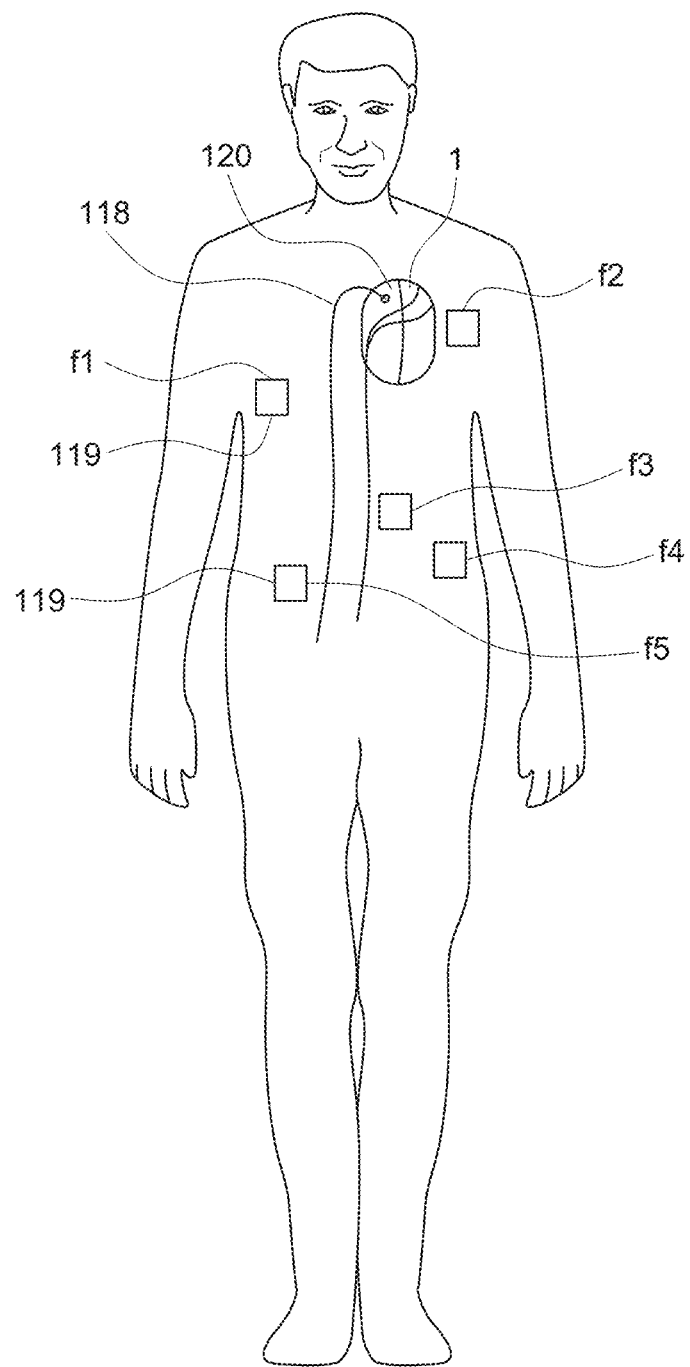
FIG. 40 is a diagram of a patient with a plurality of body electrodes attached to provide a positional frame for a transseptal probing catheter and a reference catheter anchored in the coronary sinus.

It is to be understood that the catheter 1 of the illustrated embodiments is used in a spatial reference frame established in a conventional manner using a plurality of RF emitting body patches 119 shown in FIG. 40, a reference catheter 118 anchored in the coronary sinus 120 to fix an anatomical origin in the heart, and the transseptal probing catheter 1. See for example, PCT/US2008/056277 "Method and apparatus for controlling catheter position and orientation"; PCT/US2009/039659 "Apparatus and method for Lorentz-active Sheath and control of surgical tool"; PCT/US2009/040242 "Method and Apparatus for creating a high resolution map of the electrical and mechanical properties of the heart"; PCT/US2009/064439 "System and Method for catheter Impedance seeking device"; PCT/US2010/052696 "Method for acquiring high density mapping data with a catheter guidance system"; and PCT/US2010/056069 "Method for targeting Catheter electrodes", each and all of which are incorporated herein by reference. RF locational signals applied to and transmitted from the plurality of patches 119, each at a unique frequency assigned to each one of the patches 119, are detected by tip electrodes on catheter 1 and reference catheter 118 thereby returning a corresponding plurality of time stamped RF locational signals depending the time of flight of the locational signal to the reference catheter 118 and catheter 1. The distance from each patch 119 to the reference catheter 118 and catheter 1 is determined by the corresponding time stamp or time of flight of the RF locational signal. By triangulation the relative positions of the reference catheter 118 and catheter 1 are determined in a data processor in a connected conventional mapping station. The position of the reference catheter 118 anchored in the coronary sinus is assigned as the origin of the reference frame and the position of catheter 1 is determined in reference to it. The plurality of patches 118 are pulsed with the RF locational signal at a 50 Hz repetition rate. The periodic movement of the heart is at 1.5 Hz or less, so that relative positional changes of catheter 1 due to heart beat and breathing are easily tracked. The position of the tip of catheter 1 relative to an anatomical map of the heart as measured from the coronary sinus 120 is thus always determined at each instance of time.

The path of the dynamic, avalanche cardiac signals in the heart can be mapped in the cardiac tissue with catheter 1 by tracking the local pacing cardiac pulse, typically in the left atrium. In the case of a heart having scar tissue blocking the proper pathway, diverting the pacing path in usually a shortened path bypassing essential portions of the heart, and causing an arrythmia, sinus rhythm of the heart can be restored if the shortened path is ablated by using an RF ablation catheter to create a small amount of scar tissue across the shortened path. The pacing current then seeks a different path through the heart tissue and hopefully it will be a pathway on or close to the normal pacing circuit. RF ablation continues until a sinus rhythm is achieved indicating the establishment of a normal or near normal pacing circuit. It can readily be appreciated that such ablation therapies are successful only if the local pacing signal, normal or abnormal, in the heart can be reliably and accurately mapped. If the physician is only guessing or estimating where the pacing signal goes, then the ablation sites will be chosen based on guesses, some bad. In order to accurately map native cardiac pulses, the clear and reliable spatial and temporal detection of the local native cardiac pulse must be achieved at each point in the cardiac tissue and recorded. The native cardiac pulse is typically from 25 µV (scar related signals) to 5 mV (surface ECG) with a period of between 80 and 100 ms. When the duration is between 0.10 and 0.12 seconds, it is intermediate or slightly prolonged. A QRS duration of greater than 0.12 seconds is considered abnormal. Normal sinus rhythm and dysrhythmias that arise from above the ventricles will usually have normal QRS complexes. Abnormal QRS complexes are produced by abnormal depolarization of the ventricles. Duration of an abnormal QRS complex is greater than 0.12 seconds.

Complex fractionated atrial electrograms (CFAEs) are defined as electrograms with a cycle length ≥20 ms or shorter, or that were fractionated or displayed continuous electric activity.

This biosignal is awash in larger cardiac signal of the order of mV and external electromagnetic signals from operation room and hospital equipment. In addition to this, the detected signal is transmitted on an EP catheter cable of the order of 1 m long to an external mapping station, possibly several more meters away, all of which is swamped in a sea of electromagnetic noise that e4ndemic to the mapping station circuitry or is picked up on these long wires, leads and cables. Such wires and cables necessarily has some small self-capacitance and inductance to time varying signals with a frequency spectrum, which will distort the phase of the carried signal. Thus, if the native cardiac signal is to be accurately detected and recorded, it must be locally detected at the situs in the heart of the native signal across the local temporal span of its generation, its amplitude and phase detected and recorded or frozen in time, and transmitted noise-fee to the mapping station. The EP catheter system disclosed below achieves that goal. According to the disclosed embodiments, the local native pacing pulse in the heart tissue, which is detected and recorded, includes the spatial position of the tip of catheter 1 <x, y, z>, its angular direction to the next adjacent situs of the native pulse or direction of the native cardia current <θ, φ, ψ>, time <t>, amplitude and phase of the current <V, Θ>, impedance of the detection site <Ω> and temperature of the detection site <T>, for a complete data string of <t, {x, y, z}, {θ, φ, ψ}, V, θ, Ω, T> digitized and transmitted at a 50 Hz repetition rate for each measured situs.

Signals in the EP lab range from 25 µV (scar related signals) to 5 mV (surface ECG). Noise on clean EGM's is on the order of magnitude of less than 20 µV, when everything is properly grounded and shielded. So achieving a SNR of 10, for example, with a biologic signal of 25 µV and a noise of 2.5 µV, is considered good. A signal seen at less than 50 µV is viewed with skepticism. A mid-diastolic potential seen in an infarct scar, which is barely larger than background noise, needs to be seen repeatedly and in the same relationship to other larger signals, in order to be believed to originate from biologic tissue. The frequency content of noise picked up from the patient/antenna can range from 50 Hz to significant harmonics.

Figure 1:
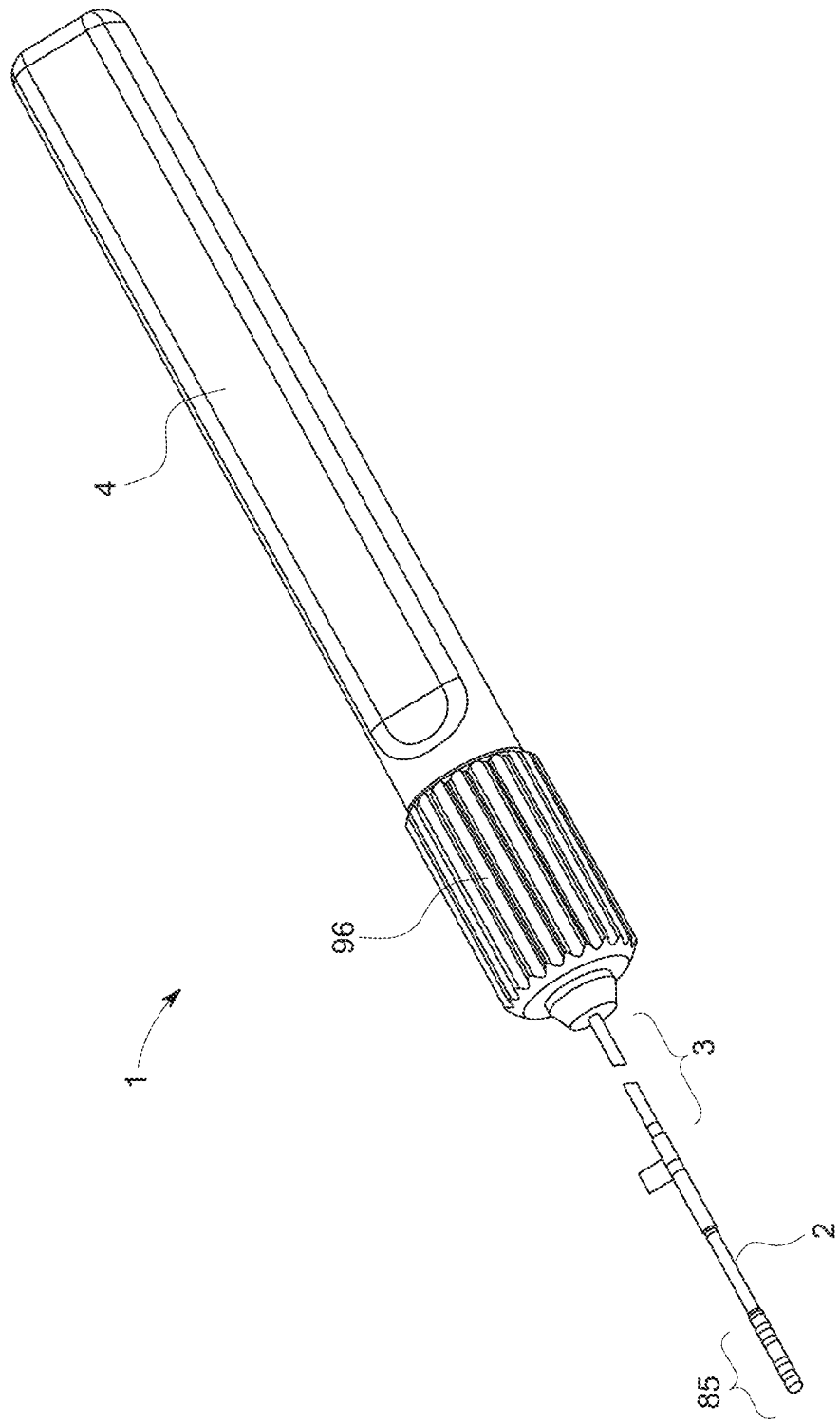
FIG. 1 is a perspective view of the Huygens catheter system, including the handle, sheath and catheter tip.
Figure 2A:
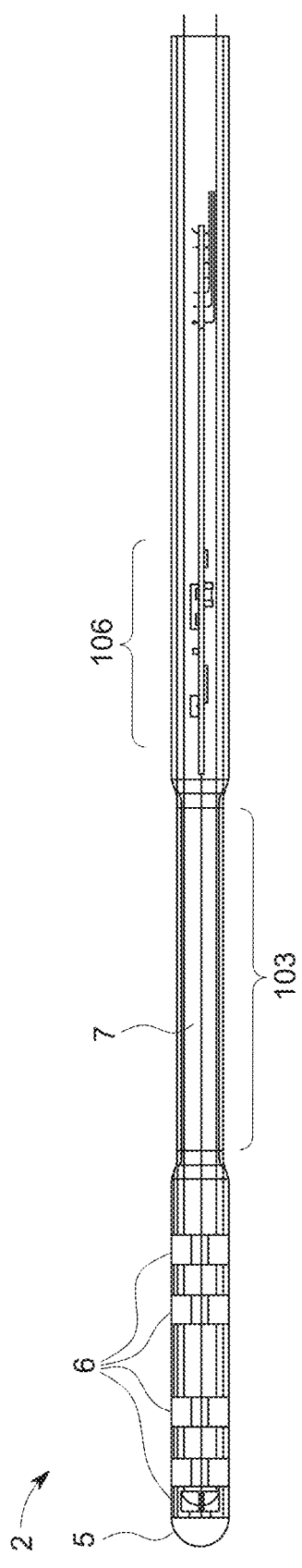
FIGS. 2A-2C are three side views of the catheter tip.
Figure 2B:
Figure 2C:
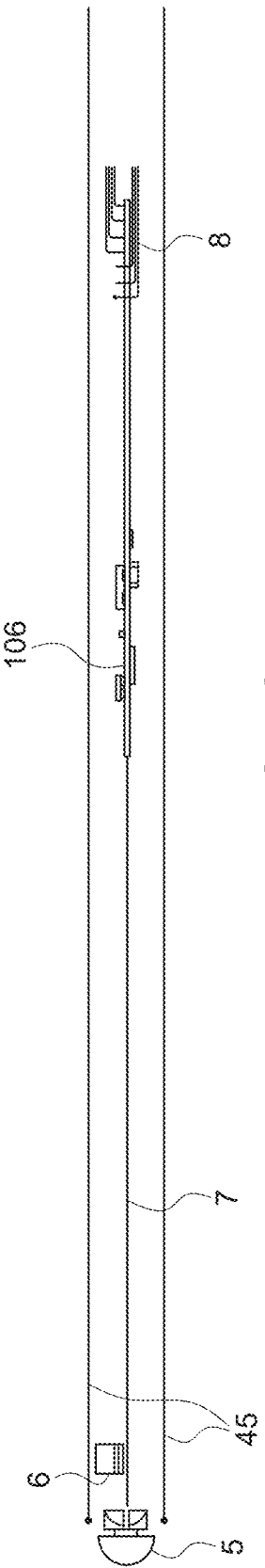

FIG. 1 is a perspective view of the Huygens catheter 1. The catheter 1 is divided into three regions, a catheter tip 2, a sheath 3, and a handle 4. Handle 4 includes an tension adjustment knob 96 described in greater detail in connection with FIG. 38. FIGS. 2A-2C are three side views of the catheter tip 2. FIG. 2A is a transparent side elevational view of tip 2 showing the end nosecone electrode 5, for sets of half cylindrical electrode pairs 6 proximally positioned in tip 2 behind nosecone electrode 5. The electrodes 5, 6 are coupled to FPC 7 and separated by a flexible section 55 of FPC 7. The circuit elements 106 in tip 2, described below, are then carried on FPC 7 proximally from flexible section 55. FIG. 2B is a side elevational view of the exterior surface of the catheter tip 2 which is molded over tip 2 of FIG. 2A as described in connection with FIG. 33.

Figure 33:
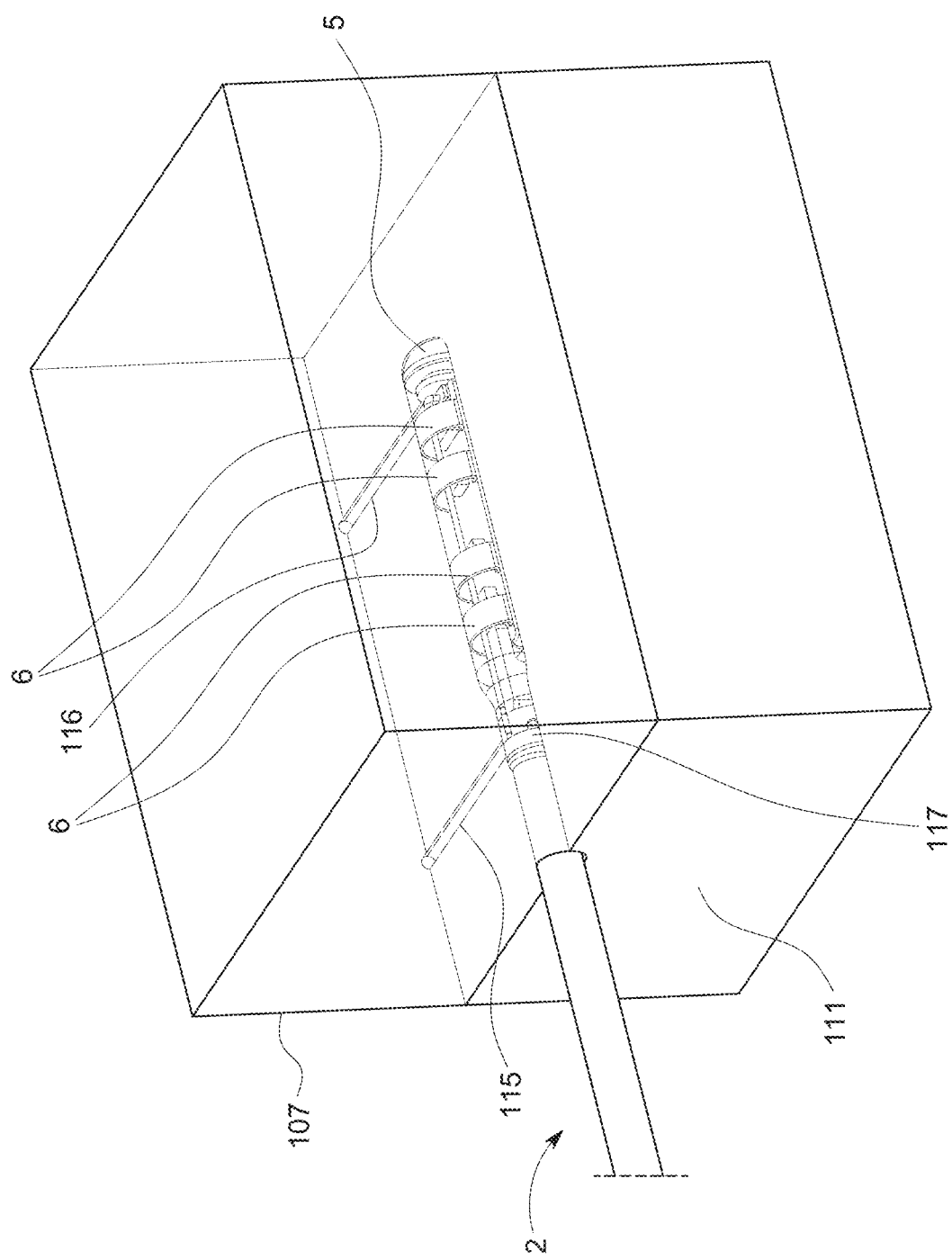
FIG. 33 is a diagram showing the molding process of the catheter tip.

FIG. 33 is a perspective view of a low pressure overmold used to encapsulate catheter tip 2. After catheter tip 2 is fully assembled, as described below, it is placed between upper mold half 107 and lower mold half 111. A medical grade polymer is injected with low pressure through gate 115 distally from sleeve seal 117 on tip 2 to fully pot the electrode array 6 of tip 2. The polymer is forced through electrodes 6 up to nosecone electrode 5 and then exits through vent 116.

FIG. 2C is a exploded side view of certain components in the catheter tip shown in FIGS. 2A and 2B, namely nosecone electrode 5, one of the half cylindrical electrodes 6 with the remaining electrodes 6 omitted for simplicity, FPC 7, pull wires 45, electronics 106 and sheath wires 8 in the electrical cable embodiment of FIG. 3B, all of which components are described below.

FIG. 3A is a block diagram of the Huygens catheter 1 illustrating an embodiment of the catheter system using local amplifiers 11 coupled to the tip electrodes 5, 6. Catheter tip 2 includes an electronic flexible printed circuit (FPC) 7, which carries an amplifier application-specific integrated circuit (ASIC) 11 communicated with a microcontroller 12 (MCU), a negative thermal coefficient thermistor (NTC) 14 having its output coupled to MCU 12, and a tip light ASIC 19 having its input coupled to MCU 12. The light ASIC 19 is optically coupled to the catheter sheath 3 via which includes an optical fiber 21, described in greater detail below. Catheter sheath 3 and optical fiber 21, which may be several meters long, is optically coupled to handle light ASIC 20 which is in the handle printed circuit board (PCB) 15. The handle PCB 15 also carries a digital signal processor (DSP) ASIC 18 that processes the data received from the tip 2. DSP ASIC 18 is communicated with a personal computer 52 or other control system (such as EnSite cardiac mapping system by Abbott of Plymouth, MN or CARTO electroanatomical mapping system by Biosense Webster of Irvine, CA) through a conventional universal serial bus 53 (USB). The USB 53 provides universal asynchronous receiver/transmitter (UART) formatted data communication as well as providing an external power source to the catheter handle 4.

FIG. 3B is a block diagram showing a functional block diagram of an electrical cable embodiment of the Huygens catheter 1, where the optical system is replaced by an electrical or wired communication scheme. At the handle electronics 15, the handle light ASIC 20 is replaced by a power supply 17. Since the tip 2 is connected through an electrical wire bundle 8 in sheath 3, an impedance measuring ASIC 16 is added into the handle PCB 15. The catheter sheath 3 is coupled with wire bundle 8, which comprises six electrical wires, carrying the signals and power lines: VDD, GND, impedance input (IMP IN), impedance output (IMP OUT), data transmission (Tx), and data reception (Rx). These wires are coupled to the tip FPC 7, where Tx and Rx connect to MCU 12, VDD and GND to low dropout regulator (LDO) 13, and impedance input and output to the electrodes 5, 6.

Figure 4A:
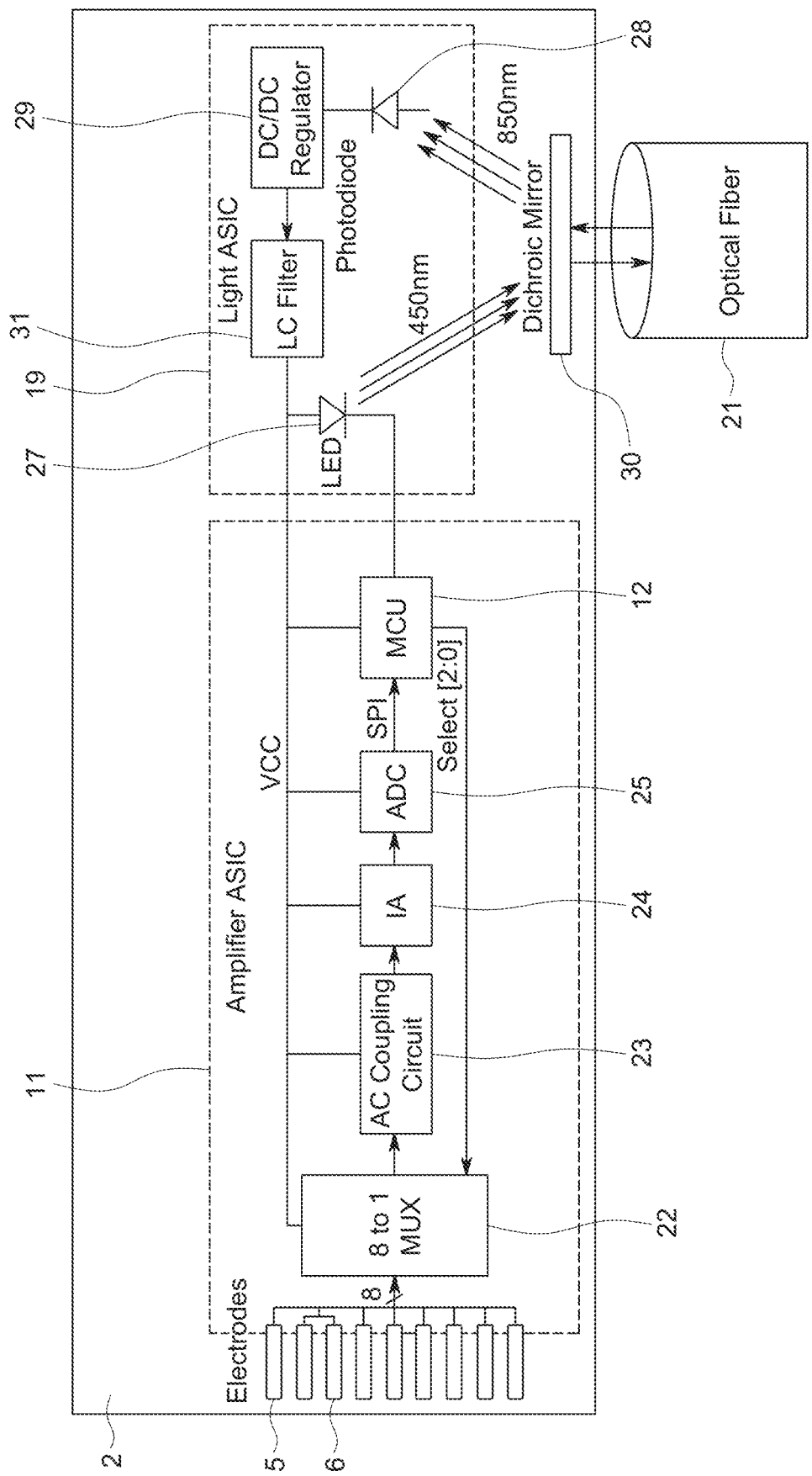
FIGS. 4A and 4B are block diagrams of an electrical and optical components of the catheter tip in the optical and electrical cable embodiments respectively.

FIG. 4A is a more detailed block diagram of the electronics 106 in catheter tip 2. The electronic FPC 7 of the catheter tip 2 is divided into three sections, electrode section 6, amplifier ASIC 11, and tip light ASIC 19. The electrode section 6 includes eight half ring electrodes 6, and one nosecone electrode 5 at the distal end of the tip 2. Amplifier ASIC 11 includes an 8-to-1 multiplexer (MUX) 22 coupled to electrodes 6, AC coupling circuit 23 coupled to MUX 22, which comprises of a capacitor and a resistor, which in turn is coupled to an instrumentation amplifier 24, described in greater detail in the embodiments of FIGS. 10-12, which amplifier 24 is coupled in turn to an analog-to-digital converter 25, which in turn is coupled to microcontroller MCU 12. Light ASIC 19 includes a 470 nm LED 27 electrically controlled by MCU 12 and its optical output coupled to dichroic mirror 30.

Figure 3C:
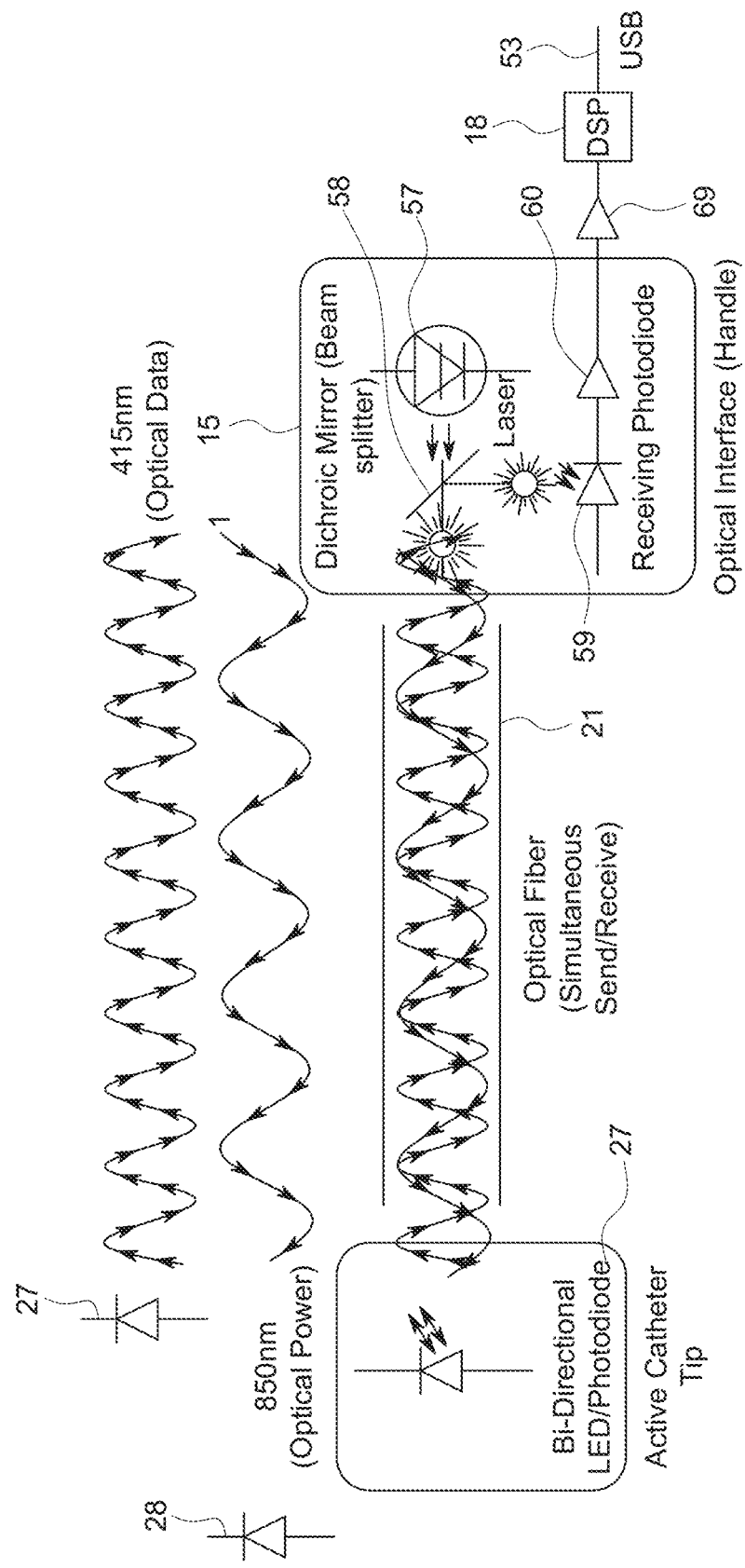
FIG. 3C is a schematic diagram of the primary optical and electrical signals of the optical embodiment of FIG. 3A.

Power is supplied optically in a 850 nm beam carried by fiber optic 21 from handle 4 as diagrammatically shown in FIG. 3C. The 850 nm light is reflected by dichroic mirror 30 into photodiode 28, which has its electrical output coupled to a DC/DC photovoltaic regulator 29, whose output in turn is coupled to an LC frequency band filter 31, whose output in turn is coupled to a voltage supply line VCC coupled to all the circuits components in tip 2. The mirror 30 effectively filters the laser light input into the photodiode 28 to prevent the LED light from entering photodiode 28 and creating a noisy power source. The photodiode 28 receives 850 nm laser light from the optical fiber 21 to provide more than 20 mW of power. This native power is processed through DC/DC regulator 29 that outputs 3.3V which becomes the main voltage source of the tip electronics. This main voltage is cleaned through LC choke filter 31 that truncates the unwanted ripple voltages. The 450 nm light from bidirectional LED/photodiode 27 bidirectionally communicates data signals through dichroic mirror 30 to optical fiber 21, which is then sent to the optical receiver 15 located at the handle 4.

Figure 4B:
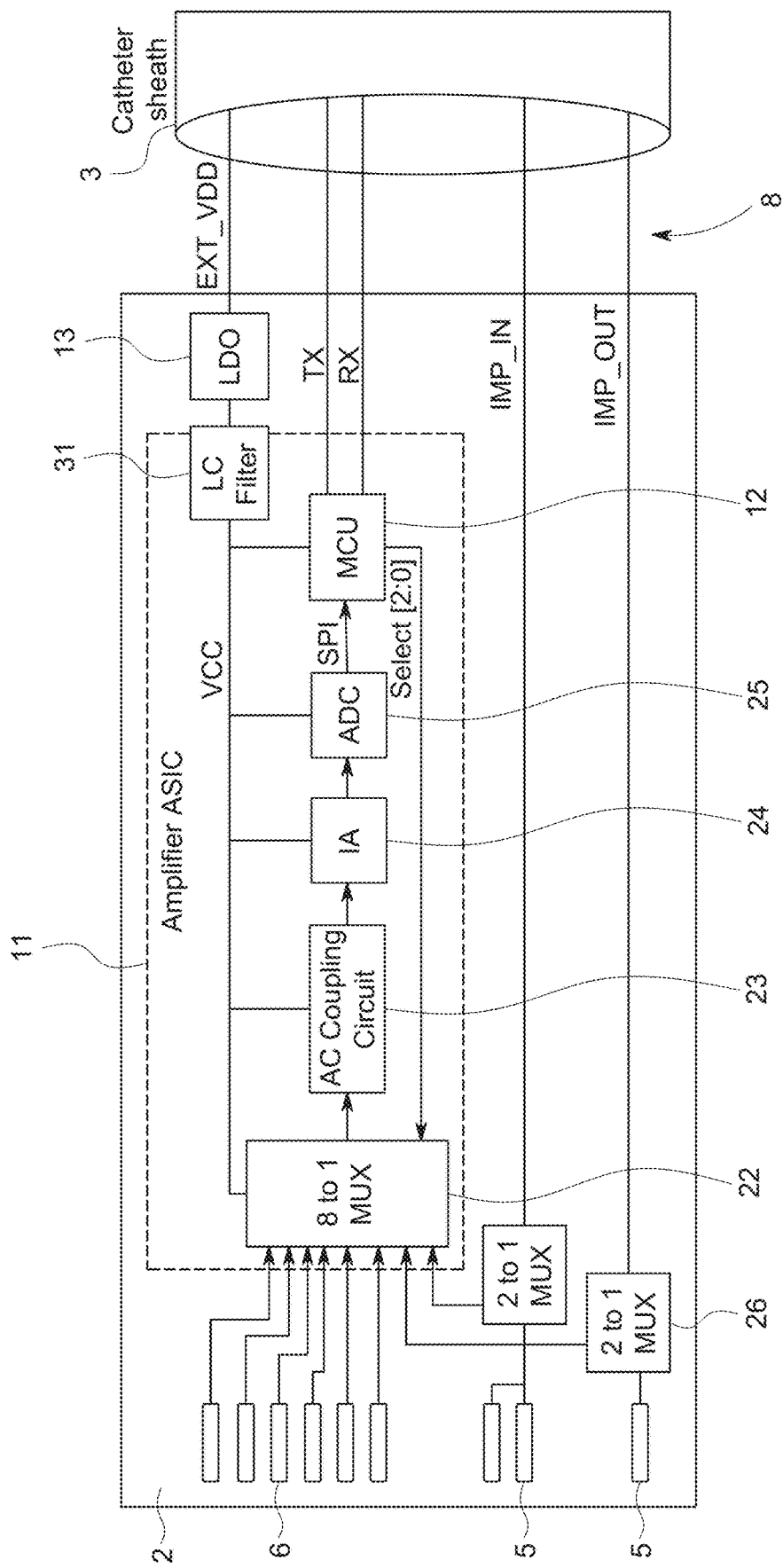

FIG. 4B is a block diagram of another embodiment using an electrical cable comprised of wires 8 instead of an optical signal. The light ASIC 19 of FIG. 3A is removed and electrical wires 8 that include supply voltage VDD, ground, Tx, Rx, impedance input, and impedance output are physically wired to corresponding inputs and outputs on the tip FPC 7. The nosecone electrode 5 serves as both impedance input and biopotential reader, which is selected from 2-to-1 multiplexer 26. The two first ring electrodes also serve two functions as impedance output and biopotential reader, which are also controlled from another 2-to-1 multiplexer 26. Therefore, the 2-to-1 multiplexer's 26 input is connected to an electrode, and the two outputs are connected to the input of the 8-to-1 MUX 22 and the impedance measuring trace respectively. When biopotential reading is selected, the 2-to-1 MUX shorts electrodes to the impedance traces. A small signal is sent from the IMP_IN trace, travels to the nosecone electrode 5, measures the impedance of the contacting element, then travels out to the first ring electrodes 5 and outputs to the IMP_OUT trace as shown in FIG. 4B.

The cardiac biopotential signal is first picked up by electrodes 5, 6. These native signals enter the corresponding inputs of the 8-to-1 multiplexer 22. The multiplexer 22 outputs all eight inputs from electrodes 6 serially to the AC coupling circuit 23. Circuit 23 comprises of a capacitor and resistor in a low pass filter circuit topology, which truncates unwanted wandering baselines and DC offset voltages. The coupled signal is coupled to the instrumentation amplifier 24 with a gain of 200. The amplified signal is coupled to ADC 25 and digitizes the analog signal and then is processed by MCU 12 to converts the signal into a UART format communicated on wire TX 8.

Figure 6A:
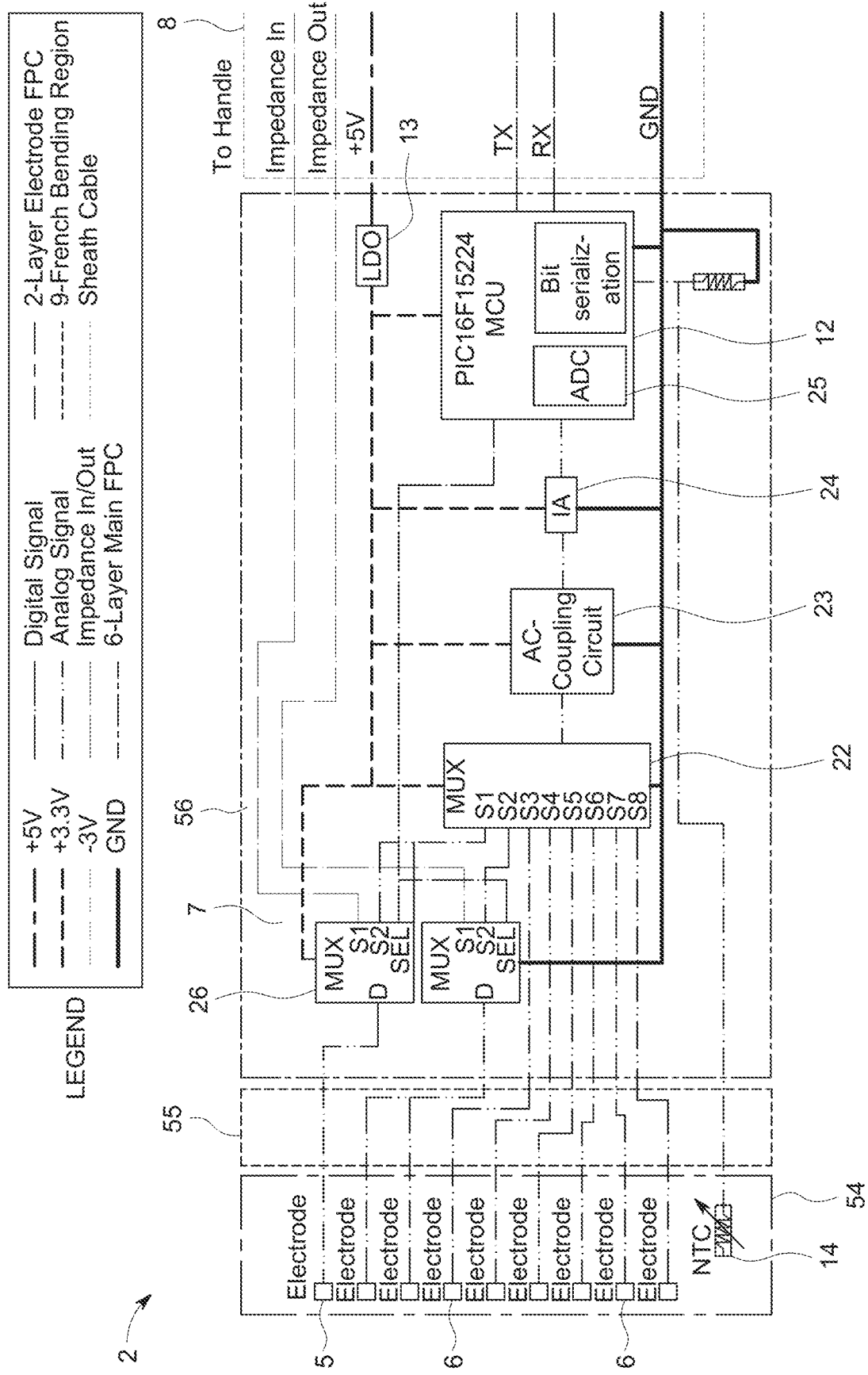
FIGS. 6A and 6B are electrical block diagrams of catheter tip of the electrical cable and optical embodiments respectively.

FIG. 6*a* is a schematic block diagram of another embodiment of Huygens catheter 1 with six electrical wires 8 coupling tip 2 to handle 4. The block diagram of tip 2 is divided into four dashed regions, an electrode region 54, a flexible bending region 55, an electronics region 56, and sheath electrical wires 8. Electrode region 54 includes eight half-ring electrodes 6, one nosecone electrode 5, and a negative temperature coefficient (NTC) thermocouple 14 to measure the temperature of the catheter tip 2. The bending region 55 does not include any electronic components, but only includes PB traces from the electrodes 5, 6 and NTC 14 to the MUX 22, 26. The electronic region 56 includes the rest of the electronic components such as the two 2-to-1

MUX's 26, the one 8-to-1 MUX 22, the AC-coupling circuit 23, instrumentation amplifier 24, the LDO's 13, and the microcontroller 12. The sheath region 3 includes the six electrical wires 8 which are designated impedance IMP IN & OUT, +5V, or VDD, ground, Tx, and Rx.

Figure 6B:
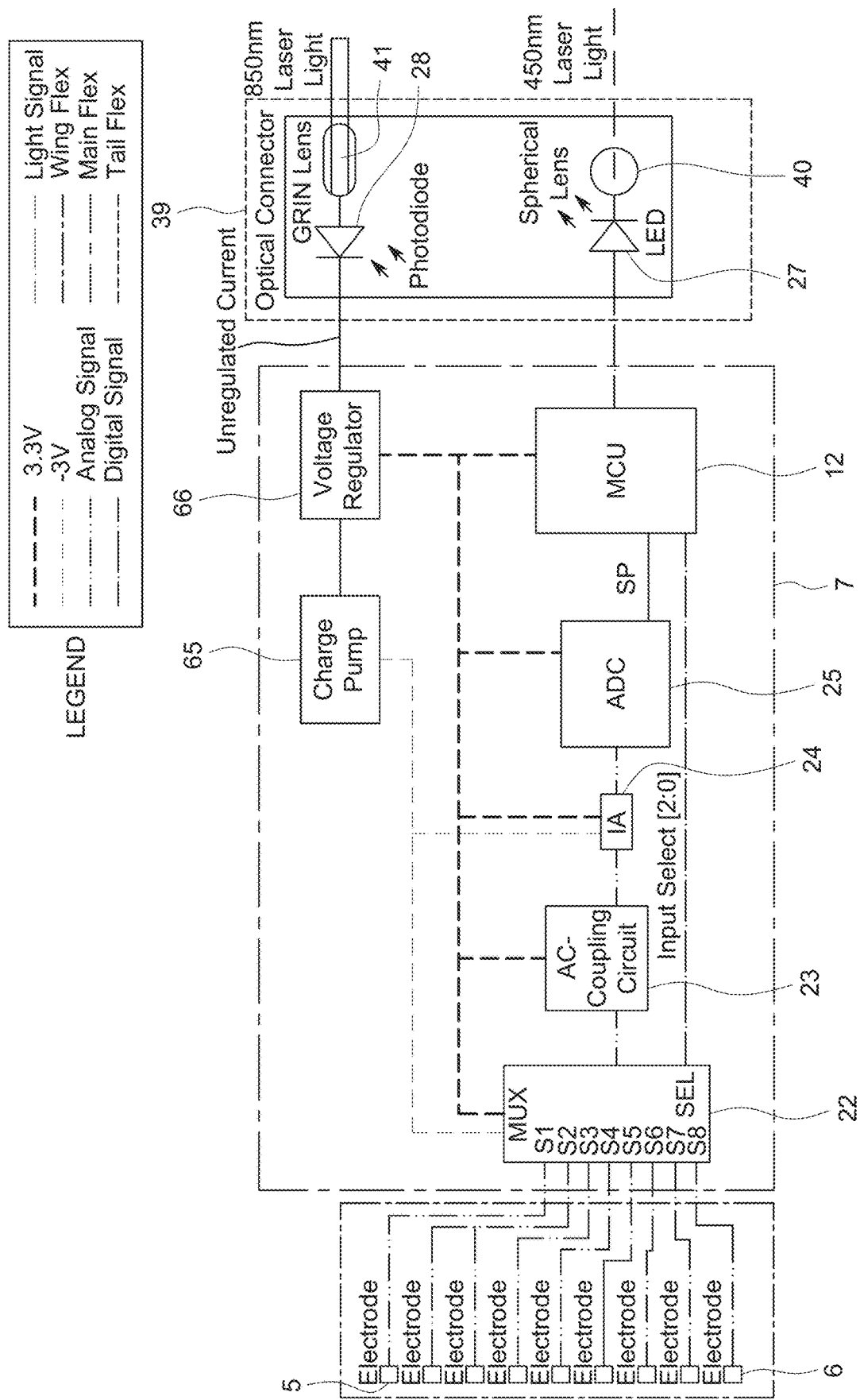
Figure 7:
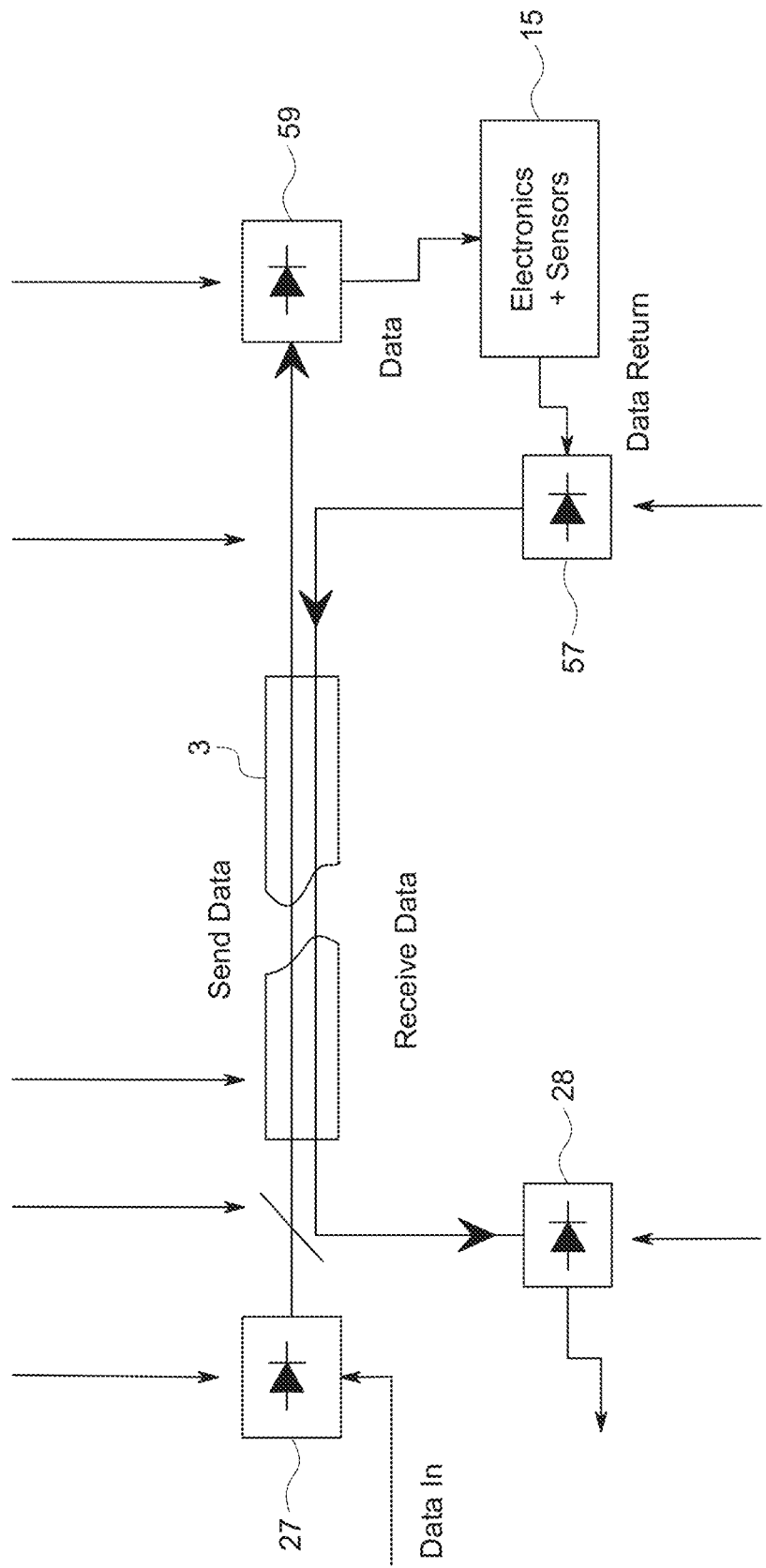
FIG. 7 is a diagram of the data flows in the optical embodiment of FIG. 6B between the catheter tip and the handle.

In the optical embodiment of FIG. 3A, the handle electronics 15 requires an optical receiver that retranslates the optical signals communicated on optical fiber 21 generated from the sensed data signals from tip electrodes 5, 6 back into corresponding electrical signals. The handle electronics 15 shown in FIG. 41 also requires a handle laser diode 57, diagrammatically shown in FIG. 3C, with minimum of 200 mW power that can supply a minimum of 20 mW power to the tip electronic board 7 at 850 nm. The 850 nm power from laser diode 57 is transmitted through dichroic mirror 58 optic fiber 21 to GRIN lens 41 in optical connector 39 of FIG. 25 coupled to tip FPC 7 and focused on photodiode 28 of FIG. 3C and FIG. 4A. The output of photodiode 28 is coupled to a voltage regulator 66 and then to a charge pump 65 as shown in FIG. 6*b* and then coupled to MUX 22, and IA 14. Laser 57 is included in this handle 4 as shown diagrammatically in FIG. 3C and it is controlled by a DSP 18. Laser 57 is coupled to laser driver circuit 123, controlled by DSP 18, and powered by 6V regulator 124. Regulator 124 in turn is powered by isolator 125. The 3.3V regulator at the handle 4 is supplying the microcontroller and amplifiers Through this laser power regulation, the tip electronics can receive more stable laser power.

Figure 41:
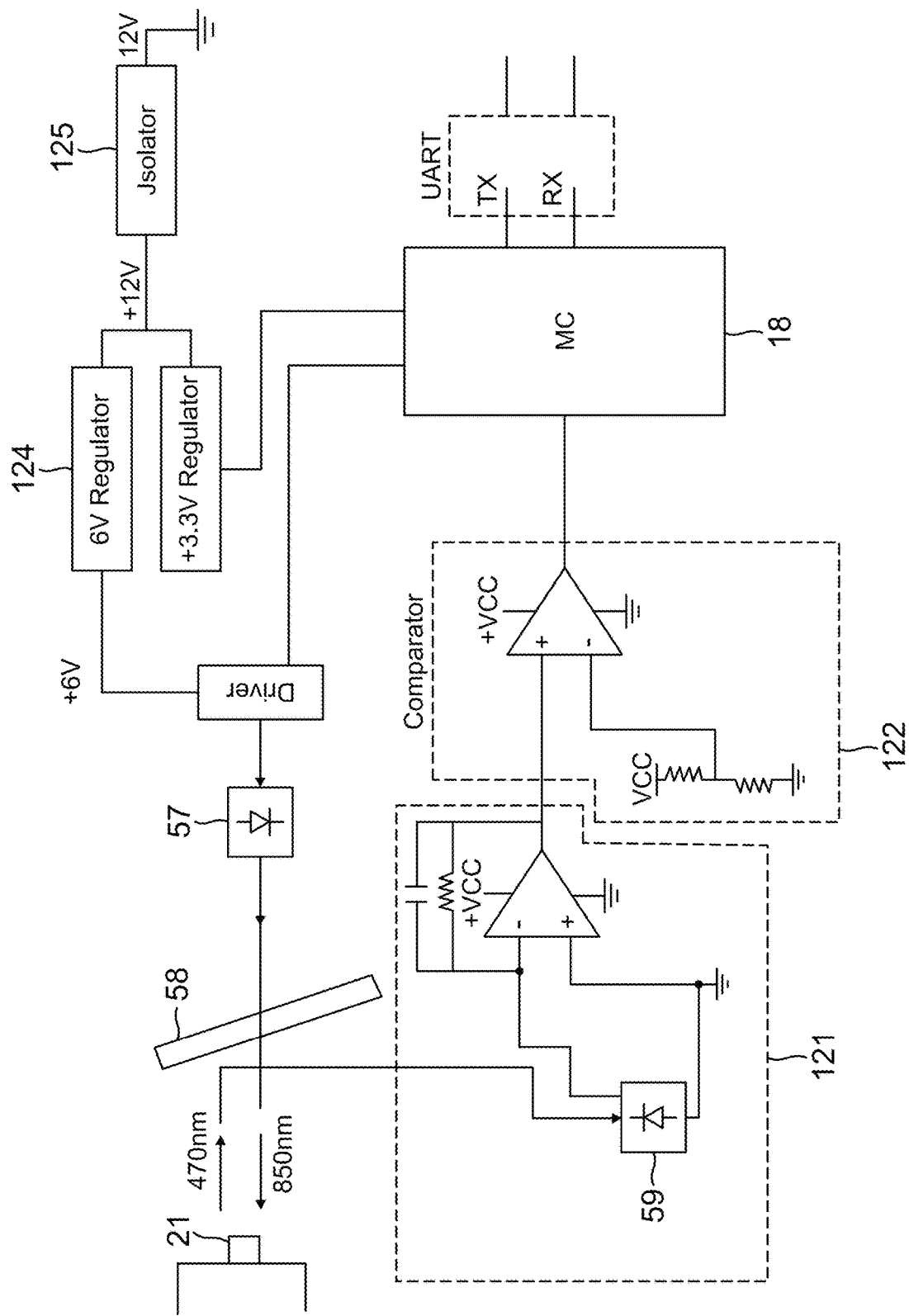
FIG. 41 is a block diagram of one embodiment of the handle electronics.

As shown diagrammatically in FIG. 3C bidirectional LED/photodiode 27 transmits and receives 415 nm optical data on fiber 21, which as shown in FIG. 41 is reflected in handle 4 by dichroic mirror 58 into photodiode 59, which provides a digital input to a transimpedance amplifier 121. The output of transimpedance amplifier 121 is input into a comparator circuit 122, whose output is a clean digital version of its input. The digital output of comparator 122 is provided as a data input microcontroller or DSP 18 and thence under program control to RX and TX inputs and outputs. The 450 nm LED signal from the tip electronic FPC 7 is transmitted through the single mode optical fiber 21 to the handle receiver circuit 15. As diagrammatically shown in FIG. 3C, handle dichroic mirror 58 filters the signal from the output laser 57. The filtered optical input signal is reflected into the photodiode 59 in the photo conductive mode to generate an electrical current output proportional to the received optical input. The current is input into transimpedance amplifier 60 that outputs corresponding voltage and a clean electrical digital signal is formed through a comparator circuit 69. This signal is then processed and interpreted through the DSP 18.

FIG. 6B is a block diagram of the embodiment of the catheter tip electronics with an optical interface. Optical connector 39 is comprised of 850 nm photodiode 28, 450 nm LED 27, a dichroic mirror 30, and two lenses 40, 41 for collimation. The optical connector 39 receives 850 nm laser light from the optical fiber 21, collimates it through the GRIN lens 41, and transmits it to photodiode 28. The photodiode 28 outputs a proportional electrical current which is coupled to a photovoltaic voltage regulator 29 to generate a stable 3.3V voltage. The 3.3V output of the photovoltaic voltage regulator 29 becomes the main voltage source that powers MUX 22, instrumentation amplifier (IA) 24, ADC 25, and MCU 12. Data sensed by electrodes 5, 6 are selected by MUX 22, which is controlled by MCU 12. These data are multiplexed through MUX 22 to AC coupling circuit 23, which functions to eliminate DC offset from the native signal in order to avoid clipping from the amplifier. The data signal is amplified by IA 24, converted to a digital signal by ADC 25, and provided as data output to MCU 12 in a form of serial peripheral interface (SPI) protocol. The digital data signal drives 450 nm LED 27, whose output is collimated through the spherical lens 40 and directed into optical fiber 21.

Electrical System Requirements

The system input frequency range of the catheter determines the filter spectrum and its specification.

TABLE 1

System Input Frequency Requirement

| Requirement | Values or Configuration | Comments |
| --- | --- | --- |
| EGM LF cutoff, $f_L$ | 30 Hz | 30 Hz rejects undesirable baseline wander in bipolar EGMs due to far-field LF signals. Fixed $f_L$ $1^{st}$ order HPF likely sufficient at catheter front-end. |
| EGM HF cutoff, $f_H$ | 500 Hz max. | Assume digitization rate of 1 kS/s/channel unless oversampling used. Overall roll-off above $f_H$ should be 18 dB/octave ($3^{rd}$ order filter) |
| EGM pass-band | Should be as flat as possible to preserve signal morphology | Butterworth filter characteristics |
| 60/50 Hz power line interference rejection | | 60/50 Hz is within the EGM pass-band and mainly common-mode. System depends on good CMRR. DSP 60/50 notch filtering provision needed, but commonly distorts signals of interest. |

The front-end amplifier ASIC 11 at the AC-coupling to the instrumentation amplifier IA 14 requires an electrical specification for safety and quality purposes.

TABLE 2

Amplifier Circuit Requirement

| Requirement | Values or Configuration | Comments |
| --- | --- | --- |
| Inputs | Differential | |
| Electrode-amplifier coupling | AC coupling (TBD) | AC coupling likely required to reject DC electrode overpotentials, but requires close coupling capacitor matching to preserve CMRR. See section 6.2. |
| Stage input impedance | ≥20 MΩ and well-matched | The higher the better. Hi-Z is required to minimize CMRR degradation due to electrode-tissue impedance difference. Must account for amplifier input bias current return path impedance. See section 6.1. |

TABLE 2-continued

Amplifier Circuit Requirement

| Requirement | Values or Configuration | Comments |
|---|---|---|
| EGM low amplitude detection | ≤30 µVpp required | The lower the better. |
| Amplifier Input-referenced noise | <5 uV desirable | The lower the better. |
| EGM max. signal level | 30 mVpp | |
| Differential AC max. signal level | Under investigation | Assume 50 to 100 mVpp at this time |
| Differential DC max. signal level | Up to ±200 mV | Due to platinum electrode polarization. Argues for input AC coupling. |

Each intracardiac electrogram (EGM) channel is digitized to a resolution that does not limit channel sensitivity. Table 3 shows the minimum resolution required for ADC 25 to detect the lowest input signal. Assume the gain of instrumentation amplifier 24 is 200, the minimum resolution required is 4 mV. Table 4 shows the voltage resolution of the least significant bit (LSB) of the ADC 25 at different numbers of bits. Assume the 10-bit ADC is used with reference voltage of 3.3V, the resolution of this ADC 25 is around 3.2 mV. Since the resolution of ADC 25 is below the minimum input voltage specification, 10-bit ADC 25 is accurate enough to be used in catheter tip system.

TABLE 3

Minimum Input Voltage Calculation

| Minimum Input Voltage [in uV] | Gain | Minimum Amplified Input Voltage [in mV] |
|---|---|---|
| 20 | 1 | 20 |
|  | 10 | 200 |
|  | 50 | 1000 |
|  | 100 | 2000 |
|  | 150 | 3000 |
|  | 200 | 4000 |
|  | 250 | 5000 |

TABLE 4

ADC Voltage per Bit Calculation

| ADC Ref Voltage [in V] | 10 | 12 | 14 | 16 | 18 | 20 | ADC Bits |
|---|---|---|---|---|---|---|---|
|  | 1024 | 4096 | 16384 | 65536 | 262144 | 1048576 | Bit Count |
| 3.3 | 3222.656 | 805.6641 | 201.416 | 50.354 | 12.5885 | 3.147125 | |
|  |  |  | Voltage per bits [uV/bit] |  |  |  |  |

Catheter Design Overview
Huygens Catheter

The Huygens catheter 1 comprises the tip 2, the sheath 3, the handle 4, and the robotic arm 1 as shown in FIG. 1. The catheter tip 2 amplifies and translates biopotential signal into a precise digitalized electrical (or optical) signal. The sheath 3 contains all the mechanical integrity to provide durability and flexibility that is required during diagnostic procedure. The sheath 3 functions as the bridge that transmits the digitalized signal from the tip to the handle 4. Finally, the handle 4 processes the digitalized signals by undergoing digital signal processing and sends them to the mapping station and personal computer. The Huygens catheter handle 4 has capability to be coupled with the robotic arm.
Catheter Tip The Huygens catheter tip 2 contains eight half-ring electrodes 6, one nosecone tip electrode 5, a flex printed circuit board (FPC) 7, and six holes 62 for electrical wire connector as shown in FIGS. 3A and 3B. If the catheter uses an optical system, then the tip additionally contains optical connector 39 . . . . Initially, the catheter tip diameter is 11 French (3.67 mm) or less and 82 mm long. The tip FPC 7 is a six-layer board with thickness of 0.34 mm and bend radius of 8.1 mm. Each of the nine electrodes 5 and 6 are connected to the assigned MUX 22 inputs that will be processed through the tip electronic circuits.

Figure 14:
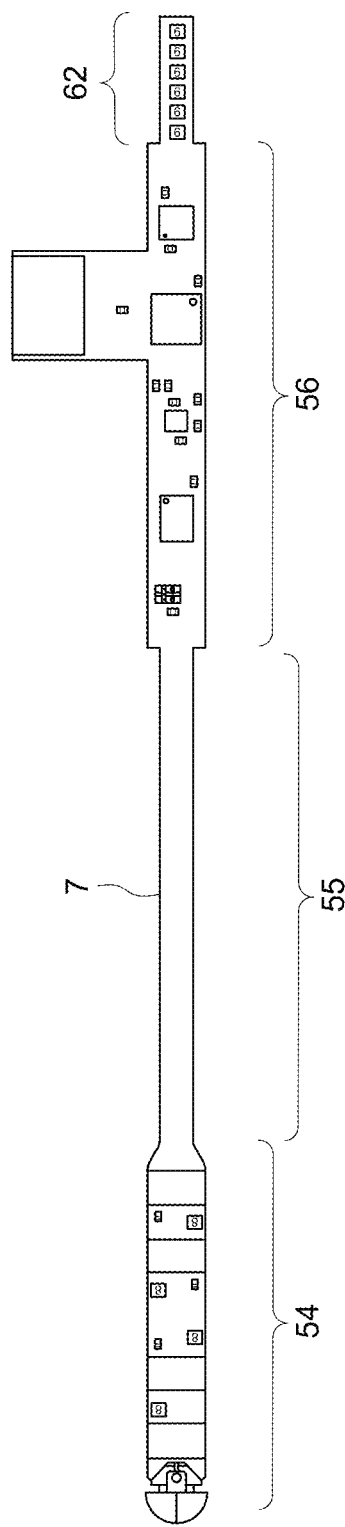
FIG. 14 is a top elevational view of the tip flex printed circuit (FPC) of FIG. 13.
Figure 16:
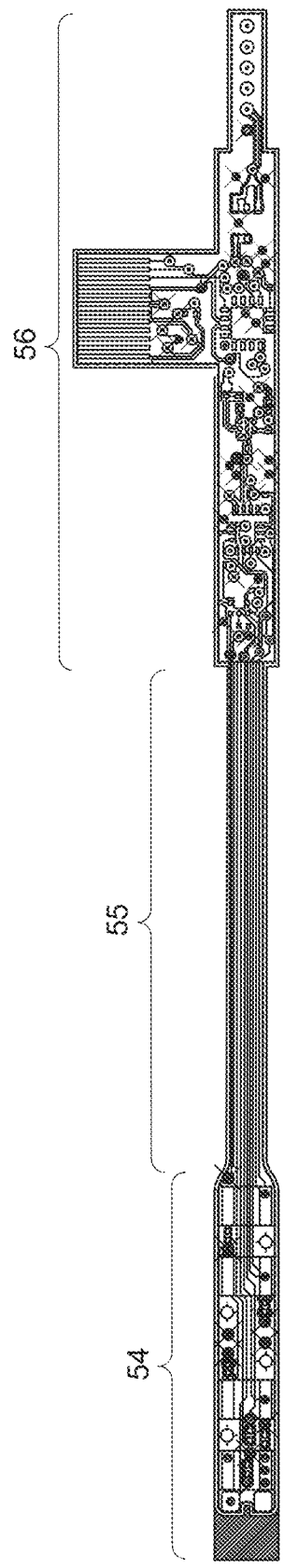
FIG. 16 is the top plan view of the entire catheter tip flex printed circuit board layout.

Tip flex printed circuit board (FPC) 7 is 82 mm long and 3.4 mm wide to fit in a 11 French system. The FPC 7 is divided into three sections, electrode region 54, bending region 55, and electronic region 56. As shown in FIG. 14, the electrode region 54 covers from the most distal tip and it is 23 mm long, followed by 29 mm of bending region 55. Finally, the last 30 mm of FPC is electronic region 56 with a small tail that contains six vias 62 for the electrical wire connection from the sheath 3.

Figure 8:
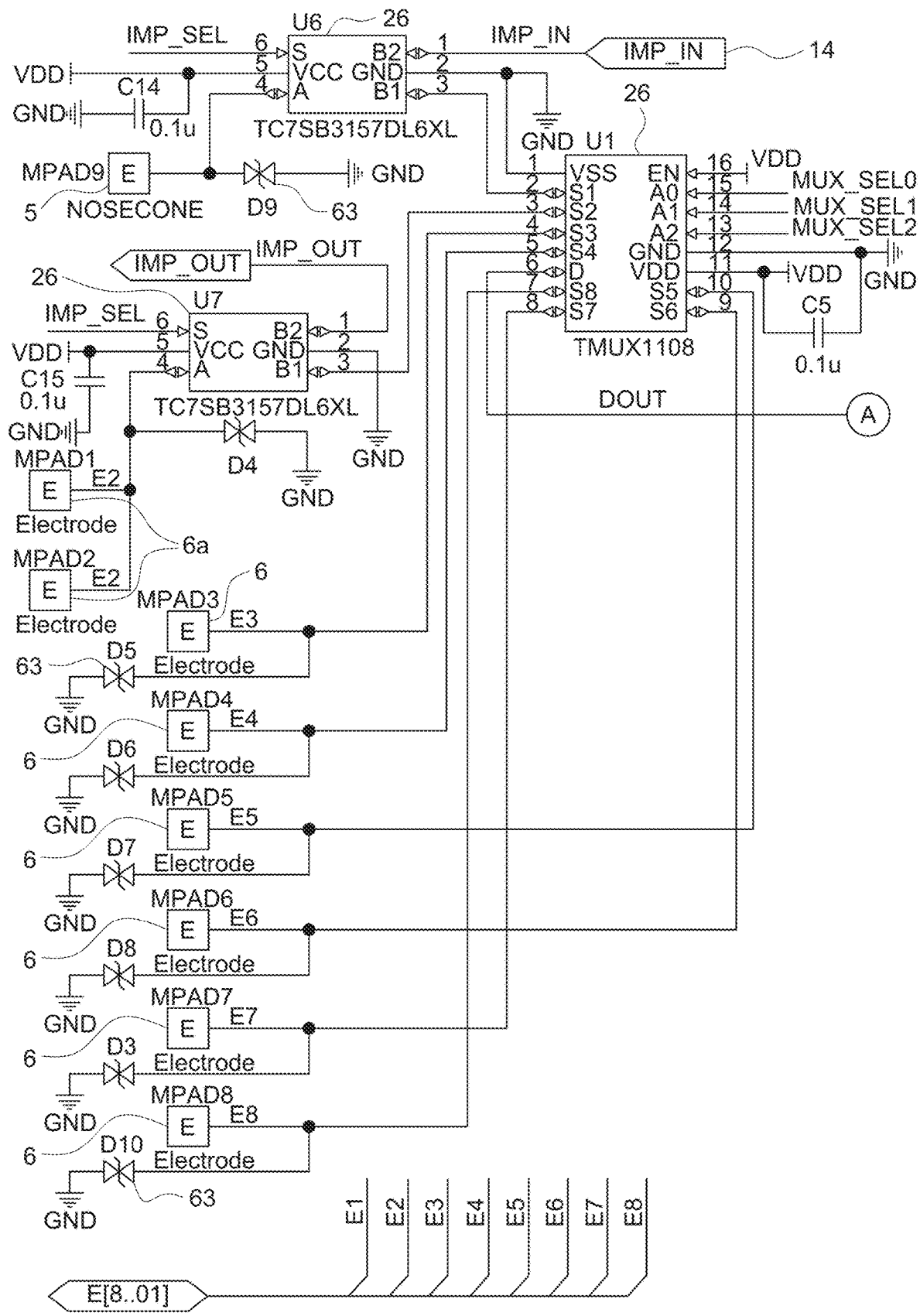
FIG. 8 is an electrical schematic of the multiplexer control of the catheter tip in the electrical cable embodiment of FIG. 6A.
Figure 8:
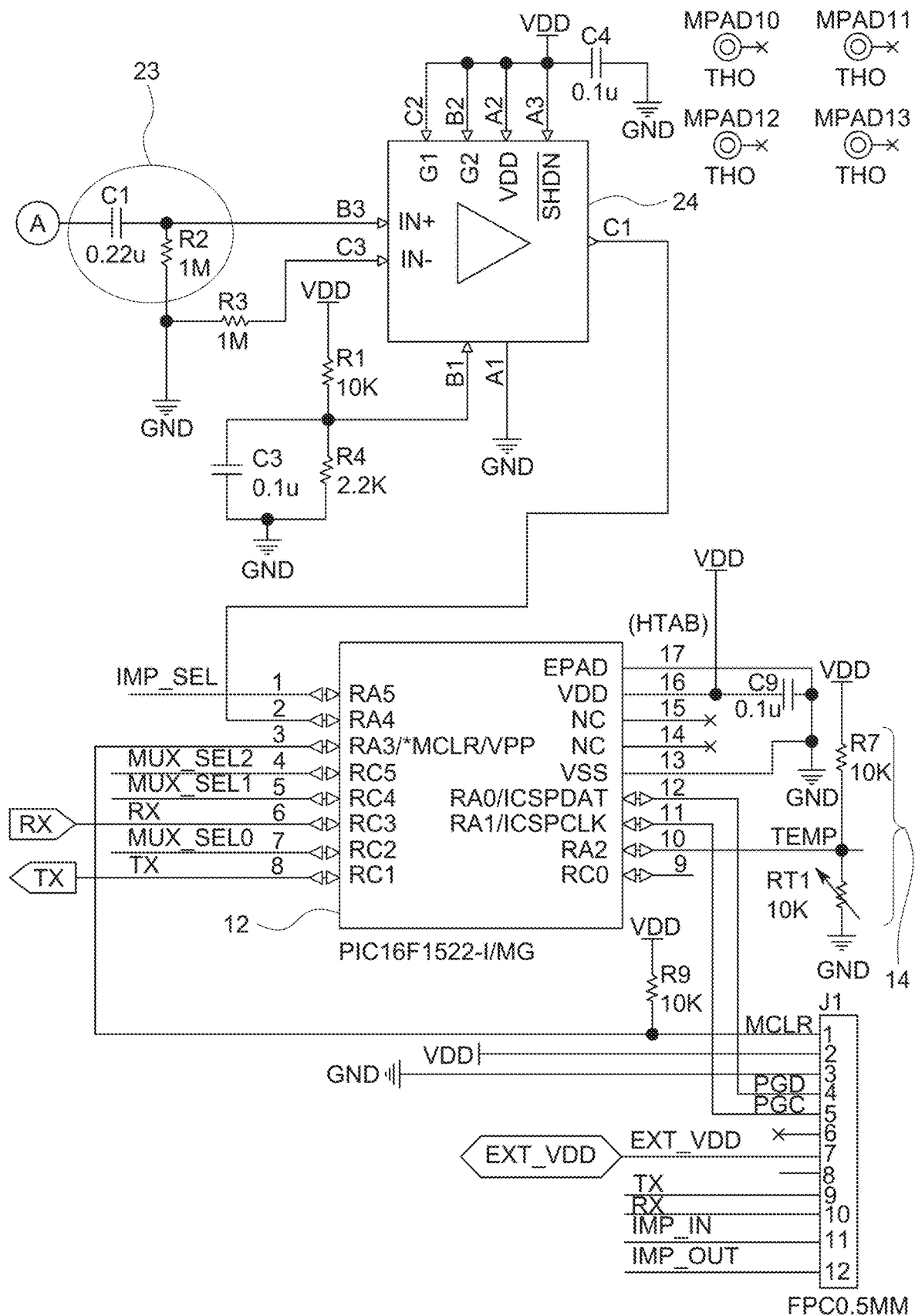
Figure 17A:
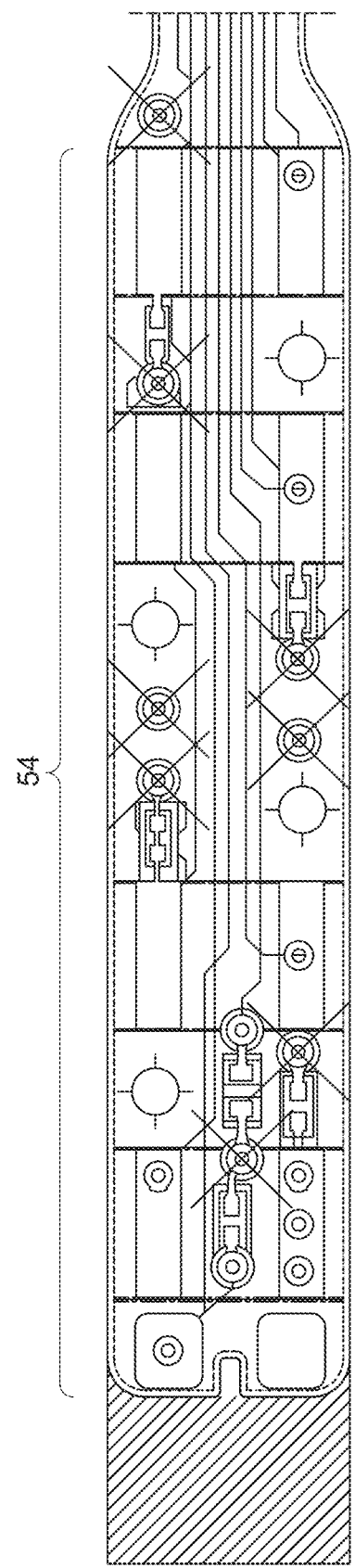
FIGS. 17A, 17B, and 17C are diagrams showing the layout of the three regions of tip FPC of FIG. 16, namely the electrode region, bending region, and electronic region respectively.

Electrode region 54 as shown in FIG. 17A is the most distal region of FPC 7 that contains all nine electrodes (eight half-ring 6 and one nosecone 5). In the illustrated embodiment FPC 7 is a six layer printed circuit board, namely six layers of copper with intertying insulating layers. FIGS. 16, 17A-17C are top views in which all six layers are visible through the overlying layers. To provide more flexibility, the copper pour on top and bottom layers of FPC 7 are removed. Also, to protect copper traces from bending, all the electrode signal traces run on the inner layers. Next to each electrode, there is corresponding transient voltage suppression (TVS) diode 63 shown in FIG. 8 to protect the traces and electronic components from damage due to possible over voltage/over current from the patient body. The electrode region 54 also includes NTC thermistor 14 to measure the temperature of the patient body for safety purposes.

Figure 17B:
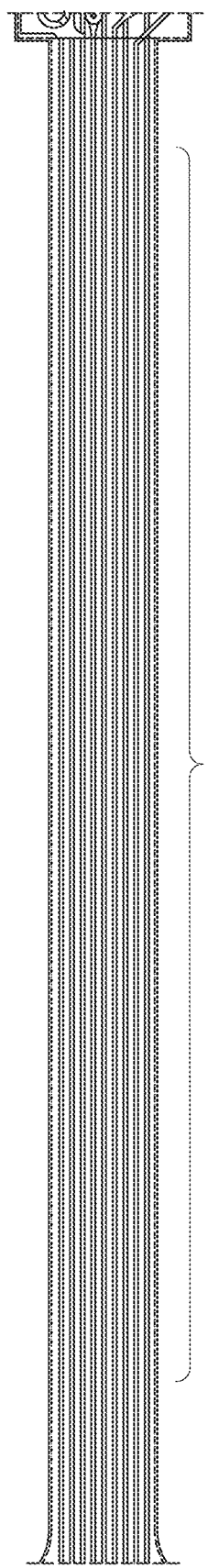

FIG. 17B shows the bend region 55, where most of the tip deflection occurs. Therefore, this region contains no copper pour as well as no electronic components. Bend region only contains nine traces from the electrodes on the inner layer. In order to provide most bending in this region 55, the width of this region is 2.0 mm compared to 3.4 mm width on the other two regions 54 and 56.

Figure 17C:
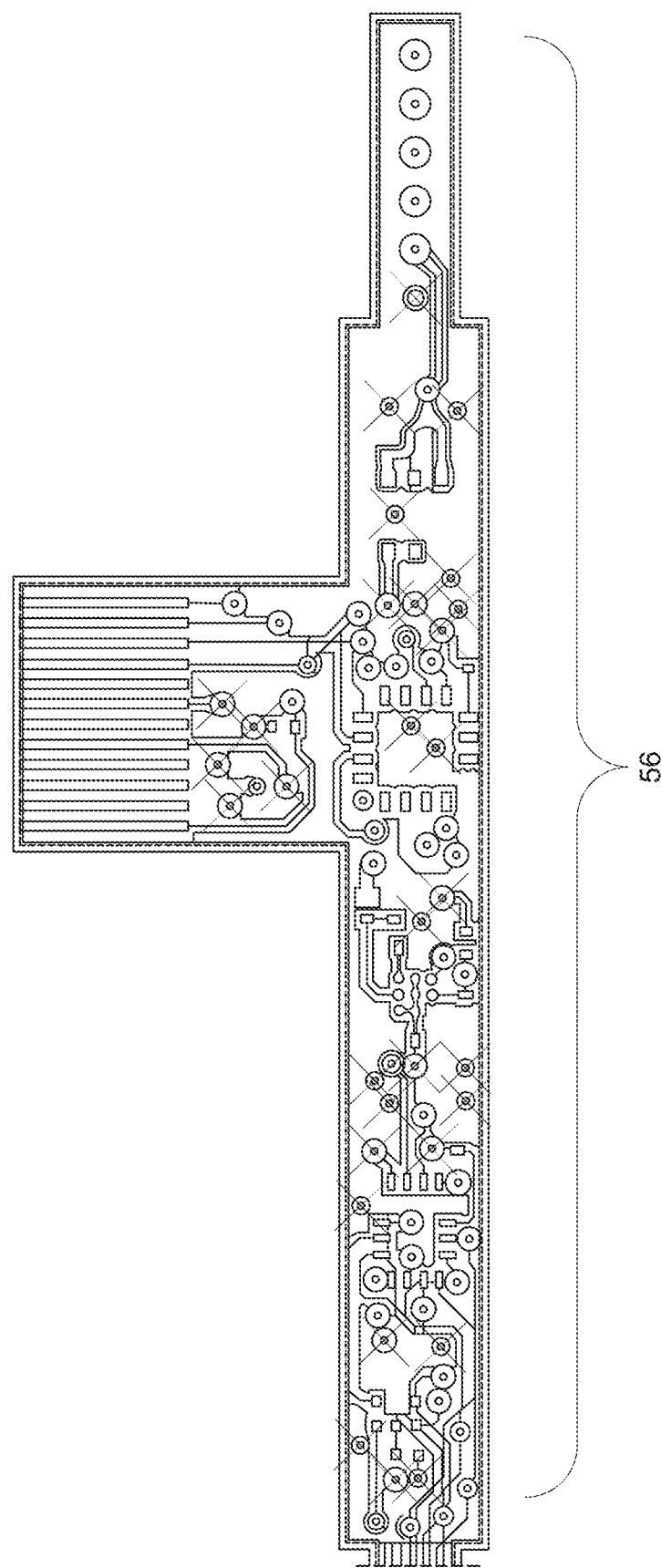
Figure 18:
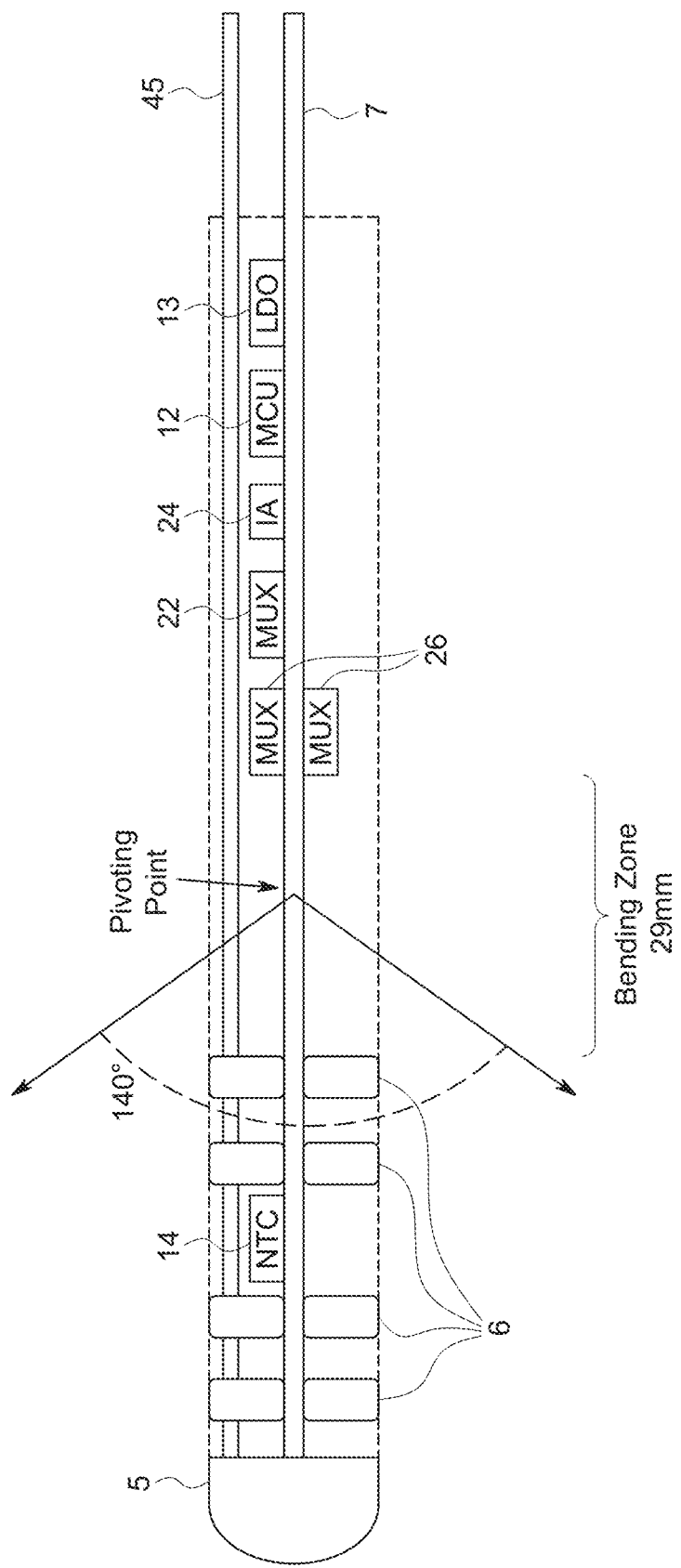
FIG. 18 is a transparent side view of the block diagram of the catheter tip and its mechanical flexure as well as its functional requirements.

The electronic region 56, shown in FIG. 17C, includes all the electronic components required to perform amplification, digitization, and serialization, as well as electrical to optical conversion if the catheter contains optical system as shown in FIG. 4A and FIG. 4B. These components include 8-to-1 MUX 22, 2-to-1 MUX 26, instrumentation amplifier 24, analog to digital converter 25, LDO 13, and microcontroller 12. To provide stable grounding, the top and bottom layer of the board is copper poured to ground. Due to the 11 Fr limitation, the height of the components on this region must not exceed 1.5 mm (1.5 mm+0.34 mm+1.5 mm=3.34 mm).

Figure 13:
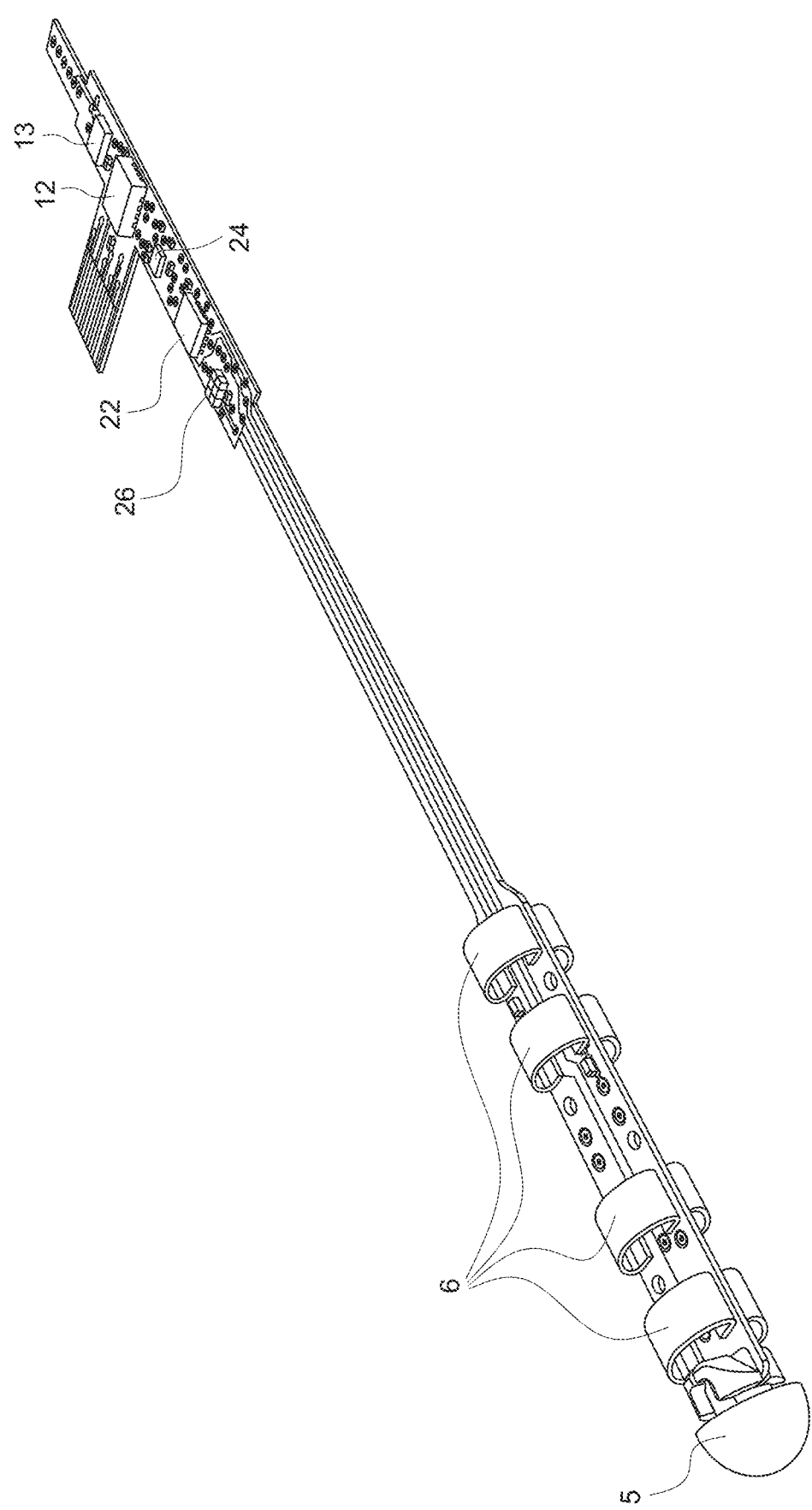
FIG. 13 a perspective view of the tip FPC with the electronics assembled thereon.

As best seen in FIG. 13, Huygens catheter 1 is designed to be quadripolar (4 electrode rings), with two half-ring electrodes 6 per ring and a nosecone tip electrode 5, totaling nine electrodes reading biopotentials. Each ring 6 is divided into top and bottom portions respectively to precisely locate and isolate the tissue wall from the blood. Each electrode 5 and 6 can perform a unipolar reading, or it can combine with adjacent electrode to perform bipolar readings. The catheter 1 is limited to eight electrodes 6 due to the maximum input in a single multiplexer 22. Any additional electrode will require extra MUX capacity which is not recommended in the confined dimension.

Nosecone Tip Electrode

Figure 19:
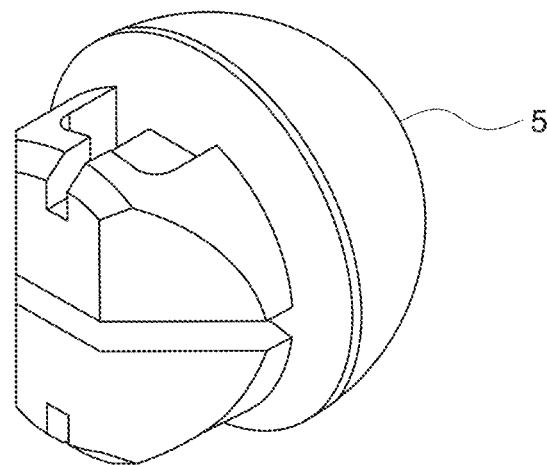
FIG. 19 a perspective view of the tip nosecone electrode.
Figure 20A:
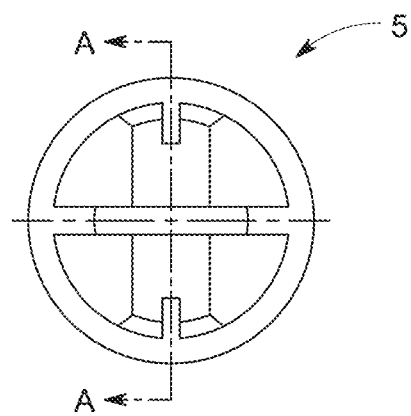
FIGS. 20*a*, 20*b* and 20*c* are three views showing the mechanical dimension of the tip nosecone electrode.
Figure 20B:
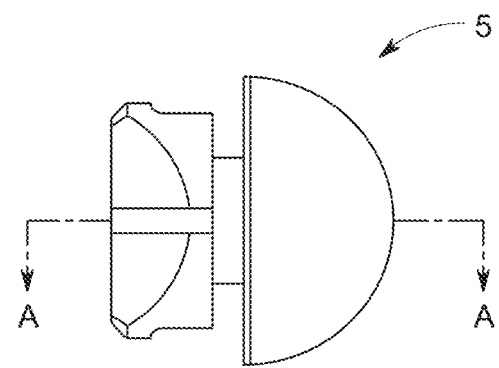
Figure 20C:
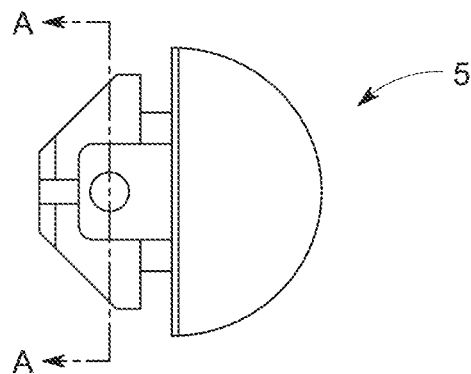

FIG. 19 is a perspective view of the tip electrode 5, which is the most essential element that the physician needs during diagnostic operation. This electrode 5 is coupled to the first input of the amplifier MUX 22 and connected to the impedance measuring MUX 26 in FIG. 4B. Therefore, nosecone tip 5 can function as the biopotential reader or an impedance measuring tool depending on the switch bits from the microcontroller 12.

Ring Electrode

Figure 22:
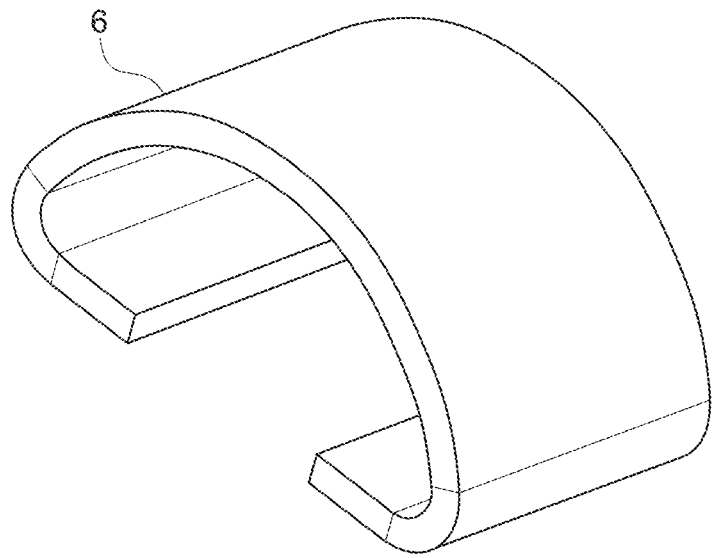
FIG. 22 is a perspective view of a half-ring electrode.
Figure 23:
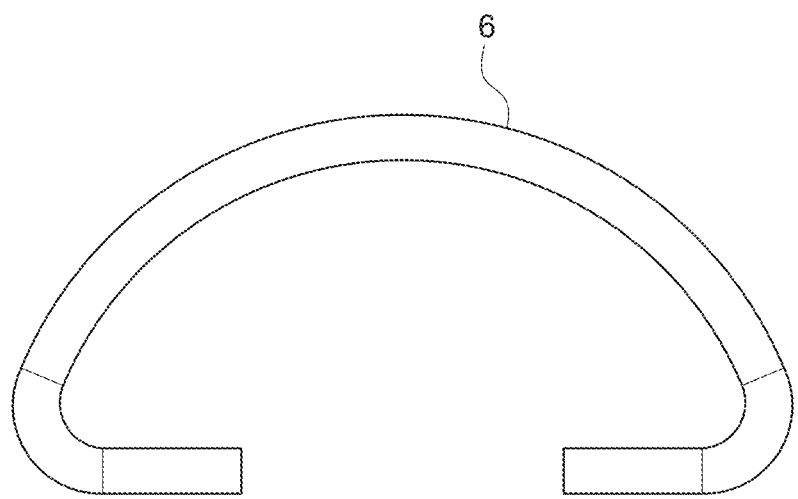
FIG. 23 is a side cross sectional view showing the mechanical dimension of the half-ring electrode of FIG. 22.

FIG. 22 is a three dimensional view of a half-ring electrode 6. This electrode is mounted both top and bottom side of the electrode region 54 of tip FPC 7. Each half-ring band 6 is coupled to an independent MUX 22 input, except for the first ring band, where both top and bottom bands 6 are connected to the same second input of MUX 22. This is due to the nosecone electrode 5 being the $1^{st}$ input, and since it requires a bipolar pair, both electrodes on the $1^{st}$ ring band needed to be connected to the same MUX 22 input. The first ring band 6 is also connected to impedance MUX 26 where the electrode 6 can function both as a biopotential reader or as an impedance measuring tool. For bipolar measuring feature, there is a big gap between the second and third ring, and the rest of the rings are closely placed as shown in FIG. 14. The first and second ring can be a bipolar pair, as well as third and fourth ring.

Safety Wire

Figure 21:
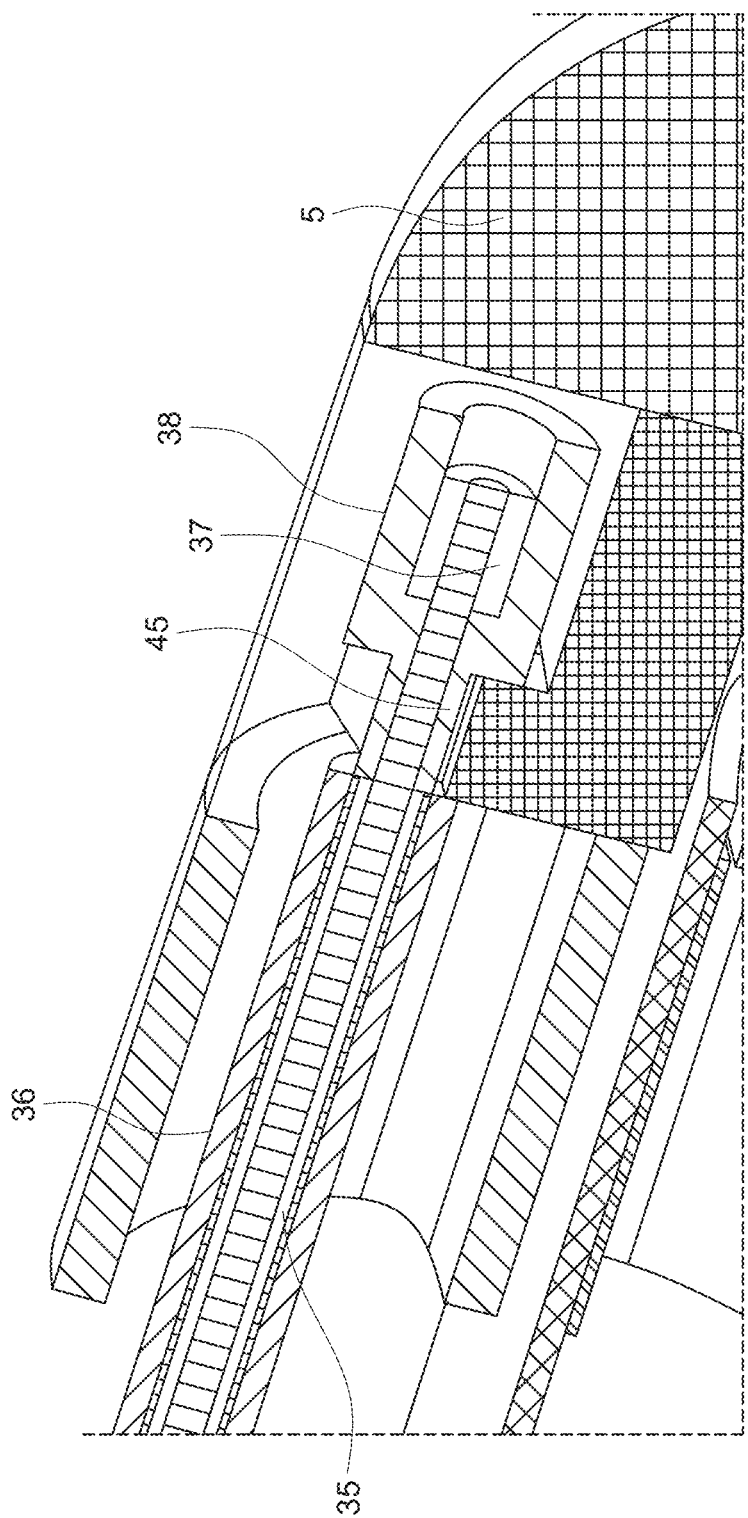
FIG. 21 is a cutaway side cross sectional diagram showing how the safety wire is inserted into the nosecone electrode, while electrically isolated thereform.

Safety wire 9 is a wire that is connected from the center lumen of the sheath 3 to the nosecone tip 5. It ensures that no components are left in the body when the catheter 1 is pulled out. This part requires high durability and very secure connection with the nosecone electrode 5 as shown in FIG. 21. It is electrically isolated to prevent from creating an antennae effect. In order to achieve electrical isolation, the tip of the pull wire 45 with a hypotube 37 is covered with a polyetheretherketone (PEEK) insulator 38.

Tip Electronics

Multiplexer (MUX)

There are two types of multiplexers in the catheter tip system, an 8-to-1 MUX 22 and 2-to-1 MUX 26. The 8-to-1 multiplexer 22 in FIG. 4A is an eight-input, single-output, low-powered multiplexer. Each electrode 5, 6 is connected to a corresponding MUX input. In order to provide high resolution at the output stage of the catheter 1, the MUX 22, 26 is continuously switching at a rate of 10K samples per second. Multiplexers 22, 26 have the smallest dimension that can fit inside a catheter, namely 2.6 mm×1.8 mm×0.5 mm.

The 2-to-1 MUX 26 is a two-input single output multiplexor that is connected to the nosecone electrode 5 and the first band of the half-ring electrodes 6. This multiplexor 26 selects the function of the connected electrode either as a biopotential reader or impedance reader through the control of the microcontroller 12.

Instrumentation Amplifier (IA)

Figure 10:
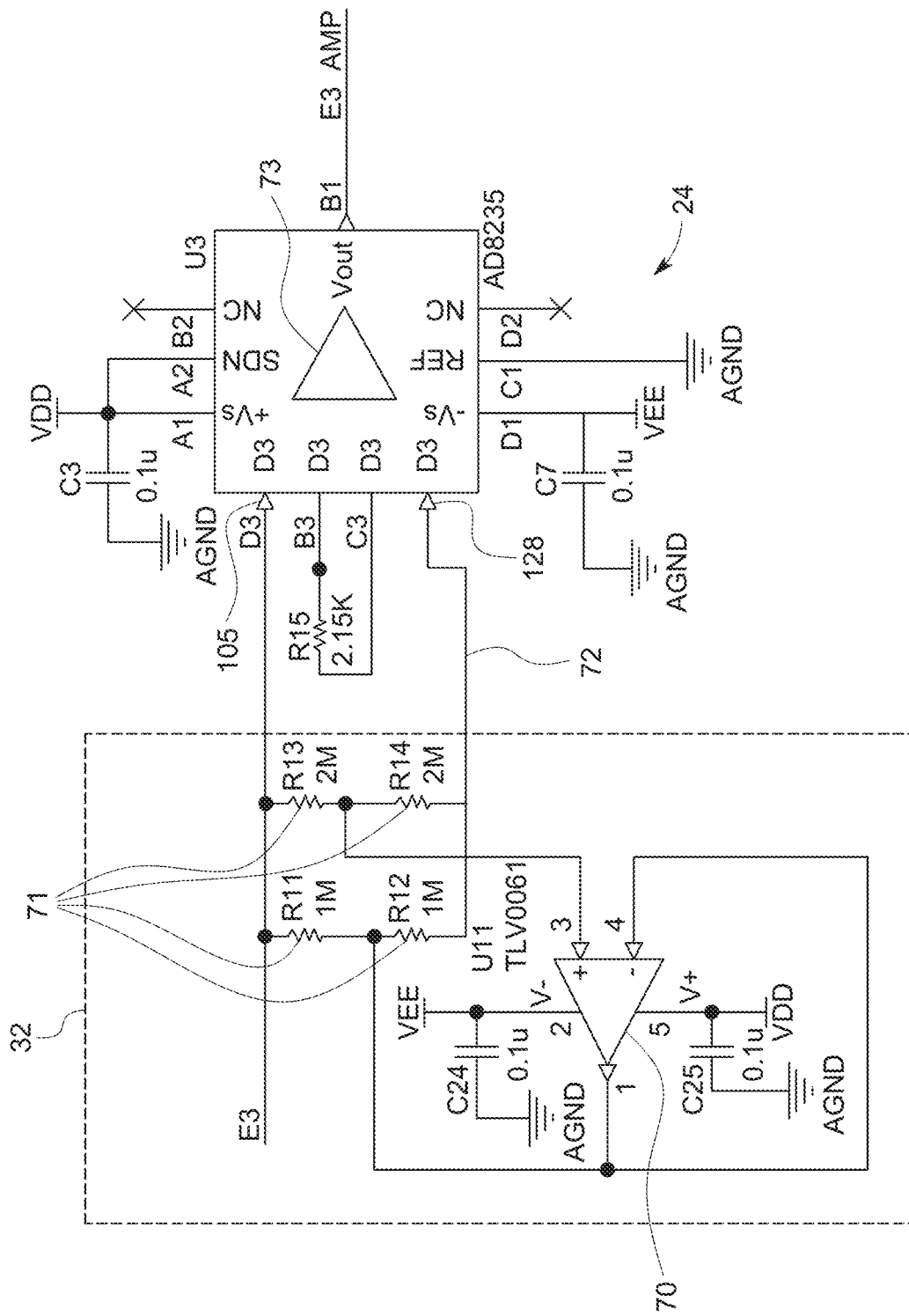
FIG. 10 is a schematic diagram of a first embodiment of the AC-coupling circuit and instrumentation amplifier.
Figure 11:
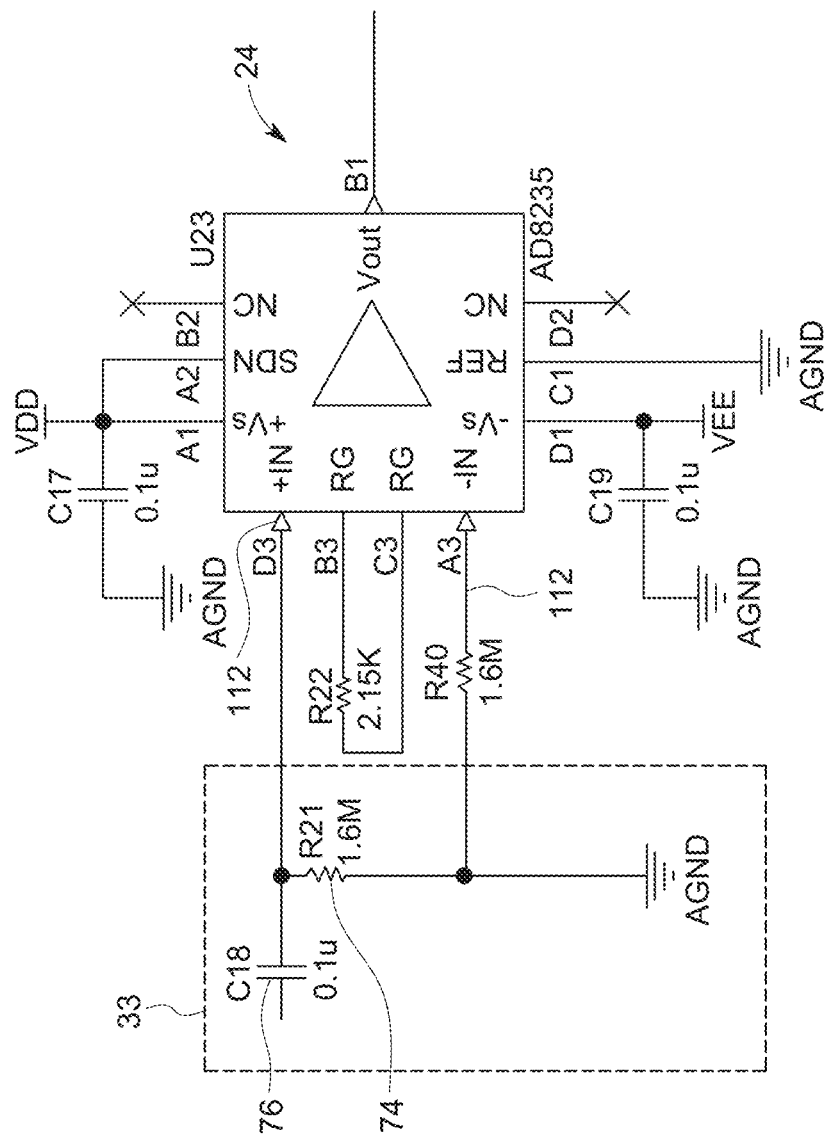
FIG. 11 is a schematic diagram of a second embodiment of the AC-coupling circuit and instrumentation amplifier.
Figure 12:
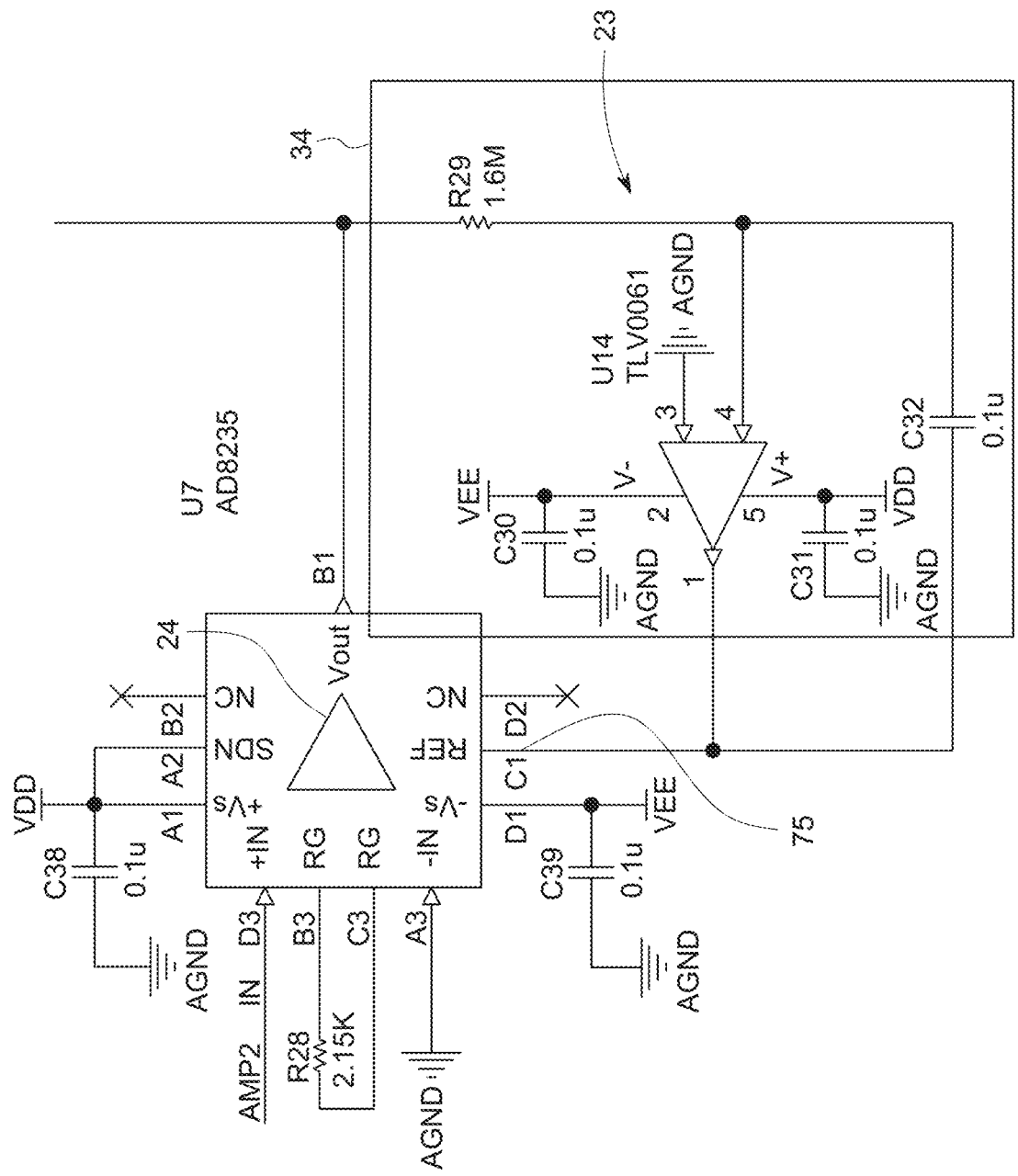
FIG. 12 is a schematic diagram of a third embodiment of the AC coupling circuit and instrumentation amplifier.

The instrumentation amplifier (IA) 24 in FIG. 4A and better shown the schematics of FIGS. 10-12 is a 65 µA low-power instrumentation amplifier 24. With high input impedance, it can achieve up to 130 dB of common mode rejection ratio (CMRR). The gain can be physically programmed by the two gain pins G1, G2, and by connecting both gain pins to VDD, the amplifier is set to have the gain factor of 200. The differential input of IA 24 includes a capacitor-resistor circuit that functions as an AC-coupling circuit 23. This amplifier 24 is one of the smallest IA 24 in the market with dimension of 1.26 mm×1.23 mm×0.6 mm.

Instrumentation amplifier 24 must have an AC-coupling circuit 23 to remove the DC offset voltage. Three different AC-coupling techniques were presented as shown in FIGS. 10, 11, and 12. FIG. 10 shows a capacitor-resistor circuit 32 that includes an active op amp 70. This circuit 32 not only has AC-coupling effect, but also provides high common mode rejection ratio (CMRR) and electrode to electronics isolation. The CMRR value is directly proportional to the input impedance of the amplifier 70. Since the resistors 71 are connected to the inputs 72 of another op-amp 73, the input impedance of IA 24 is maintained, which preserved the high CMRR value.

The IA 24 of the embodiment of FIG. 11 uses a common high-pass filter with a simple capacitor-resistor circuit 33. Since the input resistor 74 is in parallel with the IA 24 inputs, the equivalent input impedance will be reduced, which leads to lower CMRR.

Another embodiment shown in FIG. 12 has an AC-coupling circuit 23 option located at the output of an IA 24. Output of the op-amp 24 is communicated to the reference pin 75 of the IA 24, which regulates the voltage level.

From the theoretical assessment, the first IA embodiment 32 of FIG. 10 yields the best result by providing AC-coupling, high CMRR, and electronic isolation to electrodes. However, an extra Op-Amp, four resistors and two capacitors might cause a space issue in FPC 7. The second embodiment 33 in FIG. 11 will be most promising in its simplicity, but the low CMRR must be carefully examined.

The resistance and capacitance of the AC coupling circuit 33 of FIG. 11 is determined by the following equation:

$$F_c = 1/(2\pi RC)$$

Where $F_c$ is the high-pass cutoff frequency, and R 74 and C 76 are the corresponding resistance and capacitance values. Solving for $F_c=1$ Hz and R=1 MΩ, we get capacitance of $C = 1/(2\pi R F_c) = 1/(2\pi(1\times10^6)(1)) = 159$ nF. Instead of 159 nF capacitance a more standard value of 220 nF is chosen. Redoing the calculation with a 220 nF capacitance and 1 MΩ resistance, a cutoff frequency of 0.72 Hz is obtained.

Analog to Digital Converter (ADC)

The ADC 25 in FIG. 4A is an 18-bit, pseudo-differential successive approximation register (SAR) ADC 25. Input voltage of 3.3V is connected to the reference pin, which defines the resolution of this ADC 25 as $$\frac{3.3 V}{2^{10} \text{ bit}} = \frac{3.3}{262144} = 12.5 \times 10^{-6} = 12.5 \mu V \text{ per bit}.$$

The digitized data is transmitted to the MCU 12 in a 3-wire serial peripheral interface (SPI). This device has a dimension of 3 mm×3 mm×0.75 mm.

Due to the spatial constraint, an internal ADC included in microcontroller 12 can be used. This internal ADC from MCU (PIC16F15224) has a 10-bit with reference voltage of 3.3V. This resolution can still meet a required specification of biopotential resolution.

Low Dropout Voltage Regulator (LDO)

Figure 9:
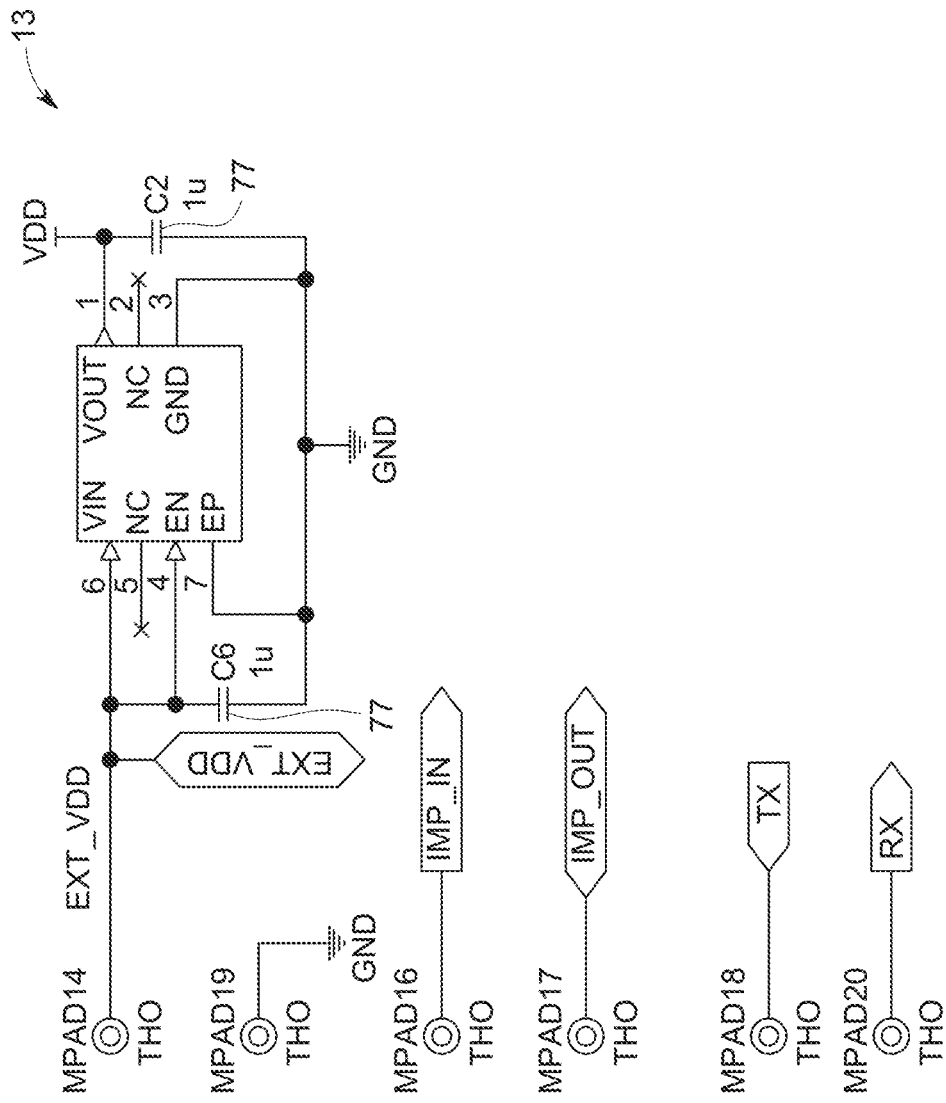
FIG. 9 is a schematic of the connection from the six electrical wires from the sheath to the tip FPC in the electrical cable embodiment of FIG. 6B.

FIG. 4B shows low dropout voltage regulator 13 that feeds in the external voltage from the handle 4 and regulates it to a useable 3.3V supply for the entire tip electronics. FIG. 9 shows a schematic form of the LDO 13. Each output and input are connected to a 1 uF capacitor 77 for ripple reduction, and additional LC filter 31 is required for more stable voltage supply.

Microcontroller (MCU)

The microcontroller 12 in FIG. 4B is a 16-bit, low-powered, PIC microcontroller 12 that has a dimension of 3 mm×3 mm×0.9 mm. This component controls the sampling rate of MUXs 22 and 26. It also contains an internal ADC that can digitize the amplified biopotential signal. PIC16 microcontroller 12 processes the digitized biopotential data and NTC thermistor 14 output to a universal asynchronous receiver-transmitter (UART) format and outputs it to the handle 4. If the catheter 1 contains optical system as shown in FIG. 3A, the UART output is coupled to LED 27 to convert the digitized data to an optical data signal.

Step-Up DC/DC Voltage Regulator

LTC3105, a step-up DC/DC converter 29 shown in FIG. 4A is used for light energy harvesting application. The parallel resistor network of 1 MΩ and 2.2 MΩ resistors regulate the output voltage to be 3.3V. This device contains a MPPC pin that maximizes power generation in I-V curve. The input pin is connected to the photodiode 28, which generates an electrical current proportional to the photonic power received. This device has a dimension of 3 mm×3 mm×0.75 mm.

Optical System

Optical Connector

Figure 24A:
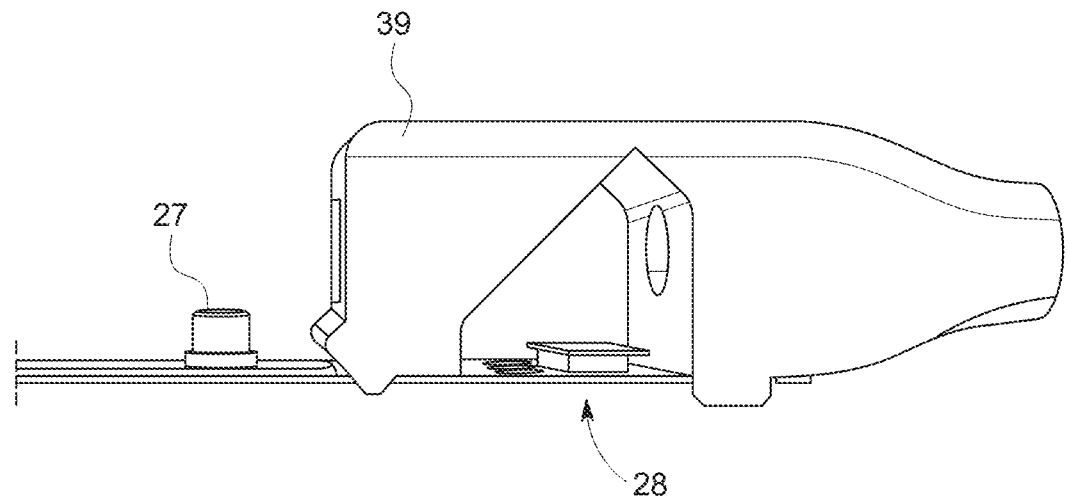
FIG. 24A is a side perspective side view showing an optical connector couple to the tip FPC at its flat orientation.
Figure 24B:
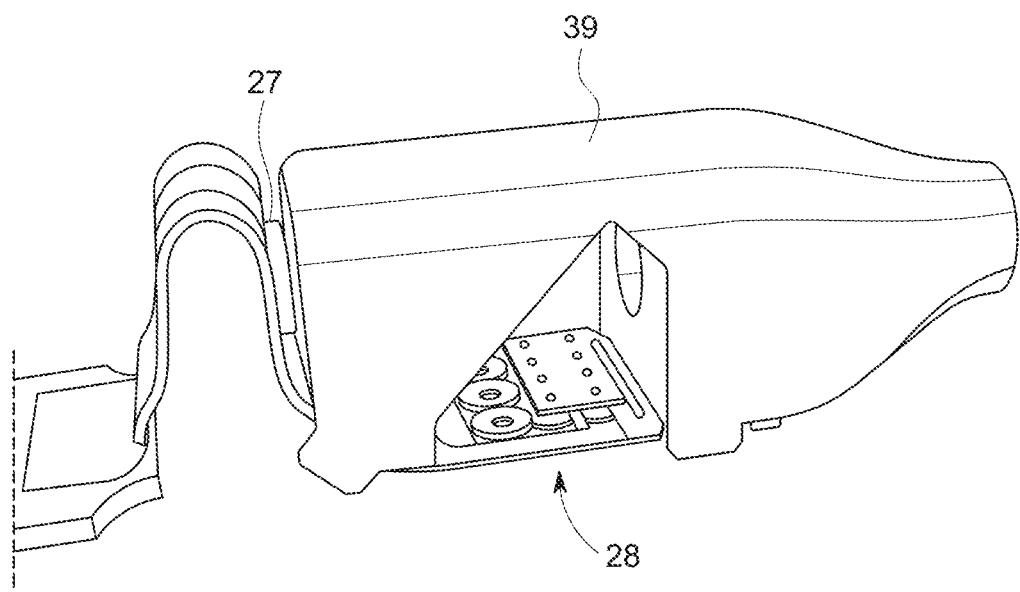
FIG. 24B is a side perspective view showing when the FPC is fully bent.
Figure 25:
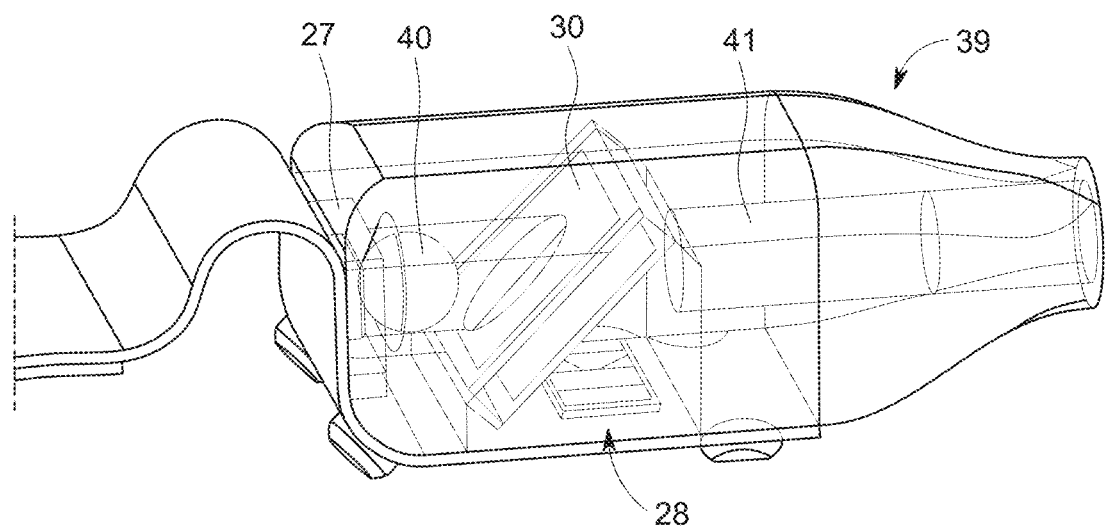
FIG. 25 is a perspective phantom view of the optical connector of FIGS. 24A and 24B shown after the FPC is bent.

A mechanical optical connector 39 shown in two views in FIGS. 24A and 24B connects optical fiber 21 from the sheath 3 to the optical system at the catheter tip 2. It is mounted at the distal end of main FPC 7. The main purpose of the optical connector 39 is to precisely align GRIN lens 41, dichroic mirror 30, LED 27, laser and photodiode 28 to minimize the photonic power loss. The four legs of the connector secure the FPC 7 bending angle to be consistent as shown in FIG. 25. The back surface of the connector 39 has a pressure sensitive adhesive (PSA) and attaches to the tail FPC 7.

Photodiode

FIG. 25 shows four arrays of photodiodes 28 in parallel to detect the 850 nm laser light from the handle 4. The design input of photodiode array 28 requires a large active area to capture as much light energy as possible. Array 28 can achieve the design requirement with a component dimension of 2 mm×1 mm but total active area of 1.71 mm². This data gives the percentage of active area on the surface of the photodiode 28:

$$\% \text{ of Active Area} = \frac{1.71 \text{mm}^2}{2 \text{mm} \times 1 \text{mm}} \times 100 = 85.5\%$$

The purpose of photodiode array 28 is to provide electrical power to the tip electronics. Therefore, the photodiode array 28 needs to be in zero-biased configuration to operate in the photovoltaic mode.

470 nm LED

LED 27 is 470 nm InGaN LED 27 that transmits the optical signal to the catheter handle 4. One of the design requirements for tip electronics is to minimize the power, so an LED 27 with low power consumption is selected. This LED 27 operates at a forward voltage of 2.65V and 2 mA current. The total power consumption is 2.65V×2 mA=5.3 mW. Another design requirement of the LED 27 is to provide maximum light intensity to the handle 4 in order to minimize the signal distortion. LED 27 can emit 45 millicandela of luminous intensity at a view angle of 100°. To transmit most of the light through the optical fiber 21, a spherical micro lens 40 in FIG. 25 is attached directly on top of the LED 27 to collimate the dispersing light.

Dichroic Mirror

Figure 26:
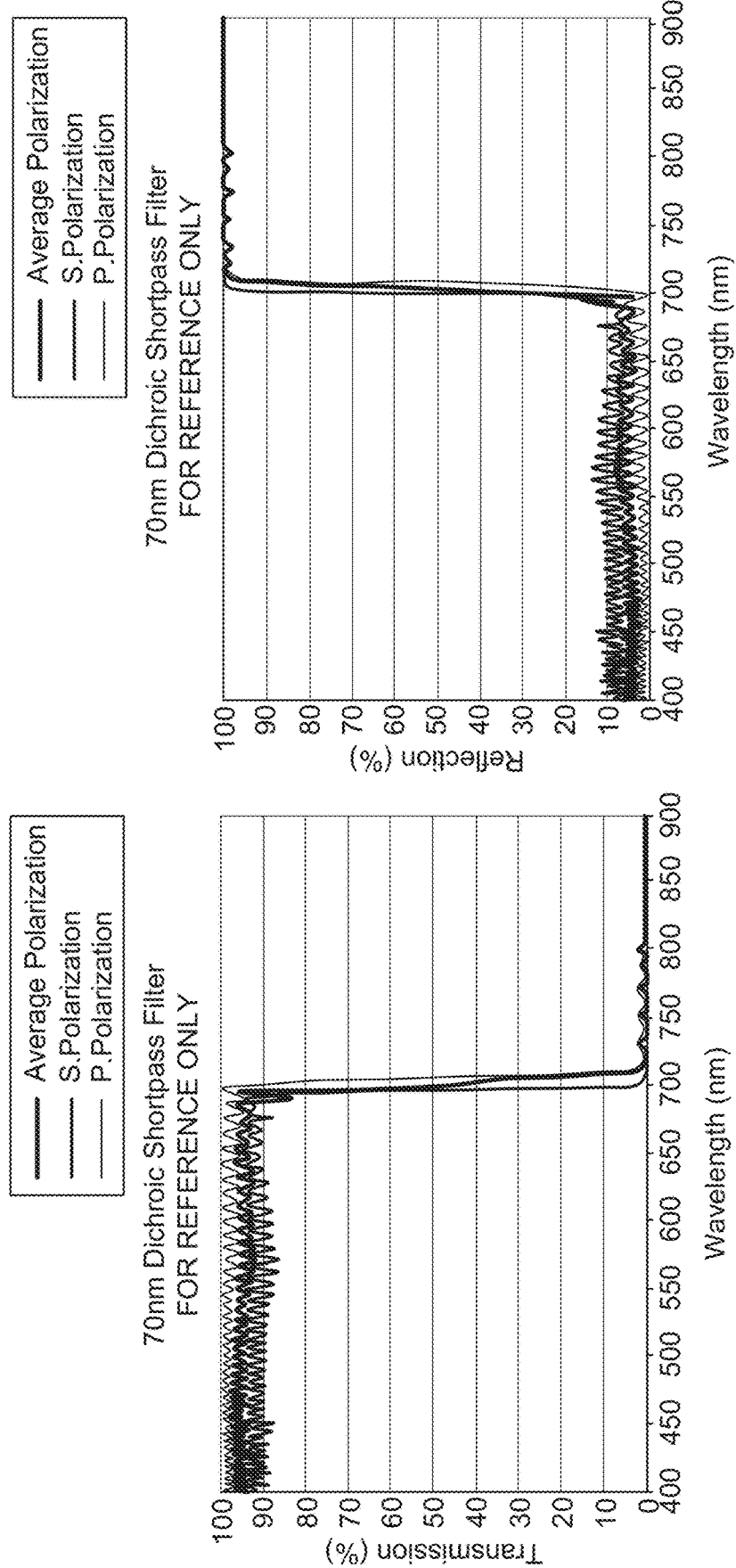
FIG. 26 is a graph of dichroic mirror's transmittance and reflectance response.
Figure 27:
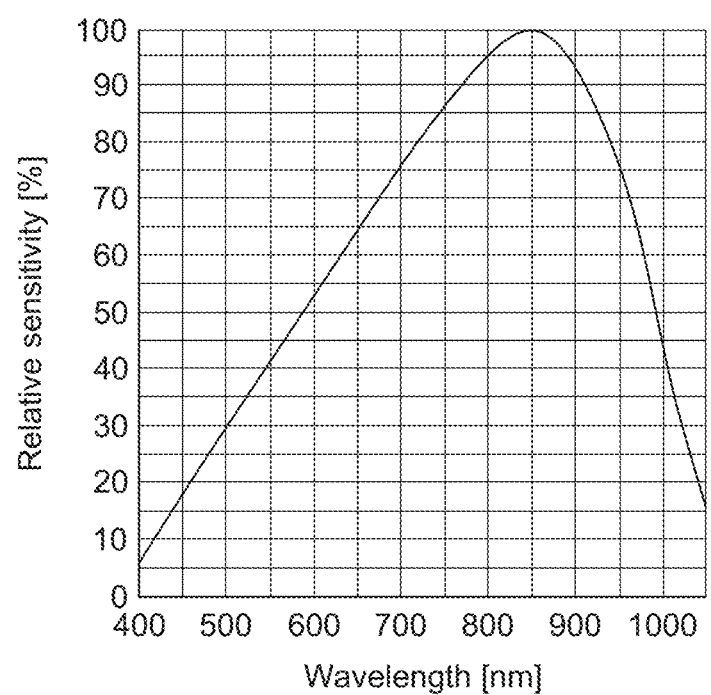
FIG. 27 shows a graph of photodiode's sensitivity across spectral wavelength range.

A 700 nm shortpass dichroic mirror 30 filters the laser 64 light from the LED 27 light and vice versa. It is coupled with the optical connector 39, which transmits the 470 nm LED 27 light to the catheter sheath 4 and reflects 850 nm laser 64 light directly to the photodiode 28. FIG. 26 shows the transmission and reflection of the mirror 30 at different frequencies. The dichroic mirror 30 is diced by the wafer manufacturer in 2.5 mm×2.5 mm dimension and is 0.5 mm thick to fit inside the optical connector 39.

Spherical Micro Lens

Figure 28:
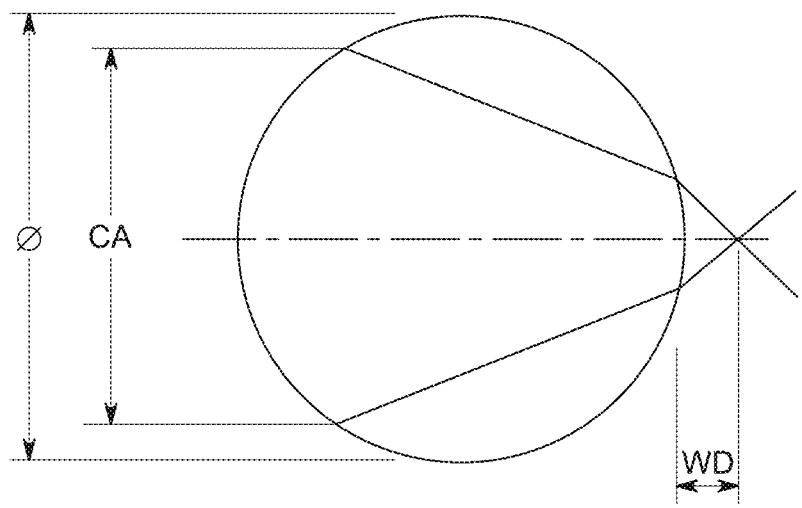
FIG. 28 is a diagram showing an optical tracing of the spherical micro lens.

The spherical ball micro lens 40 schematically shown in FIG. 28 is required in a catheter optical system to collimate the 470 nm LED 27 light to the optical fiber 21. It is an uncoated lens of size 1.0 mm in diameter with effective focal length (EFL) of 0.55 mm and clear aperture of 0.8 mm. With the given EFL and clear aperture (CA), the calculated f/CA is:

$$\frac{f}{CA} = \frac{\text{Effective Focal Length}}{\text{Clear Aperture}} = \frac{0.55 \text{mm}}{0.8 \text{mm}} = 0.69$$

The working distance of this component 40 is only 0.05 mm, so it must be placed very close to the source of LED 27.

Gradient Index (GRIN) Lens

Figure 29:
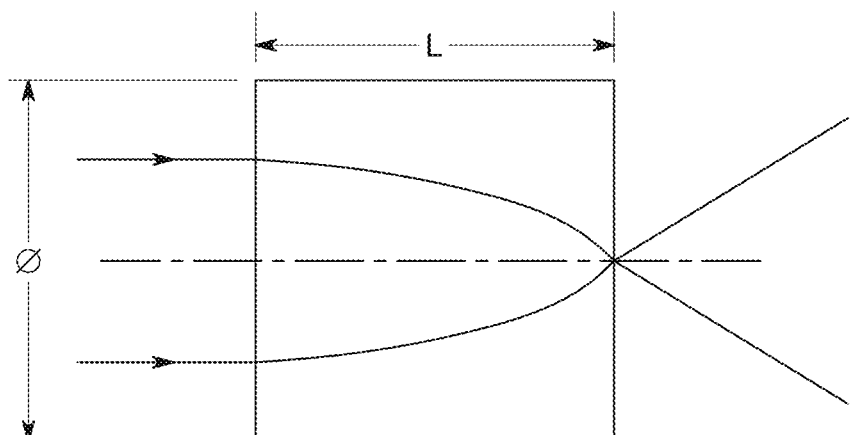
FIG. 29 is a diagram showing an optical tracing of the cylindrical GRIN lens.

The GRIN lens 41 in FIGS. 25, 29 is required in the optical system to collimate the laser 64 light from optical fiber 21 to the photodiode 28. It has 0.25-pitch with diameter of 1.0 mm. Since the length is 2.61 mm, this part will be cut to fit inside the optical connector 39. The working distance is 0.21, so it is placed very close to the fiber 21.

Figure 30:
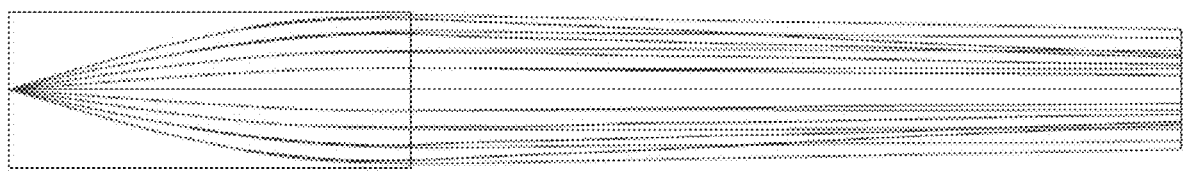
FIG. 30 is a diagram showing an optical ray tracing of the light collimation of the GRIN lens.

From the simulation, the GRIN lens 41 has different bending across the light spectrum. 470 nm of light concentrates more than the higher wavelength light (870 nm) as shown in FIG. 30.

Figure 31:
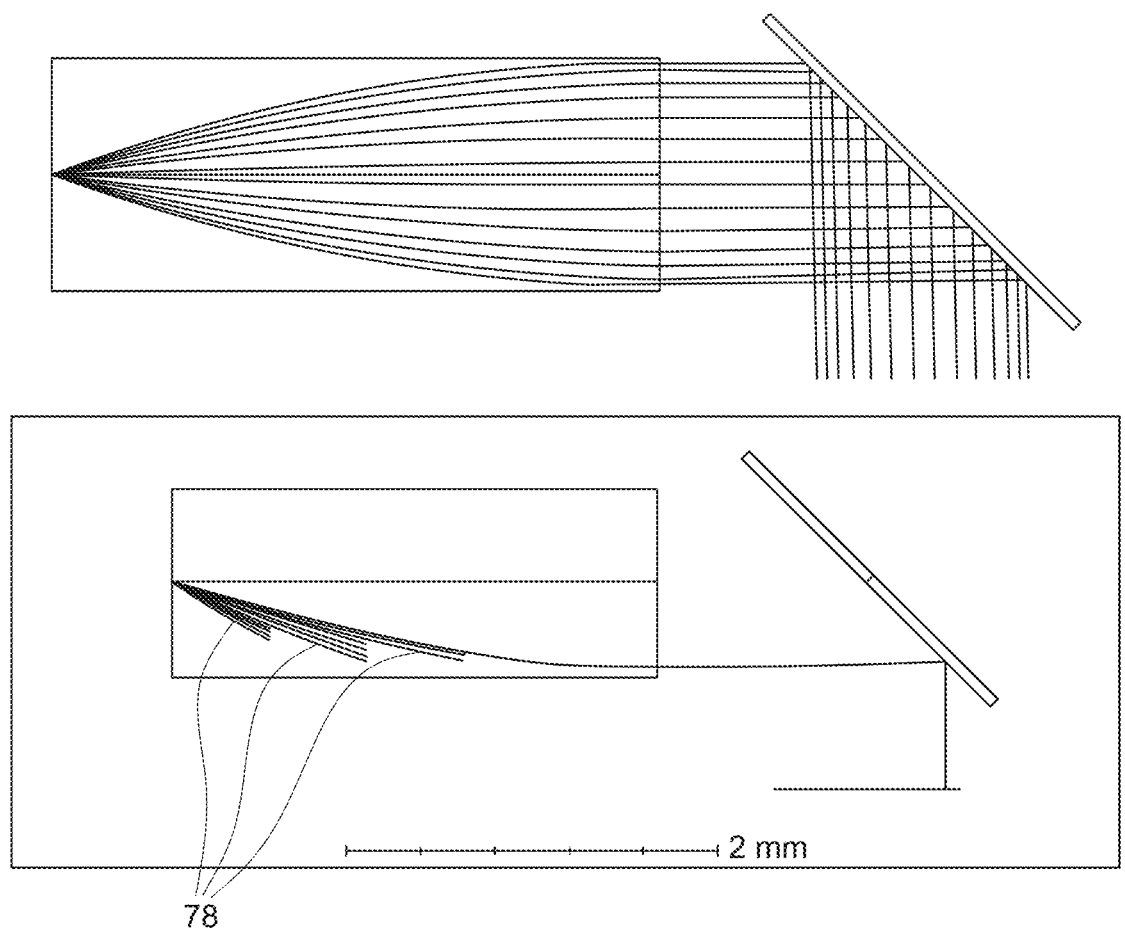
FIG. 31 is an optical ray tracing showing a light reflecting and bending simulation for the GRIN lens.

The center focus of GRIN lens 41 needs to be very precise. According to the simulation shown in FIG. 31 the light rays 78 entering the GRIN lens 41 with more than 10 μm offset from the center would disperse and be lost.

Optical Fiber

Optical fiber 21 is a single mode fiber strand with 980 μm core diameter and 1.0 mm cladding diameter. It is a plastic fiber optic (POF) which provides resilience under tension and bending. It is also a better option than a glass optical fiber when transmitting light within a visible light spectrum. It has a numerical aperture of 0.5, so the dispersion angle will be arcsin(0.5)=30°. To prevent light dispersion from the optical fiber 21, a GRIN lens 41 is attached on the optical connector 39 to collimate the light to the photodiode 28.

Sheath

Figure 32:
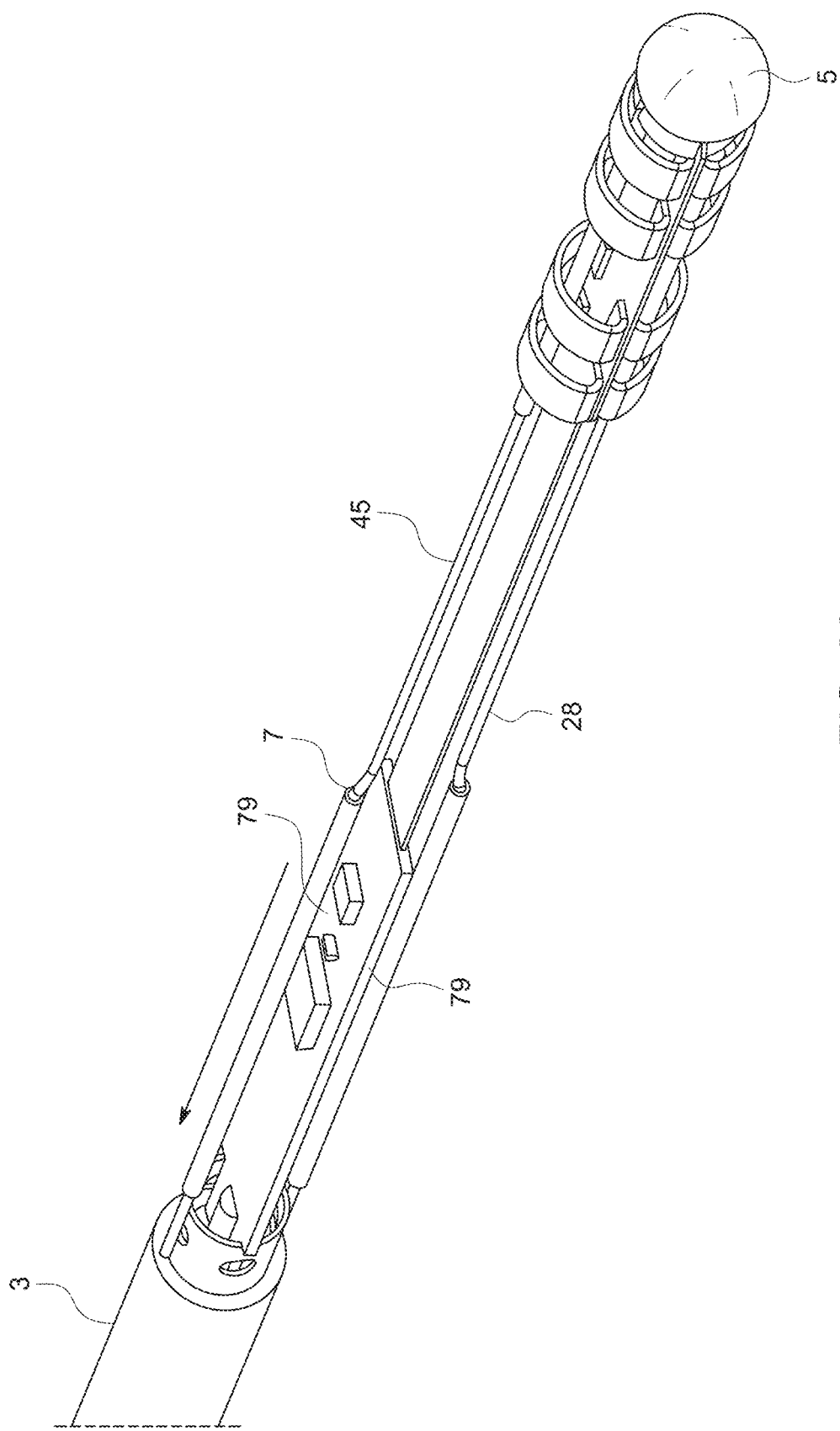
FIG. 32 is a perspective view showing the assembly procedure of the tip FPC to the catheter sheath.

The catheter sheath 3 shown in the cutaway view of FIG. 32 shows braids and layers of Prebax material to achieve required durability and flexibility. It contains a bundle of six electrical wires 8 to transmit power from the handle 4 to the tip 2 and also transmit data from the tip 2 to the handle 4. There are two pull wires 45 from the handle 4 to the center ring, located at the proximal end of tip FPC 7. These pull wires 45 perform deflection of the catheter tip 2 at one axis, 140° bend on both directions from the centerline. From the center ring, these pull wires 45 change to a safety wire 9 made of PTFE liner as shown in FIG. 21. Since the region containing FPC 7 lacks durability and resilience, two stiffeners 79 are added to the safety wire 9 to provide rigidity. If the catheter 1 employs an optical data scheme, then the electrical wire bundle 8 is replaced with a single mode optical fiber 21.

Handle

Figure 37:
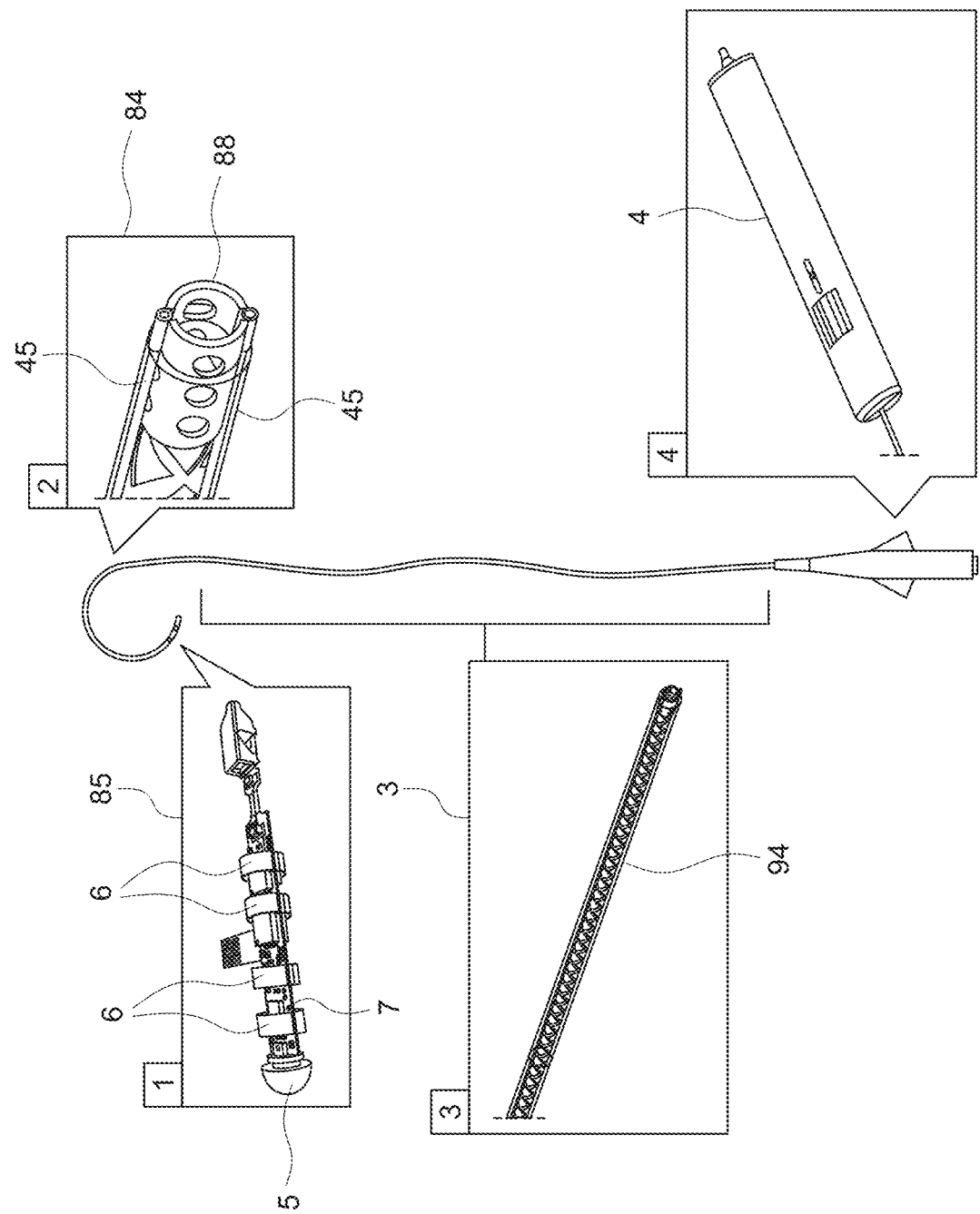
FIG. 37 is the schematic diagram of the catheter tip, sheath and handle printed circuit board (PCB).
Figure 37A:
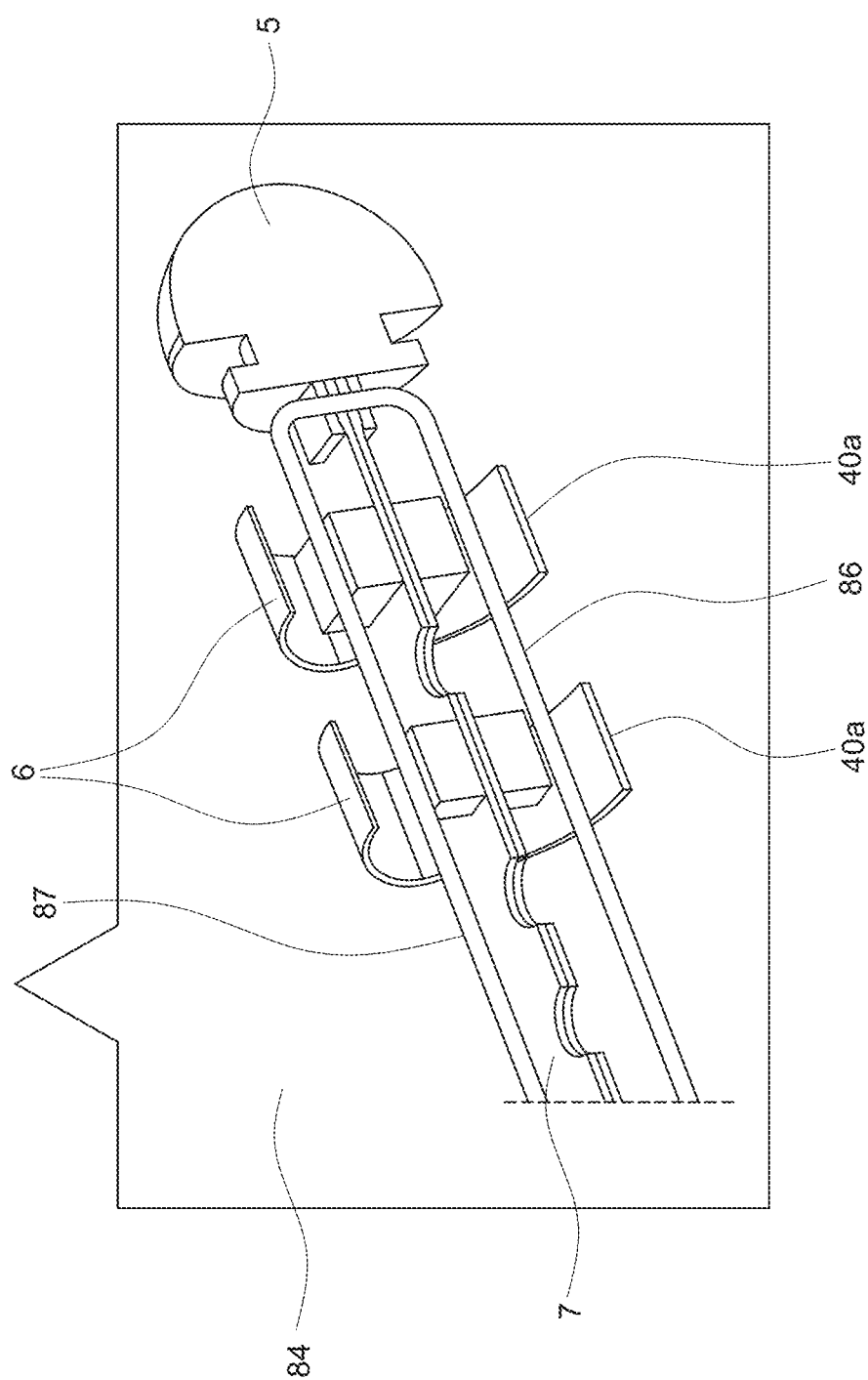
FIG. 37A is a cutaway side perspective view of the nosecone electrode and immediately adjacent portion of the catheter tip and safety wire.

Electrically, handle 4 includes a handle printed circuit board (PCB) that carries a microcontroller, a +5V DC/DC regulator, a +3.3V LDO, a power and signal isolator, an impedance measuring circuitry, and an USB connector to send the data to the mapping station as shown in FIG. 41. Mechanically, handle 4 includes a pull wire, a sled, a pulley, and a knob to perform a deflection at the tip when the knob is rotated as shown in FIG. 37.

Impedance Measuring Circuit

Figure 5:
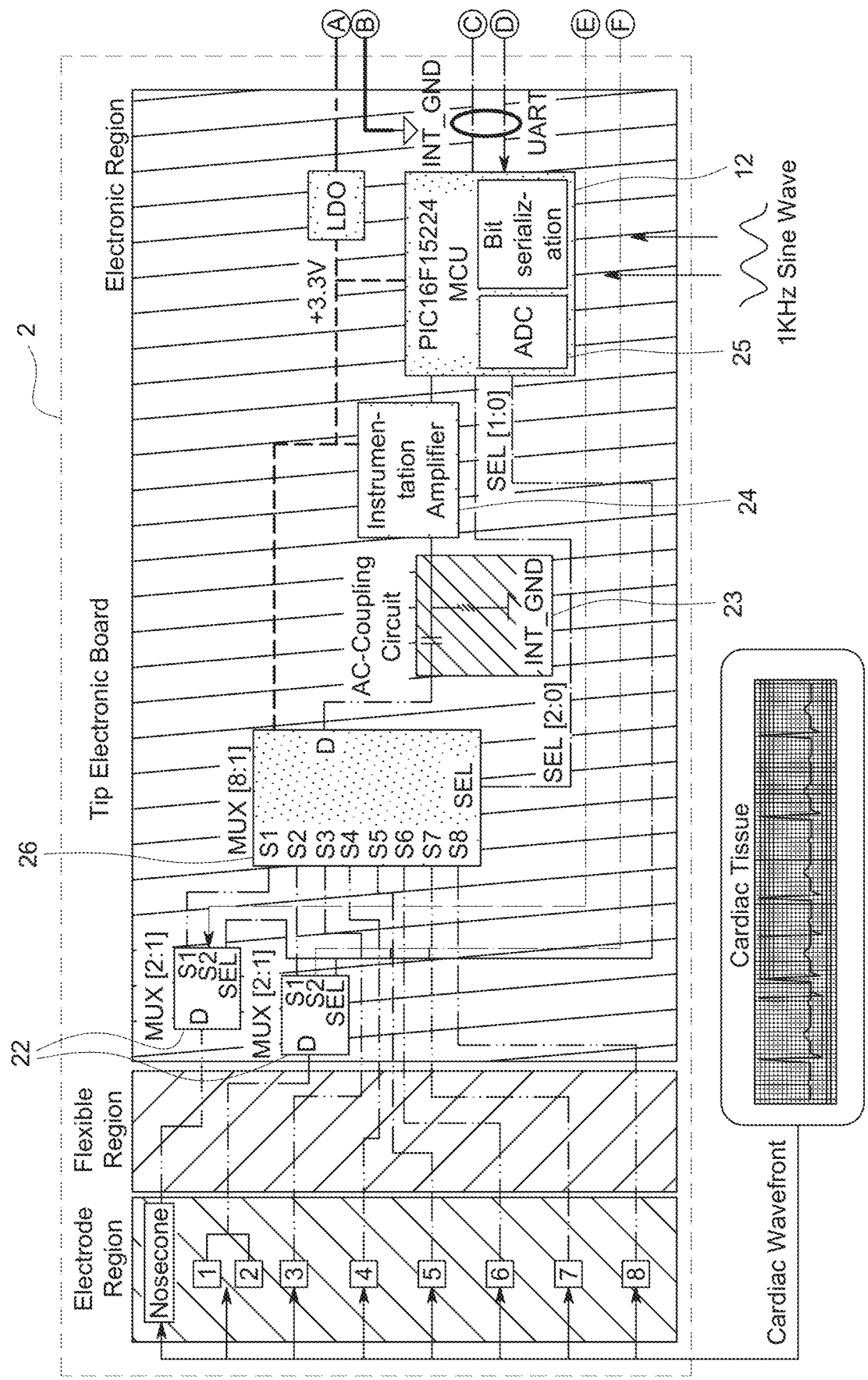
FIG. 5 is a block diagram of the electrical circuits of the catheter tip, sheath and handle of the electrical cable embodiment of FIG. 4B of the Huygens catheter.
Figure 5:
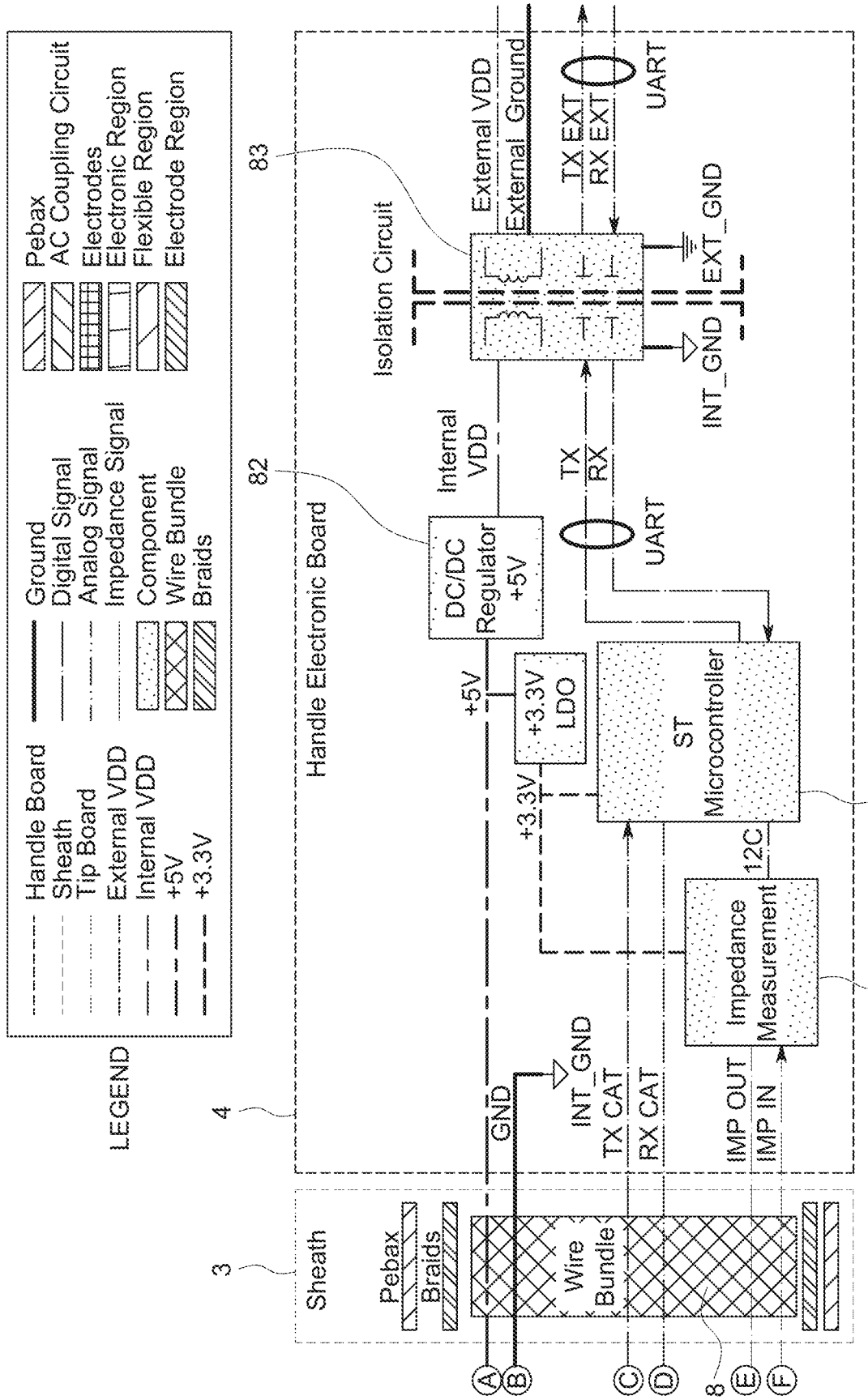

The impedance measuring circuit 80 controls the frequency of its output to indicate the impedance of the load at its input within a specified frequency range. The circuit 80 measures the sensed input impedance from 1 KΩ to 10 MΩ, but with additional circuitry, it can measure all the way down to 1000. The microcontroller 81 sets the sensing frequency to a stable 1 KHz. Circuit 80 sends a small 1 KHz current to the nosecone electrode 5 through the catheter sheath 3 and to the 2-to-1 MUX 22 as shown in FIG. 5. The current travels through the tissue load that is in contact with the nosecone electrode 5 and returns to the first ring electrode 6 and finally back to the impedance measuring circuit 80 in handle 4. Measured impedance is transmitted to handle microcontroller 81 through inter-integrated circuit, (I2C) protocol serial communication. Since the impedance of a blood pool is around 900 and cardiac tissue is around 1200, additional amplifier circuit is required in the return path of impedance sensing pins, IMP IN, IMP OUT.

5V DC/DC Regulator

5V DC/DC regulator receives a raw power from an external power source and steps down to a stable 5V, which supplies both 3.3V LDOs at the tip 2 and the handle 4. Before supplying the output voltage to the catheter electronics, external power is coupled through an isolator 83 to provide an electrically isolated system.

Signal/Power Isolator

Electrical safety is a critical requirement in a minimally invasive medical device such as catheter 1. In order to prevent the catheter 1 from delivering a fatal electrical current to the patients' body, all the power and electrical signals must be isolated from the outer environment. Texas Instrument's power and digital isolation provides up to 5000 VRMS isolation. It includes an isolation transformer for power and isolation capacitors for data inputs and outputs. The isolation circuit 83 is used in the Huygens catheter 1 is IEC 60601-1 compatible. IEC stands for International Electrotechnical Commission. IEC provides a standardized approach to testing and certification, IEC testing brings together the agreed upon set of rules, specifications, and terminology that allow manufacturers to have their devices tested for conformity.

Microcontroller

The microcontroller (MCU) 81 transmits and receives data from the tip 2 through UART communication. After receiving the digitized signal, the MCU 81 performs digital signal processing (DSP) to filter the noise and additional unwanted signals or baseline low frequency wanders. Also, it will restore the multiplexed digital signal into eight independent signals, each signal representing each electrode 6. After running the digital signal processing, all the processed data are translated to a USB protocol communicated to the isolator circuit 83 and finally sent to an external mapping station in the operating room.

Figure 34:
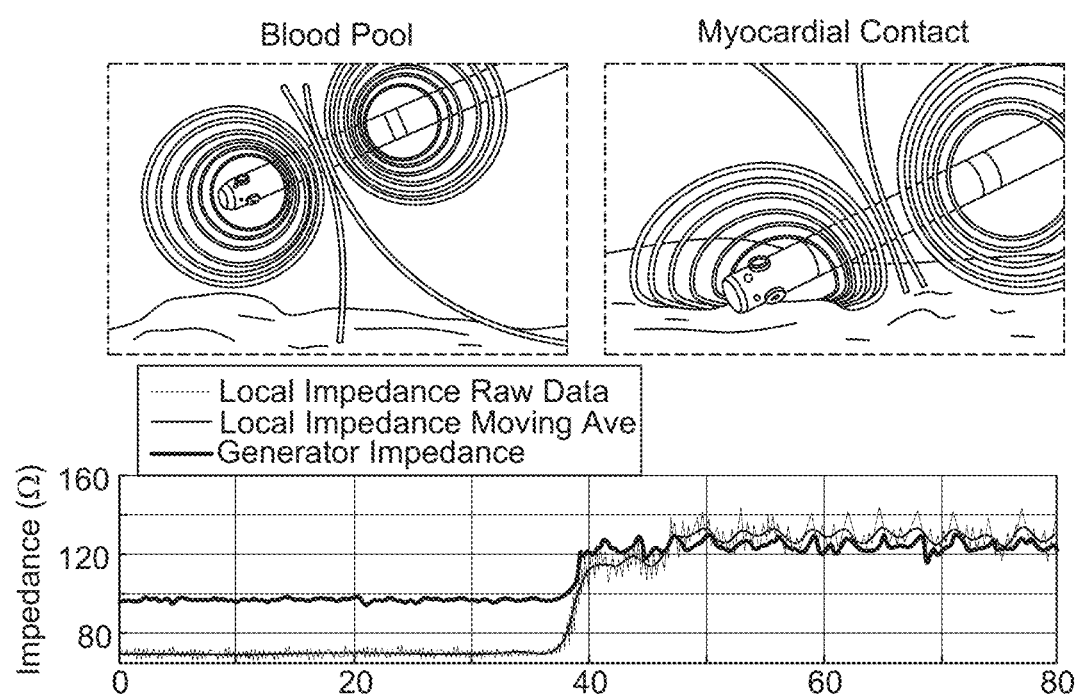
FIG. 34 is a graphic depiction of the electrical fields on the left side of the drawing of a local amplifier catheter tip in free fluid according to the illustrated embodiments of the invention and on the right side of the drawing of a local amplifier catheter tip in contact with tissue. The graph under the pictorial illustrations shows the corresponding impedance signals measured in each corresponding situation.
Figure 35:
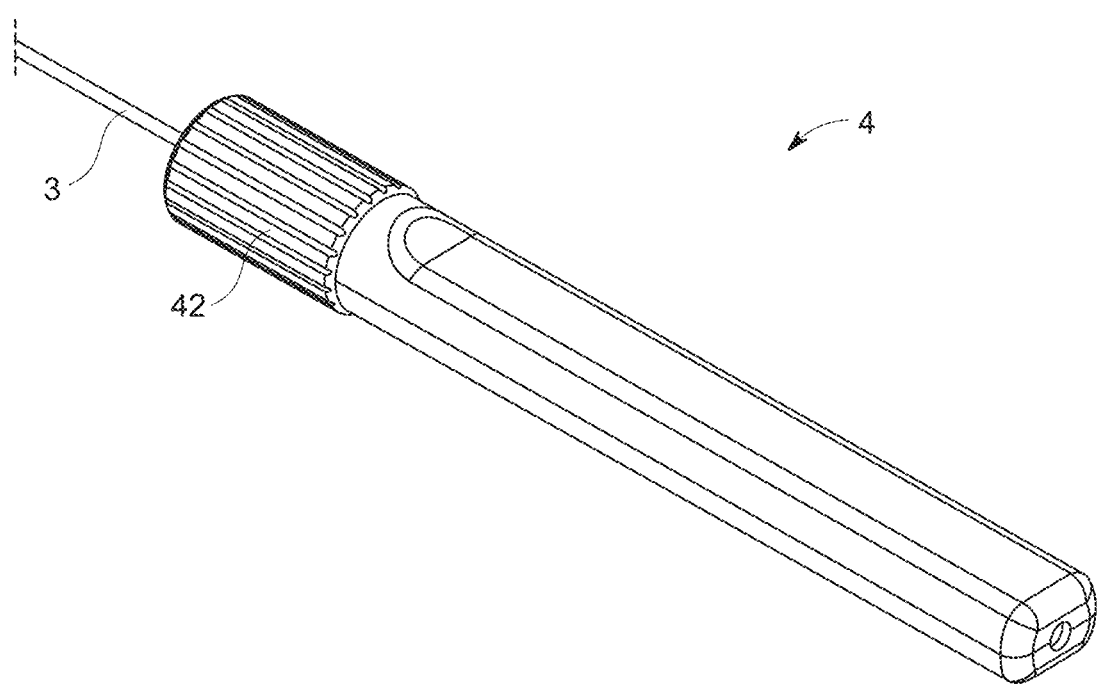
FIG. 35 is another perspective view of the catheter handle of FIG. 1.

As shown in FIG. 13, by directionally limiting the contour of a single electrode 6 to a segment of the full catheter diameter (and thereby reducing its surface to a facing area), when placed in contact with myocardial tissue, the effective contact surface area of a single split electrode is maximized, while its paired opposite electrode may still be in full contact with the blood pool. The impedance data collected by the contact electrode therefore comprises a greater degree of direct signal from the tissue being studied, while any far-field signals being received by the complementing split electrode of the pair is exposed to the blood and can be discriminated from the tissue-based signal. The sampling from the exposed electrode 6 can be discerned apart from the fine-resolution transient myocardial signals of interest in the 10 μV range, and further attenuated from the locally-amplified output by noise cancellation filtering capabilities of the digital signal processor 81 (DSP) if desired. FIG. 34 is a pair of illustrations aligned with a graph of impedance verses time, which depicts the impedance measurements made by an electrode 6 in the blood pool on the left half of the illustration and graph, and in myocardial contact on the right half of the illustration and graph. Illustrated on the left half in the bottom of FIG. 34 is a line of the local impedance as a moving average and above that a line showing impedance both below 100 ohms. On the right half, the tip of the catheter 1 makes myocardial contact and both moving average and generator impedance jumps up to about 120 ohms with local impedance raw data shown as riding on top of the moving average.

Catheter Contact Force in Forming an Electroanatomical Map

The degree of force applied to myocardial tissues by the catheter tip 2 is an existing concern in various EP catheterization procedures, most commonly that of RF ablation where firm contact with the ablation site of interest is required to create a lesion with the depth needed for full isolation. From a patient safety standpoint, force control and measurement at the catheter tip 2 is also a desirable precautionary feature to regulate the application of mechanical pressure which can be potentially damaging to endocardial structures. Similarly, contact force (CF) has significance in EP mapping procedures, where there is a direct correlation of the degree of electrode-tissue contact with the quality of the bioelectrical signal detected.

While visualization methods are of primary importance during such procedures, intuitive navigation assistance methods which can improve physician accuracy and procedural efficacy remain a promising potential as an augmentation of standard practices. Ostensibly, the design of a "smart" catheter 1 should incorporate feedback from a number of digital sensory components with the goal of reducing the abstractions of the remotely-guided tool, and enhancing the ability of the physician to better perceive the tool as an extension of his or her own body to perform the most delicate of manual tasks. The scalpel, the needle and the saw are all tactile, intuitive implements compared to a catheter, a remote-controlled camera or a marionette. To bridge the gap between the virtual and the intuitive, the Huygens catheter 1 is designed with such intention.

While the actual force of contact could be measured, the measurement of local impedance (LI) provides greater insight into catheter-tissue coupling, and this information is already at our disposal directly. Because of the material difference between the impedance of myocardial tissue and that of the blood pool medium (appx. 130Ω vs. 90Ω), any recorded signal can be evaluated by a corresponding resistance measurement; signals below a desired threshold can be selectively squelched, providing a complementary data masking channel for discriminate signal filtering between "hot" localized measurements and "cool" proximal measurements which are much more susceptible to the influence of far-field signals. This extra layer of surrogate information can be feasibly extrapolated for use in visual displays, audio enhancements, device feedback and control, including those of approximate force determination, haptic response, and conceivably extensible to pseudo-robotic automated functions.

In another embodiment, as the optical catheter gathers, digitizes and records all signals received in addition to parametric data about the state of the device itself, such as degree of deflection and orientation to a fiducial reference, this data is indexed to a lookup table, permitting various forms of detailed analysis including, but not limited to, a correlation of the extent of deflection from the control potentiometer in the handle 4 to the clarity and position of the measured impedance from the distal electrodes 5, 6. Real-time comparative operations on this matrix yields a qualitative assessment of the electrode-tissue interface at the time of recording to provide further indication of optimal contact with the target structure.

Figure 37B:
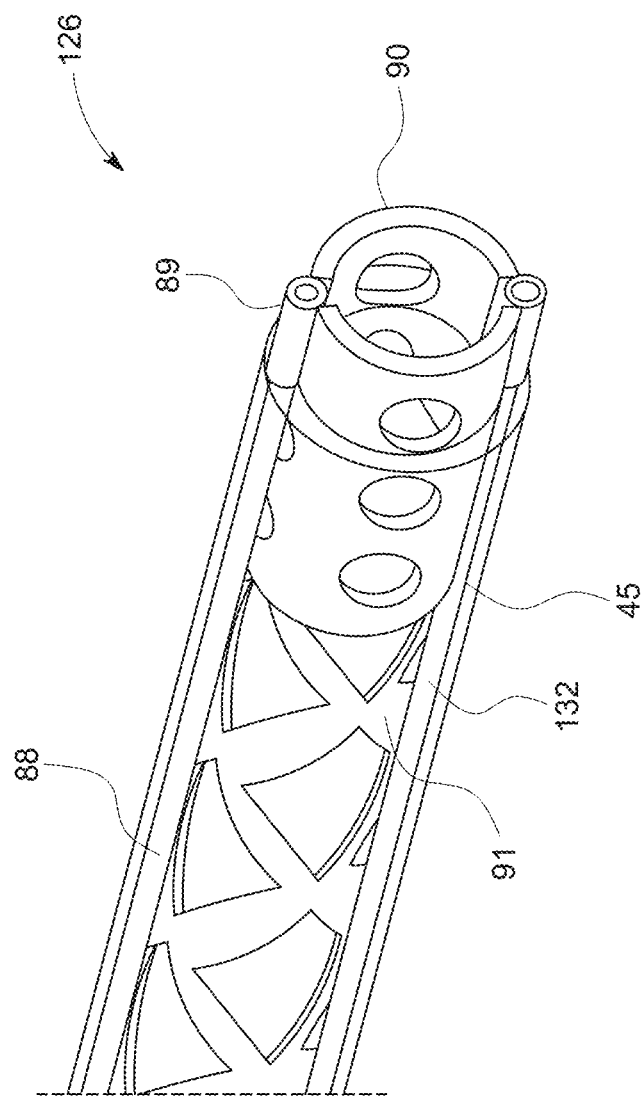
FIG. 37B is a side perspective view of the pull wire tip attachment region of the catheter tip.
Figure 37C:
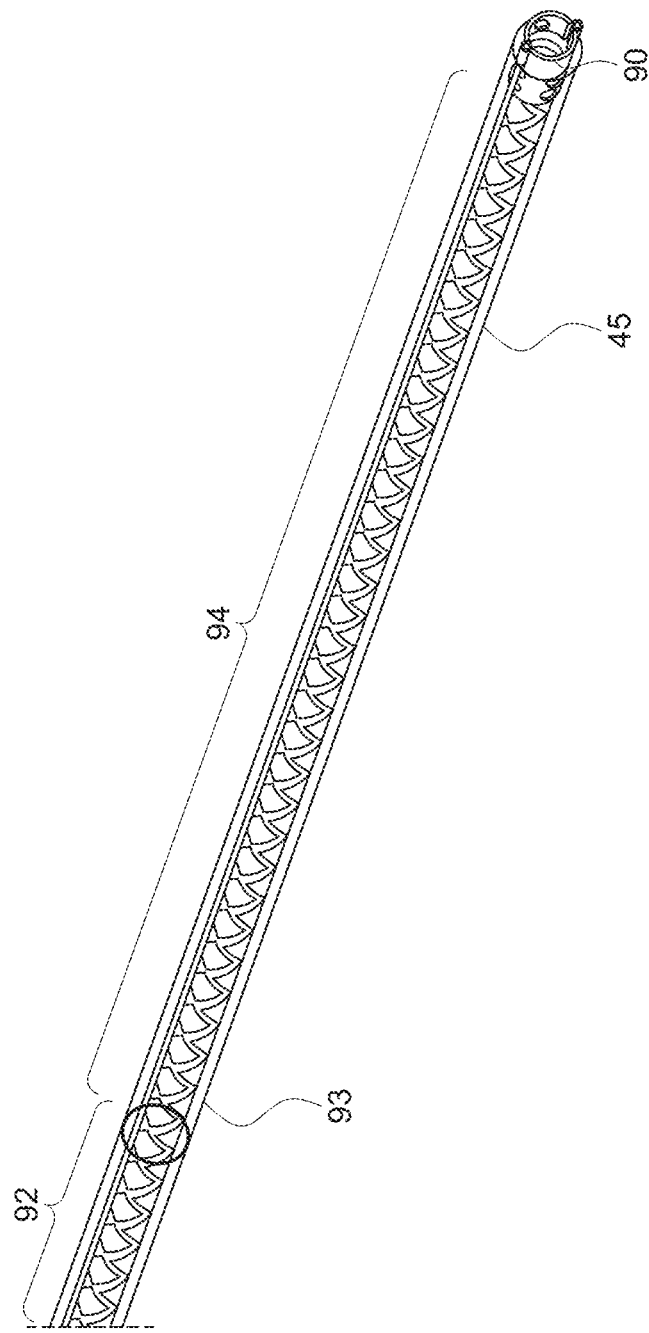
FIG. 37C is a side perspective view of the pull wires and sheath proximally located from the pull wire attachment region of FIG. 37B.

FIG. 37 illustrates the various portions of catheter 1. The distal 20 mm is comprised of the electrode assembly 85, a puller wire terminus 84 proximally distanced from electrode assembly 85 by 82 mm, the catheter cable or sheath 3 approximately 85-90 cm long, and a proximal handle 4. As shown in FIG. 37 electrode assembly 85 includes semicylindrical ring electrodes 6 and nosecone electrode 5 mounted on FPCB 7. Running parallel to FPCB 7 is an insulated safety or retention wire 86 coupled to FPCB 7 through a block 87 to each electrode pair 6 and to tip electrode 5. The construction of puller wire terminus 84 is better shown in FIG. 37B wherein opposing metallic pull wires 45 on each side of catheter cable 3 are provided with polytetrafluoroethylene (PTFE or Teflon) liners 88 to lubricate the ease of movement of wires 45 under catheter sheath 3. Wires 45 are fixed or welded into sleeves 89, which in turn are fixed to pulling ring 90. Puller ring 90 is firmly attached or fixed both to catheter cable 3 and to electrode assembly 85 comprising the distal portion of catheter 1. Differential tension on pull wires 45 applied from handle 4 allows catheter 1 and its tip 2 to be steered. The catheter cable 3, which is ordinary very soft and flexible, is sheathed by a reinforcing open flat braid 91, which renders it torquable. As shown in FIG. 37C the more proximal portion 92 of catheter 1 is comprised of inner and outer higher durometer Prebax tubing 93 (i.e. from handle 4) while the more distal portion 94 of catheter 1 is comprises of inner and outer lower durometer Prebax tubing 95 (i.e. 35 to 40 mm). Prebax is a block copolymer variation of PEBA (polyether block amide). It offers the great processing versatility across a range of flexural modulus and provides excellent mechanical, physical, chemical properties along with established biocompatibility in many commercial products. Prebax processing versatility allows it to be used in products that have a range of stiffness from soft distal segments of a catheter to stiff proximal segment for providing pushability along with smooth stiffness transitions to the distal segment for precise tip response and control. For these reasons Prebax is one of the most commonly specified polymer systems for catheter and medical tubing applications.

Figure 38:
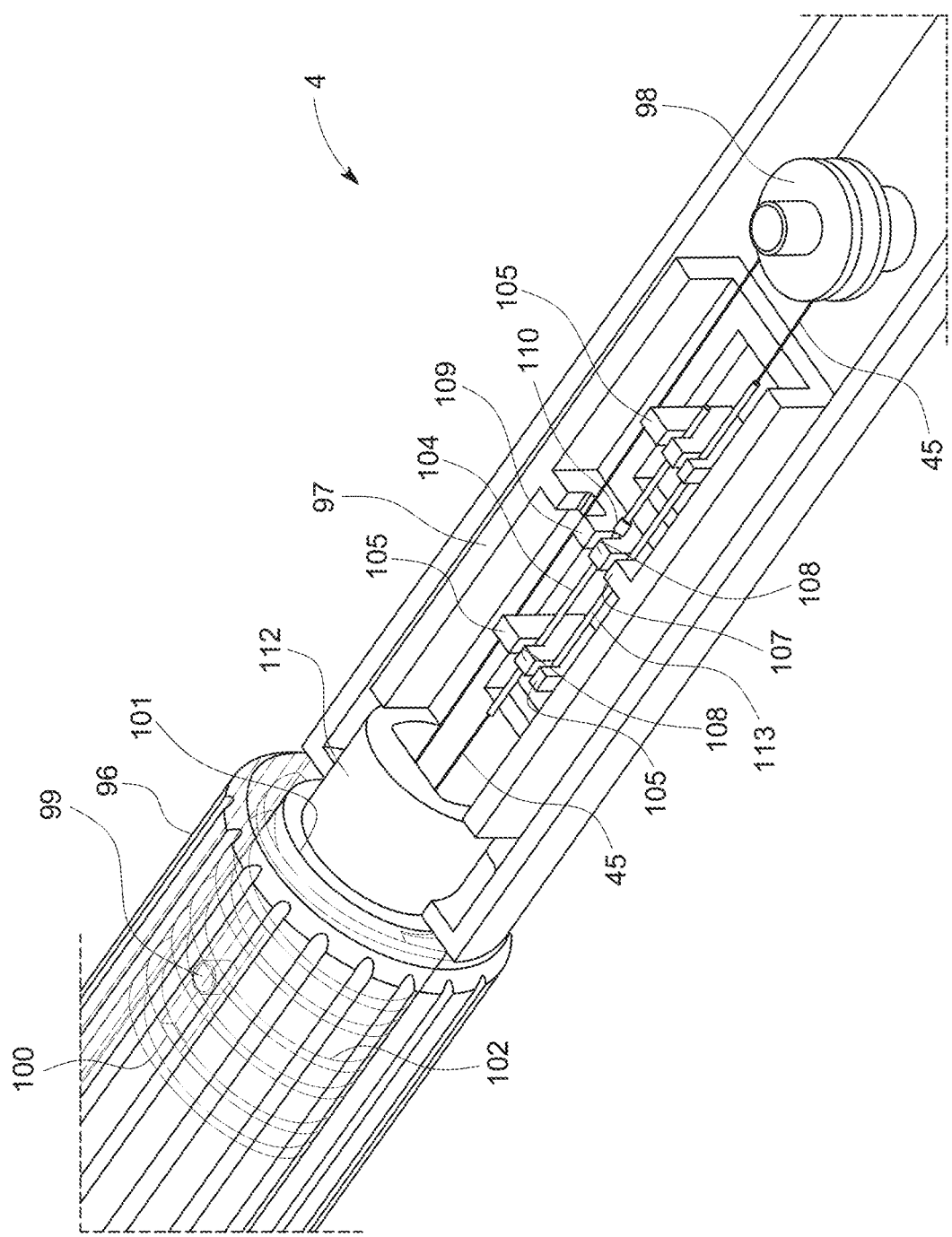
FIG. 38 is a top perspective opened internal view of the catheter handle showing the operation of the rotary knob.
Figure 39A:
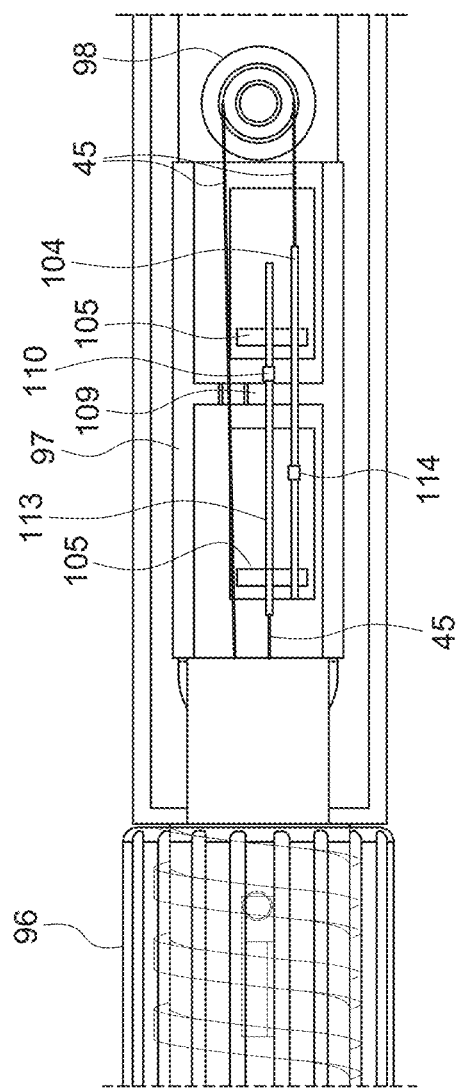
FIGS. 39A and 39B are diagrams which show the operation of the pull wire to deflect the catheter tip in the full proximal position of the knob and pin, and in the full distal position of the knob and pin respectively.

On the proximal end of catheter cable 3 is a manually operated embodiment of the handle 4 shown in cutaway view of FIG. 38, which includes a knob 96, sled 97 longitudinally movable in handle 4 and pulley 98. In FIG. 38 the distal end of handle 4 is to the left in the drawing and the proximal end of handle 4 is the right in the drawing. As seen in the transparent view of FIG. 38 a pin 99 is retained in a longitudinal slot 100 defined in a stationary cylindrical body 101 concentric with cylindrical knob 96. Pin 99 engages a helical track 102 defined into the interior hollow cylindrical surface of knob 96. As knob 96 is rotated, pin 99 is longitudinally advanced or retracked in slot 100. Pin 99 is connected to a longitudinally movable cylindrical body 112 concentrically disposed in cylindrical body 101 in which slot 100 is defined. Body 112 is connected to sled 97, so that as pin 99 is longitudinally displaced in slot 100 and body 112 longitudinally displaced, sled 97 with guide 109 is similarly longitudinally displaced relative to fixed guides 105 on both sides of guide 109. Guides 105 and 109 have aligned slots 108 defined in each of them into which longitudinally movable rods 104 and 113 are retained and guided. Rod 104 has a stop 110 disposed thereon between movable guide 109 and the proximal fixed guide 105 as seen in FIG. 38. As best seen in FIGS. 39A and 239B rod 113 has a stop 114 disposed thereon between movable guide 109 and the distal fixed guide 105. One end of pull wire 45, led from sheath 3 through handle 4, is connected to the distal end of rod 104 and the opposing end of pull wire 45 is connected to the proximal end of rod 113. The opposing end of pull wire 45 is connected to rod 113 and is bent around pulley 98 and led distally out of handle 4 to sheath 3.

Thus, as best seen in FIG. 39A when knob 96 is rotated to move pin 99 to its most proximal position, the end of pull wire 45 connected to rod 104 is fully tightened and sled 97 moved to its most proximal position in handle 4, moving rod 104 by means of stop 110 bearing against movable guide 109 and moving rod 104 to its most proximal position. This allows rod 113 to longitudinally move in the proximal direction thereby slackening the opposing end pull wire 45 connected to rod 113. The degree of slackening is determined by the mechanics in catheter tip 2 and is only limited by means of stop 114 on rod 113 bearing against movable guide 109, if at all. The net result is that catheter tip 2 will be bent in a first direction. The degree of bending of catheter tip 2 will depend on how much pull wires 45 are tensioned and slackened or by the degree of rotation of knob 96.

Figure 39B:
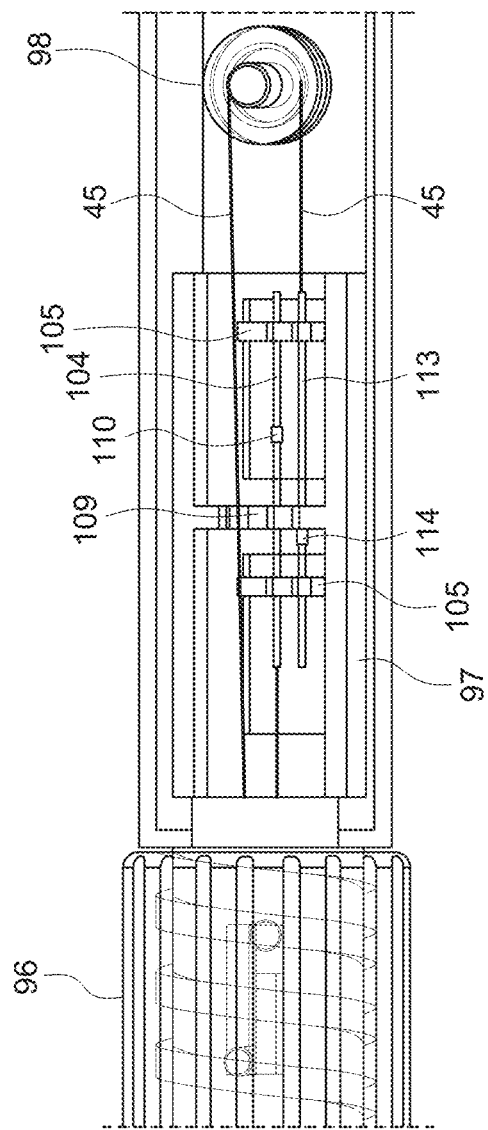

Similarly, as seen in FIG. 39B, when knob 96 is rotated to move pin 99 to its most distal position, the end of pull wire 45 connected to rod 113 is fully tightened and sled 97 moved to its most distal position in handle 4, moving rod 113 by means of stop 114 bearing against movable guide 109 and moving rod 113 to its most distal position. This allows rod 104 to longitudinally move in the distal direction thereby slackening the opposing end pull wire 45 connected to rod 104. The degree of slackening is determined by the mechanics in catheter tip 2 and is only limited by means of stop 110 on rod 104 bearing against movable guide 109, if at all. The net result is that catheter tip 2 will be bent in a second direction opposing the first direction.

Optical fiber 21 from catheter sheath 3 is lead back through handle 4 to PCB 15 on which is the circuitry of FIG. 3A. With the catheter handle control, the tip 2 of catheter 1 must be able to perform an axial movement of 180° in each of two defined directions. Also, the tip 2 needs to maintain its position when the pull wire 45 is at rest. The handle 4 provides many features such as motorized tip control and tip-pressure haptic feedback for ergonomics, as well as contact-force measurement that can accomplish far more accurate diagnostics.

The rapid growth in illness and death related to hypertension has put tremendous pressure on the medical field to develop better cures for those whose high-blood pressure cannot be remedied with medication and life-style changes. One of the potential cures that has been of great interest is in the area of renal denervation (RD). RD seeks to minimize or eliminate persistent hypertension through the ablation of the renal nerves in the kidney that regulate the release of renin, a protein produced by the kidneys that regulates the body's mean arterial blood pressure. The basic proposition and understanding of how RD can impact hypertension has been well researched and extrapolated, but effectively being able to perform the procedure with consistent degrees of success has fallen far short of expectations. The issue is twofold and lies in the inability for current EP mapping and detection tools to be able to overcomes these challenges.

The first is that unlike the nerves in the heart, which are well known and fixed in their location that when ablated restore normal rhythms, the sympathetic renal nerves formation and location is individualized to each person. Much like a tree, the renal nerve plexus consists of a branching network of nerves that grow out from one another and attach to the renal artery in completely random locations. This makes locating them much harder to do.

The second issue is that the electrical signals that the nerves produce is not a consistent regular pattern as can be measured in the beating of the heart, even an irregular beating one. Instead, electrical impulses only occur when a biologic event occurs that triggers the nerve to signal the brain, which then signals back to the kidney to release renin. It is much like trying to find a road that can only be seen when the streetlight comes on with no way of knowing when that will happen. In addition, the signals that are produced are of a very high frequency and extremely short duration that makes capturing them for mapping purposes extremely difficult with the resolution of current EP mapping systems.

Including a programmable pulse generator, the disclosed EP catheter delivers a pacing pulse at a fixed rate and then senses a return response from the renal nerve ending like the sensed local native cardiac signal. In this way, the active renal nerves are mapped and an appropriate renal denervation or ablation plan is devised and executed.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An electrophysiology catheter for combination with an external mapping station comprising:
   a handle forming a proximal portion of the electrophysiology catheter;
   a flexible sheath forming an intermediary portion of the electrophysiology catheter, the flexible sheath forming a communication channel;
   a movable catheter tip forming a distal portion of the electrophysiology catheter;
   wherein the handle includes circuitry for processing digital data signals received from the catheter tip via the communication channel and for providing power to the catheter tip via the communication channel, the handle being configured to control movement of the catheter tip;
   wherein the catheter tip includes an electrode region forming a most distal portion of the catheter tip, a circuitry region forming a least distal portion of the catheter tip, and a flexible bending region between the electrode region and the circuitry region, the catheter tip further comprising:
a plurality of electrodes disposed in an electrode region in a most distal portion of the catheter tip;
one or more multiplexers disposed in the circuitry region and in communication with the plurality of electrodes, the one or more multiplexers being configured to combine tissue-based electrophysiological signals received at the plurality of electrodes;
amplification circuitry disposed in the circuitry region and in communication with the one or more multiplexers, the amplification circuitry being configured to amplify the combined tissue-based electrophysiological signals;
digitizing circuitry disposed in a circuitry region and in communication with the amplification circuitry, the digitizing circuitry being configured to digitize the amplified and combined tissue-based electrophysiological signals; and
controller circuitry disposed in the circuitry region and in communication with the digitizing circuitry, the controller circuitry being configured to create and communicate the digital data signals containing the digitized, amplified and combined tissue-based electrophysiological signals to the circuitry in the handle of the electrophysiology catheter via the communication channel in the flexible sheath of the electrophysiology catheter.

2. The electrophysiology catheter of claim 1, wherein the digital data signals containing the digitized, amplified and combined tissue-based electrophysiological signals comprise a biopotential measurement representing energy contents on a spatial domain and a time domain of a complex electrophysiological waveform which defines a recursive relationship between a graphical representation of the complex electrophysiological waveform and an underlying biopotential substrate which causes the complex electrophysiological waveform.

3. The electrophysiology catheter of claim 1, wherein the amplification circuitry comprises a local amplifier active sensor array that performs impedance spectroscopy on the combined tissue-based electrophysiological signals.

4. The electrophysiology catheter of claim 1, wherein the plurality of electrodes comprise an array forming geometry configurations.

5. The electrophysiology catheter of claim 1, wherein the digital data signals containing the digitized, amplified and combined tissue-based electrophysiological signals define distinguishable near field and far field components.

6. The electrophysiology catheter of claim 1, wherein the circuitry in the handle comprises a digital signal processor, a laser controlled by the digital signal processor and coupled to an optical fiber forming the communication channel, and a dichroic mirror for feeding back a portion of light from the laser to a photodiode coupled to the digital signal processor to regulate the laser.

7. The electrophysiology catheter of claim 1, wherein the amplification circuitry comprises a plurality of amplifier application specific integrated circuits (ASICs) coupled to corresponding ones of the plurality of electrodes, and wherein the controller circuitry includes a light application specific integrated circuit (ASIC).

8. The electrophysiology catheter of claim 1, wherein the catheter tip comprises:
an optical connector coupled to an optical fiber forming the communication channel in the flexible sheath, the optical connector including a photodiode to convert an optical signal from the optical fiber into an electrical signal, and the optical connector including an LED to convert an electrical signal into an optical signal communicated to the optical fiber;
a voltage regulator coupled to the photodiode and powered by a power optical signal received by the photodiode; and
a charge pump coupled to the voltage regulator.

9. The electrophysiology catheter of claim 1, wherein the communication channel is an optical channel.

10. The electrophysiology catheter of claim 9, wherein the catheter tip includes optical circuitry for transmitting the digital data signals containing the digitized, amplified and combined tissue-based electrophysiological signals as optical signals.

11. The electrophysiology catheter of claim 1, wherein the communication channel is an electrical channel.

12. The electrophysiology catheter of claim 1, wherein the plurality of electrodes includes a nosecone electrode.

13. The electrophysiology catheter of claim 12, wherein the one or multiplexers include a first multiplexer in communication with the nosecone electrode, a second multiplexer in communication with a first pair of the plurality of the electrodes, and a third multiplexer in communication with first multiplexer, the second multiplexer and the remaining plurality of electrodes.

14. The electrophysiology catheter of claim 13, wherein the first multiplexer is configured to select a function of the nosecone electrode, the function comprising one of impedance detection or biopotential reading.

15. The electrophysiology catheter of claim 13, wherein the second multiplexer is configured to select a function of the first pair of the plurality of electrodes, the function comprising one of impedance detection or biopotential reading.

16. The electrophysiology catheter of claim 1, wherein the circuitry in the handle is configured to provide power to the catheter tip by transmitting an optical signal having a first wavelength.

17. The electrophysiology catheter of claim 16, wherein the controller circuitry is configured to communicate the digital data signals containing the digitized, amplified and combined tissue-based electrophysiological signals to the circuitry in the handle by transmitting an optical signal having a second wavelength.

18. The electrophysiology catheter of claim 1, wherein the catheter tip includes a flexible bending region between the electrode region and the circuitry region, and wherein the one or more multiplexers are in communication with the plurality of electrodes via the flexible bending region.

19. The electrophysiology catheter of claim 1, wherein the catheter tip is movable.

20. The electrophysiology catheter of claim 19, further comprising:
one or more pull wires that extend from the handle to the catheter tip, the handle being configured to allow the one or more pull wires to be pulled to deflect the catheter tip from a longitudinal axis.

21. A system comprising:
an external mapping station; and
an electrophysiology catheter for combination with the external mapping station comprising:
a handle forming a proximal portion of the electrophysiology catheter;

a flexible sheath forming an intermediary portion of the electrophysiology catheter, the flexible sheath forming a communication channel;

a movable catheter tip forming a distal portion of the electrophysiology catheter;

wherein the handle includes circuitry for processing digital data signals received from the catheter tip via the communication channel and for providing power to the catheter tip via the communication channel, the handle being configured to control movement of the catheter tip;

wherein the catheter tip includes an electrode region forming a most distal portion of the catheter tip, a circuitry region forming a least distal portion of the catheter tip, and a flexible bending region between the electrode region and the circuitry region, the catheter tip further comprising:

a plurality of electrodes disposed in an electrode region in a most distal portion of the catheter tip;

one or more multiplexers disposed in the circuitry region and in communication with the plurality of electrodes, the one or more multiplexers being configured to combine tissue-based electrophysiological signals received at the plurality of electrodes;

amplification circuitry disposed in the circuitry region and in communication with the one or more multiplexers, the amplification circuitry being configured to amplify the combined tissue-based electrophysiological signals;

digitizing circuitry disposed in a circuitry region and in communication with the amplification circuitry, the digitizing circuitry being configured to digitize the amplified and combined tissue-based electrophysiological signals; and controller circuitry disposed in the circuitry region and in communication with the digitizing circuitry, the controller circuitry being configured to create and communicate the digital data signals containing the digitized, amplified and combined tissue-based electrophysiological signals to the circuitry in the handle of the electrophysiology catheter via the communication channel in the flexible sheath of the electrophysiology catheter.

22. The system of claim 21, wherein the external mapping station comprises an imaging system including an impedance mapping apparatus, the imaging system being configured to use the digital data signals containing the digitized, amplified and combined tissue-based electrophysiological signals to locate a target within an anatomical context and provide geometric coordinates of specific anatomical destination including identifying different types of arrythmia.

23. The system of claim 21, wherein the external mapping station is configured to use the digital data signals containing the digitized, amplified and combined tissue-based electrophysiological signals to characterize fractionation potentials recorded in scarred myocardial tissue, which serve as ablation targets, pulmonary vein potentials and accessory pathway potentials.

24. The system of claim 21, wherein the external mapping station is configured to use the digital data signals containing the digitized, amplified and combined tissue-based electrophysiological signals to generate a standard model for assessing boundary conditions yielding consistent and repeatable data under similar conditions.

25. The system of claim 24, wherein the standard model unifies diagnostic observations under a measurement technique to define an intracardiac electrogram (EGM) as energetic events, which provides a translation between an electrical map and its tissue substrate so that the tissue substrate is directly correlated to a pathophysiology.

26. The system of claim 25, wherein the defined intracardiac electrogram (EGM) comprises a graphical representation of an energetic bioevent, based on a dielectric (K) and conductivity (a) measurements of underlying tissues.

* * * * *